US012703689B2

(12) United States Patent
Saha et al.

(10) Patent No.: US 12,703,689 B2
(45) Date of Patent: Aug. 11, 2026

(54) FURAN BASED COMPOSITIONS AND METHODS OF MAKING THEREOF

(71) Applicant: UNIVERSITY OF DELAWARE, Newark, DE (US)

(72) Inventors: Basudeb Saha, Newark, DE (US); Sibao Liu, Nanchang (CN); Dionisios Vlachos, Voorhees, NJ (US)

(73) Assignee: University Of Delaware, Newark, DE (US)

( * ) Notice: Subject to any disclaimer, the term of this patent is extended or adjusted under 35 U.S.C. 154(b) by 801 days.

(21) Appl. No.: 16/639,314

(22) PCT Filed: Aug. 17, 2018

(86) PCT No.: PCT/US2018/046965

§ 371 (c)(1),
(2) Date: Feb. 14, 2020

(87) PCT Pub. No.: WO2019/036663

PCT Pub. Date: Feb. 21, 2019

(65) Prior Publication Data

US 2021/0040055 A1 Feb. 11, 2021

Related U.S. Application Data

(60) Provisional application No. 62/546,603, filed on Aug. 17, 2017.

(51) Int. Cl.

| | |
|---|---|
| ***C07D 307/10*** | (2006.01) |
| ***A61K 8/49*** | (2006.01) |
| ***A61K 47/22*** | (2006.01) |
| ***A61Q 19/00*** | (2006.01) |
| ***C07C 1/22*** | (2006.01) |
| ***C07C 9/16*** | (2006.01) |
| ***C07D 307/38*** | (2006.01) |
| ***C10M 105/04*** | (2006.01) |
| ***C10M 105/18*** | (2006.01) |
| ***C10M 111/02*** | (2006.01) |

(52) U.S. Cl.

CPC .......... *C07D 307/10* (2013.01); *A61K 8/4973* (2013.01); *A61K 47/22* (2013.01); *A61Q 19/00* (2013.01); *C07C 1/22* (2013.01); *C07D 307/38* (2013.01); *C10M 105/04* (2013.01); *C10M 105/18* (2013.01); *C10M 111/02* (2013.01); *C07C 9/16* (2013.01)

(58) Field of Classification Search

CPC ........ C10M 105/04; C10M 2203/0206; C10N 2020/02; C10N 2020/065; C07C 9/16; C07C 9/22

See application file for complete search history.

(56) References Cited

U.S. PATENT DOCUMENTS

| | | | | |
|---|---|---|---|---|
| 2,681,917 | A | 6/1954 | Fauque | |
| 4,663,306 | A * | 5/1987 | Cantrell | A61K 39/05 424/282.1 |
| 4,803,070 | A | 2/1989 | Cantrell et al. | |
| 2010/0092565 | A1 | 4/2010 | Sato | |
| 2011/0009300 | A1 | 1/2011 | Elomari et al. | |
| 2012/0308506 | A1 | 12/2012 | Oku et al. | |
| 2013/0066089 | A1 | 3/2013 | West et al. | |
| 2015/0094246 | A1 | 4/2015 | Bredsguard | |
| 2016/0137945 | A1 | 5/2016 | Carrera et al. | |

FOREIGN PATENT DOCUMENTS

| | | | | |
|---|---|---|---|---|
| CN | 101923077 | A | 12/2010 | |
| EP | 3178908 | A1 | 6/2017 | |
| WO | WO 2007/068797 | * | 6/2007 | C10M 105/00 |
| WO | 2011007362 | A1 | 1/2011 | |
| WO | 2013028307 | A1 | 2/2013 | |
| WO | 2014207235 | A1 | 12/2014 | |
| WO | 2015148412 | A2 | 10/2015 | |

OTHER PUBLICATIONS

Johnson et al., Journal of Chemical, Biological and Physical Sciences, Section B: Biological Science, Aug.-Oct. 2012, vol. 2, No. 4, pp. 1842-1848.*

Danielski et al., Chemical Engineering and Processing: Process Intensification, vol. 46, No. 2, Feb. 2007, pp. 99-106.*

Myha et al., ScienceRise: Pharmaceutical Science, No. 5 (33), 2021.*

Li et al., Journal of Chinese Mass Spectrometry Society, vol. 28, No. 2, May 2007.*

Zhang et al., Shandong Huagong (2007), 36(8), pp. 36-39.*

Cermola et al., "Bis-furyl Alditols via $SnC1_4$- or $ZnC1_2$-catalysed Reaction of Furans with Sugars," Tetrahedron Letters, vol. 52, Oct. 15, 2011, pp. 7058-7060, XP028596935.

Liu et al., "Catalytic Hydrodeoxygenation of High Carbon Furylmethanes to Renewable Jet-fuel Ranged Alkanes over a Rhenium-Modified Iridium Catalyst," ChemSusChem, vol. 10(16), Jul. 27, 2017, pp. 3225-3234, XP055780125.

(Continued)

*Primary Examiner* — Alicia L Otton

(74) *Attorney, Agent, or Firm* — BUCHANAN INGERSOLL & ROONEY PC

(57) ABSTRACT

Disclosed herein are processes for the preparation of compounds of formula (I) from one or more bio-derived reactants, and their use as base oils:

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein a and c are independently 0 or 1, b and d are independently 1 or 2, x and y are independently 1 or 2, dependent upon the values of a-d, m and o are independently 0 or 1, n is an integer of 0-6, and each A is independently an unsaturated furan ring, a partially saturated furan ring, a saturated furan ring, or $—(CH_2)_4—$. Also, $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not hydrogen, and the total carbon content of the compound of formula (I) is in the range of 20-62.

19 Claims, 8 Drawing Sheets

(56) References Cited

OTHER PUBLICATIONS

Corma et al., "Production of High-Quality Diesel from Biomass Waste Products," Angewandte Chemie International Edition, vol. 50(10), Jan. 31, 2011, pp. 2375-2378, XP055072571.
Corma et al., "Production of High Quality Diesel from Cellulose and Hemicellulose by the Sylvan Process: Catalysts and Process Variables." Energy & Environmental Science, vol. 5(4), Jan. 2012, pp. 6328-6344, XP055780131.
Corma et al., "High-Quality Diesel from Hexose- and Pentose-Derived Biomass Platform Molecules," ChemSusChem, vol. 4(11), Oct. 19, 2011, pp. 1574-1577, XP055780134. 2011.
Li et al., "Synthesis of High-Quality Diesel with Furfural and 2-Methylfuran from Hemicellulose," ChemSusChem, vol. 5(10), Aug. 21, 2012, pp. 1958-1966, XP055780142.
Balakrishnan et al., "Supporting Information for Production of Renewable Lubricants via Self-condensation of Methyl ketones," Green Chem., vol. 18, No. 12 (2016), pp. S1-S16.
Extended European Search Report for European Application No. 18 845 941.6, dated May 3, 2021, 18 pages.
Balakrishnan et al., "Novel Pathways for Fuels and Lubricants from Biomass Optimized using Life-Cycle Greenhouse Gas Assessment," Proc. Natl. Acad. Sci., USA, 112(25):7645-7649 (2015).
Brown et al., "The Condensation of Furan and Sylvan with Some Carbonyl Compounds," Canadian Journal of Chemistry, 34(9):1147-1153 (1956).
Dutta et al., "Solventless C—C Coupling of Low Carbon Furanics to High Carbon Fuel Precursors Using an Improved Graphene Oxide Carbocatalyst," ACS Catal., 7:3905-3915 (2017).
Jadhav et al., "Production of Biomass-Based Automotive Lubricants by Reductive Etherification," ChemSusChem 10:2527-2533 (2017).
Oh et al., "Synthesis of Biolubricants Using Sulfated Zirconia Catalysts," Applied Catalysis A: General 455:164-171 (2013).
Park et al., "Tunable Oleo-Furan Surfactants by Acylation of Renewable Furans," ACS Cent. Sci. 2:820-824 (2016).
Pubchem CID 44413253, create date, Nov. 19, 2009, pp. 1-13, https://pubchem.ncbi.nlm.nih.gov/compound/44413253.
Pubchem CID 72724341, create date, Feb. 10, 2014, pp. 1-10, https://pubchem.ncbi.nlm.nih.gov/compound/72724341.
Pubchem CID 124198904, create date, Feb. 18, 2017, pp. 1-11, https://pubchem.ncbi.nlm.nih.gov/compound/124198904.
Salimon et al., "Biolubricants: Raw Materials, Chemical Modifications and Environmental Benefits," European Journal of Lipid Science and Technology 112(5):519-530 (2010).
Sun et al., "K2CO3-loaded Hydrotalcite: A Promising Heterogeneous Solid Base Catalyst for Biolubricant Base Oil Production from Waste Cooking Oils," Applied Catalysis B: Environmental 209:118-127 (2017).
International Preliminary Report on Patentability for International Application No. PCT/US2018/046965, dated Feb. 18, 2020, 10 pages.
International Search Report and Written Opinion for International Application PCT/US2018/046965, dated Oct. 22, 2018, 13 pages.
Balakrishnan et al., "Production of Renewable Lubricants Via Self-Condensation of Methyl Ketones," Green Chem., 18:3577-3581 (2016).
Gu et al., "Synthesis of Renewable Lubricant Alkanes from Biomass-Derived Platform Chemicals", ChemSusChem 10:4102-4108 (2017).
Gunanathan et al., "Applications of Acceptorless Dehydrogenation and Related Transformations in Chemical Synthesis," Science, 341(6143):1229712 (2013).
Ji et al, "Preparation of a Water-Based Lubricant from Lignocellulosic Biomass and Its Tribological Properties," Ind. Eng. Chem. Res., 56:7858-7864 (2017).
Ji et al., "Synthesis of Levulinic Acid-Based Polyol Ester and its Influence on Tribological Behavior as a Potential Lubricant," RSC Adv., 5:100443-100461 (2016).
Jones et al., "Implications of Transition State Confinement within Small Voids for Acid Catalysis," J. Phys. Chem. C, 118:17787-17800 (2014).
Karam et al., "High Catalytic Performance of Aquivion PFSA, a Reusable Solid Perfluorosulfonic Acid Polymer, in the Biphasic Glycosylation of Glucose with Fatty Alcohols," ACS Catal., 7:2990-2997 (2017).
Kioupis et al., "Impact of Molecular Architecture on the High-Pressure Rheology of Hydrocarbon Fluids," J. Phys, Chem. B, 104:7774-7783 (2000).
Lange et al., "Furfural—A Promising Platform for Lignocellulosic Biofuels," ChemSusChem, 5:150-166 (2012).
Liu et al., "Catalytic Hydrodeoxygenation of High Carbon Furylmethanes to Renewable Jet-Fuel Ranged Alkanes over a Rhenium-Modified Iridium Catalyst," ChemSusChem, 10:3225-3234 (2017).
Nakagawa et al., "Catalytic Reduction of Biomass-Derived Furanic Compounds with Hydrogen," ACS Catal., 3:2655-2666 (2013).
Pérez et al., "Ion Exchange Resins as Catalysts for the Liquid-Phase Dehydration of 1-Butanol to di-n-Butyl Ether," Appl. Catal. A: Gen., 482:38-48 (2014).
Weingarten et al., "Design of Solid Acid Catalysts for Aqueous-Phase Dehydration of Carbohydrates: The Role of Lewis and Brønsted Acid Sites," J. Catal., 279:174-182 (2011).
Yokoyama et al., "Hydrogenation of Carboxylic Acids to the Corresponding Aldehydes," Appl. Catal. A: Gen., 221:227-239 (2001).
Whitmore et al., "Higher Hydrocarbons. I. Seven Alkyl Substituted Docosanes", Journal of the American Chemical Society, Jun. 1, 1942, vol. 64(6), pp. 1360-1364, XP93034960.
Wilner et al., "Vaccine Potentiation by Emulsification with Pure Hydrocarbon Compounds", The Journal of Immunology, Aug. 1, 1963, vol. 91(2), pp. 210-229, XP093044655.
Nederbragt et al., "Viscosity Data and Relations of Normal and Iso-paraffins", Physica, Aug. 1, 1947, vol. 13(6-7), pp. 305-318, XP024737555, [retrieved on Aug. 1, 1947].
Cui et al., "Constituent Compounds of Floral Odor in Panisea Cavaleriei", Chemistry of Natural Compounds, Nov. 20, 2017, vol. 53(6), pp. 1182-1183, XP036381033, [retrieved on Nov. 20, 2017].
Cohen et al., "Aliphatic Esters: Properties and Lubricant Applications", Industrial and Engineering Chemistry, Jan. 1, 1953, vol. 45(8), pp. 1766-1775, XP002487117.
Fazullin et al., "Investigation of the Properties and Composition of a Concentrate of Spent Inkam-1 Emulsion as a Corrosion Inhibitor", Petroleum Chemistry, Jul. 22, 2017, vol. 57(8), pp. 728-733, XP036282117, [retrieved on Jul. 22, 2017].
Challenger et al., "The Synthesis and Properties of Tertiary Methanes", Journal of the Institute of Petroleum, Feb. 1954, vol. 40(362), pp. 37-44, XP093044669.
European Communication pursuant to Article 94(3) EPC for European Application No. 18 845 941.6. dated May 11, 2023, 11 pages.

* cited by examiner

FURAN BASED COMPOSITIONS AND METHODS OF MAKING THEREOF

CROSS REFERENCE TO RELATED APPLICATIONS

This application is a national stage application under 35 U.S.C. § 371 of International Application No. PCT/US2018/046965, filed Aug. 17, 2018, which claims priority to U.S. Provisional Patent Application No. 62/546,603, filed Aug. 17, 2017, the disclosures of each of these applications being is incorporated herein by reference in their entireties for all purposes.

STATEMENT REGARDING FEDERALLY SPONSORED RESEARCH

This invention was made with support from the government under DOE Grant No. DE-SC0001004 awarded by the Department of Energy. The government has certain rights in the inventions recited herein.

FIELD OF THE INVENTION

The present invention relates to lubricant compositions and in particular to bio-based compounds for use in lubricant compositions and base oils for pharmaceutical and personal care product formulations, and methods of making such compounds.

BACKGROUND OF THE INVENTION

Lubricants are widely used in industrial machinery, automobiles, aviation machinery, refrigeration compressors, agricultural equipment, marine vessels and many other applications and represent an over $60 billion global chemical enterprise.

Base oils are key components (typically, 75-90 wt %) of commercial formulated lubricants and account for up to 75% of lubricant cost. Base oils are also key components in the formulations of personal care products, greases, and the like. The majority of current lubricant base oils are petroleum-based mineral oils comprising a mixture of $C_{20}$~$C_{50}$ hydrocarbons, which are formulated with different additives (antioxidants, viscosity index improvers, pour point depressants, corrosion inhibitors, anti-wear reagents and others) to achieve desired specifications for different applications. These lubricants thicken quickly because of the high volatility of low molecular weight hydrocarbons, requiring their frequent replacement and generating waste. Better specifications can be achieved by using synthetic base oils, such as poly-α-olefins (PAOs), alkylbenzenes, polyalkylenes, synthetic esters, and the like. However, selectively tuning their molecular size and architecture is challenging. For example, cationic oligomerization of linear α-olefins ($C_8$-$C_{12}$ olefins) using homogeneous acid catalysts ($BF_3$, HF, or $AlCl_3$) results in uncontrolled oligomerization and formation of several products in PAOs, which may necessitate their expensive separations upon hydrogenation. In addition, the homogeneous acidic catalysts make the product corrosive and the process environmentally unfriendly. Thus, the production of high-performance lubricants from sustainable feedstocks is desirable.

The United States Department of Agriculture (USDA) has recently launched bio-preferred programs to enhance the utilization of lubricants that contain more than 25% renewable components. Thus, synthesis of bio-lubricants from fatty acids and triglycerides via esterification/transesterification, acyloxylation, epoxidation, hydrogenation, hydroformylation, alkylation and acylation, and the ene-reaction have gained momentum. High catalyst consumption, poor economics, and lack of effective heterogeneous catalysts for some processes (e.g., for hydroformylation) are common drawbacks. Importantly, chemical modification of fatty acids or triglycerides to products with tailored molecular architecture is a challenge, which limits the specifications of bio-lubricants and their applications. Thus, innovative approaches to synthesize bio-lubricant base oils with better and tunable properties are necessary for different targeted applications.

The C—C coupling of furans is a recently exploited reaction strategy for increasing carbon chain length to produce diesel and jet fuels, but its adaptation to produce bio-lubricant base-oils is still in infancy. Alkyl methyl ketones or furyl methyl ketones were recently upgraded to lubricant-range molecules via aldol condensation and hydrogenation or hydrodeoxygenation (HDO). (References 1,2) $C_{23}$ branched alkanes with 50% yield have been produced via aldol condensation, hydrogenation, and hydrodeoxygenation (Reference 3). Ether- and ester-based lubricants, using biomass-derived alcohol or levulinic acid, have also been reported (References 4-7). Despite progress, significant challenges remain, e.g., high amounts of catalyst used, inability to synthesize PAO molecules with controlled architecture and high selectivity, and separation of the homogeneous catalysts from the product.

SUMMARY OF THE INVENTION

Accordingly, an object of the present invention is to provide novel strategies to produce lubricant base oils with tailored molecular architecture, tunable properties and content. In particular, the lubricant base oils disclosed herein will contain one or more furan rings and/or branched hydrocarbon chains. The furan rings of the present disclosure may be fully saturated saturated (no carbon-carbon double bond in the furan ring, i.e., a tetrahydrofuran ring), partially saturated saturated (one carbon-carbon double bond in the furan ring, i.e., a dihydrofuran ring), or unsaturated (two carbon-carbon double bonds in the furan ring). In general, the lubricant base oils with tailored molecular architecture and content are produced from reacting 2-alkylfurans with one or more aldehyde, dialdehydes, enals and/or ketones. In a preferred embodiment, at least one of the 2-alkylfuran, aldehyde, enal, and/or ketone is obtained from a renewable carbon source (e.g., non-food biomass, natural oils and/or waste cooking oils (WCO) and/or fatty acid from vegetable oils or animal fat).

Three sets of products with unique structures, hereto referred as condensed furan (CF), condensed saturated furan (CSF) and condensed furan alkane (CFA) (FIG. 1A) with excellent yields and selectivity were obtained via hydroxyalkylation/alkylation (HAA), hydrogenation and hydrodeoxygenation (HDO) reactions, respectively. The use of alkylfurans and aldehydes (and/or dialdehydes and/or enals and/or ketones) of varying carbon length and branching enables the synthesis of lubricant base oils of different molecular sizes, structures, contents, branching and distance between branches. This enables unprecedented flexibility to tune lubricant specifications for a wide range of applications that are currently achieved by complex and careful formulation of mineral and synthetic base oils with chemical additives. This also enables the application of molecule simulation to predict the properties of lubricant base oils, in terms of viscosity and viscosity index, and direct the design and synthesis of new lubricant based oils with desirable properties.

Thus, in an aspect of the invention, a compound having the following formula is provided:

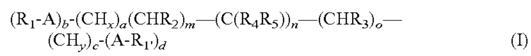

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6, wherein each A is independently an unsaturated furan ring, a partially saturated furan ring or a saturated furan ring, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62.

In an embodiment of the compound of formula (I), both $R_4$ and $R_5$ may be hydrogen.

In another aspect of the invention, a lubricant composition is provided, the lubricant composition comprising:

a. 75-99% by weight of a base oil comprising one or more compounds having the following formula:

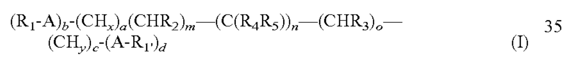

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or —$(CH_2)_4$—, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, wherein the total carbon content of the compound of formula (I) is in the range of 20 to 62; and b. an effective amount of one or more lubricant additives.

In an embodiment of the lubricant composition, both $R_4$ and $R_5$ may be hydrogen.

In yet another aspect, the lubricant composition as disclosed herein, is used in one or more of industrial machinery, automobiles, aviation machinery, refrigeration compressors, agricultural equipment, marine vessels, agriculture equipment, medical equipment, hydropower production machinery, and food processing equipment.

In another aspect, the lubricant base oil comprising one or more compounds of formula (I) of the present disclosure, is used in one or more of industrial machinery, automobiles, aviation machinery, refrigeration compressors, agricultural equipment, marine vessels, agriculture equipment, medical equipment, hydropower production machinery, and food processing equipment.

In a further aspect, there is a method of making a compound having the following formula:

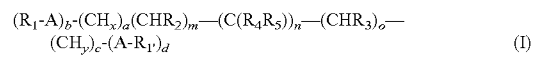

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or —$(CH_2)_4$—, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62, wherein the method comprises the steps of:

a) providing a first component comprising one or more of a 2-alkylfuran having the formula $R_1$-A and/or $R_1$'-A wherein $R_1$, $R_{1'}$, are independently selected from the group consisting of H and alkyl groups having 1 to 18 carbon atoms and A is a furan ring and a second component comprising one or more of:

i) an aldehyde having the formula $R_4R_5CO$, wherein at least one of $R_4$ or $R_5$ is hydrogen and at most one of $R_4$ or $R_5$ is an alkyl group having 1 to 18 carbon atoms, ii) a dialdehyde having the formula $(CR_4R_5)_n(CHO)_2$, wherein each $R_4$ and $R_5$ is independently selected from the group consisting of H and alkyl groups having 1 to 18 carbon atoms and n is an integer of 1-8, iii) an enal having the formula $CHR_2{=}CR_3{—}CHO$, wherein $R_2$ and $R_3$ are independently selected from the group consisting of H and alkyl groups having 1 to 18 or 2 to 8 carbon atoms, and iv) a ketone having the formula $R_4R_5CO$, wherein each $R_4$ and $R_5$ is independently selected from the group consisting of alkyl groups having 1 to 18 carbon atoms, wherein at least one of the first component and the second component is bio-derived from a renewable source;

b) condensing the first component with the second component in the presence of an acidic catalyst to form a condensed furan compound (CF);

c) optionally hydrogenating the condensed furan compound in the presence of a hydrogenation catalyst to obtain a condensed saturated furan compound (CSF); and d) optionally hydrodeoxygenating the condensed furan compound or the condensed saturated furan compound in the presence of a hydrodeoxygenation catalyst to obtain a condensed furan alkane compound (CFA).

In an embodiment of the method of making a compound of formula (I), both $R_4$ and $R_5$ may be hydrogen.

In an embodiment of the method, the compound having the formula (I), prepared according to the method of the present disclosure, is used as a base oil in pharmaceutical and personal care products.

In another aspect of the invention, a personal care composition is provided, the personal care composition comprising:

a. a base oil comprising one or more compounds having the following formula and derivatives thereof:

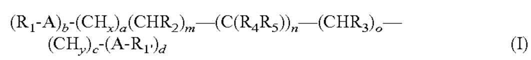

$$(R_1\text{-}A)_b\text{-}(CH_x)_a(CHR_2)_m—(C(R_4R_5))_n—(CHR_3)_o—(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, wherein the total carbon content of the compound of formula (I) is in the range of 20 to 62; and b. an effective amount of one or more additives selected from the group consisting of pigment, fragrance, emulsifier, wetting agent, thickener, emollient, rheology modifier, viscosity modifier, gelling agent, antiperspirant agent, deodorant active, fatty acid salt, film former, anti-oxidant, humectant, opacifier, monohydric alcohol, polyhydric alcohol, fatty alcohol, preservative, pH modifier, a moisturizer, skin conditioner, stabilizing agent, proteins, skin lightening agents, topical exfoliants, antioxidants, retinoids, refractive index enhancer, photo-stability enhancer, SPF improver, UV blocker, and water.

In an embodiment of the personal care composition of the present invention, the personal care composition further comprises an active ingredient selected from the group consisting of antibiotic, antiseptic, antifungal, corticosteroid, and anti-acne agent.

In another aspect of the invention, a pharmaceutical composition is provided, the pharmaceutical composition comprising:

a. a base oil comprising one or more compounds having the following formula (I) and derivatives thereof:

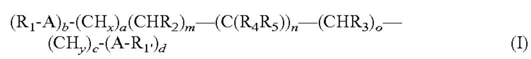

$$(R_1\text{-}A)_b\text{-}(CH_x)_a(CHR_2)_m—(C(R_4R_5))_n—(CHR_3)_o—(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, wherein the total carbon content of the compound of formula (I) is in the range of 20 to 62;

b. an effective amount of one or more pharmaceutically active ingredients; and c. optionally, one or more pharmaceutically active excipients (other than base oils comprising one or more compounds in accordance with formula (I)).

BRIEF DESCRIPTION OF THE DRAWINGS

The accompanying drawings, which are incorporated in and constitute a part of this specification, illustrate one (several) embodiment(s) of the invention, and together with the written description, serve to explain certain principles of the invention.

DETAILED DESCRIPTION OF THE INVENTION

Figure 1A:
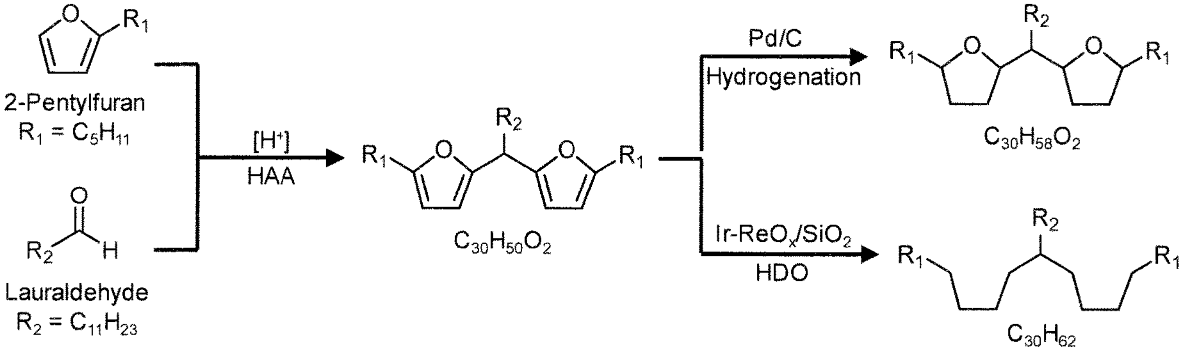
FIG. 1A shows versatile approaches to making compounds of formula (I) for use as base oils for lubricants and for use in other applications such as personal care products, according to various embodiments of the present invention. As shown, hydroxylalkylation/alkylation (HAA) of biomass derived 2-alkylfuran with aldehyde produces condensed furan compounds (CF), which upon hydrogenation over Pd/C gives CSF compounds. Furthermore, hydrodeoxygenation (HDO) of CF over Ir-$ReO_x/SiO_2$ produces CFA compounds.

As used herein, the term "biomass-derived" is used interchangeably with "biologically-derived", "bio-derived" or "bio-based" and refers to compounds that are obtained from renewable resources such as plants and contain either only or substantially renewable carbon, and no or a very minimal amount fossil fuel-based or petroleum-based carbon.

Assessment of the renewably based carbon in a material can be performed through standard test methods. Using radiocarbon and isotope ratio mass spectrometry analysis, the bio-based content of materials can be determined, using ASTM-D6866 a standard method established by ASTM International, formally known as the American Society for Testing and Materials.

As used herein, the "bio-based content" is determined in accordance with ASTM-D6866 and is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon) with modern or present defined as 1950. If the material being analyzed is a mixture of present day radiocarbon and fossil carbon (containing no radiocarbon), then the pMC value obtained correlates directly to the amount of biomass material present in the sample.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day plant/tree would give a radiocarbon signature near 107.5 pMC. If that material was diluted with 50% petroleum derivatives, it would give a radiocarbon signature near 54 pMC.

A bio-mass content result is derived by assigning 100% equal to 107.5 pMC and 0% equal to 0 pMC. In this regard, a sample measuring 99 pMC will give an equivalent bio-based content result of 93%.

Assessment of the biodegadability of a material, such as of compounds of formula (I), base oils, or compositions such as lubricant compositions and personal care compositions of the present disclosure, can be performed through standard test methods, such as those developed by the Organization for Economic Cooperation and Development (OECD), the Coordinating European Council (CEC), and the American Society for Testing and Materials (ASTM), such as, OECD 301B (the Modified Strum test), ASTM D-5864, and CEC L-33-A-934. Both OECD 301B and ASTM D-5864 measure ready biodegradability, defined as the conversion of 60% of the material to $CO_2$ within a ten day window following the onset of biodegradation, which must occur within 28 days of test initiation. In contrast, the CEC method tests the overall biodegradability of hydrocarbon compounds and requires 80% or greater biodegradability as measured by the infrared absorbance of extractable lipophilic compounds.

As used herein, the terms "lubricant", "lubricant composition", and "lubricant base oil" refer to any substance used to reduce friction by providing a protective film between two moving surfaces. In general, a lubricant exhibits one or more characteristics, such as, high viscosity index, high boiling point, thermal stability, oxidation stability, low pour point, corrosion prevention capability and low surface tension.

As used herein, a "condensation" reaction refers to a chemical reaction in which two molecules combine to form larger molecule while producing a small molecule, such as $H_2O$, as a byproduct.

As used herein, a "hydrogenation" reaction refers to a chemical reaction between molecular hydrogen and another compound, typically, in the presence of a catalyst to reduce or saturate organic compounds.

As used herein, a "hydrodeoxygenation" or "HDO" reaction refers to a chemical reaction whereby a carbon-oxygen single bond is cleaved or undergoes lysis (cleavage of a C—O bond) by hydrogen, typically in the presence of a catalyst. "HDO" is a process for removing oxygen from a compound.

The term "kinematic viscosity" is used herein to refer to a fluid's inherent resistance to flow when no external force other than gravity is acting on the fluid. "Kinematic viscosity" is measured as the ratio of absolute (or dynamic) viscosity to density.

The term "pour point" as used herein refers to the temperature below which a liquid loses its flow characteristics.

The term "saturated" as used herein refers to an organic molecule containing the greatest number of hydrogen atoms and no carbon-carbon double or triple bonds.

A "saturated" furan ring refers to a furan ring (a five membered ring containing four carbon atoms and an oxygen atom) with the greatest number of carbon-carbon single bonds, e.g., tetrahydrofuran. An "unsaturated" furan ring refers to a furan ring with the maximum number of carbon-carbon double bonds, and is interchangeably used herein with "condensed furan". A "partially saturated" furan ring contains at least one carbon-carbon double bond but contains less than the maximum number of carbon-carbon double bonds, e.g., dihydrofuran.

Process of Making a Compound Represented by Formula (I)

The invention disclosed herein include processes for the preparation of a compound as represented by the formula (I) from one or more bio-derived reactants, the compounds of formula (I), and their use as base oils in lubricant compositions. In an embodiment, the compounds of formula (I) is a condensed furan (CF) compound, a condensed partially saturated furan (CPSF) compound, a condensed saturated furan (CSF) compound, or a condensed furan alkane (CFA) compound.

In an aspect of the invention, the compound is represented by the following formula:

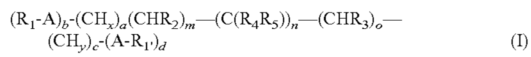

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

where:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6, In one embodiment, each A is independently a saturated furan ring, a partially saturated furan ring, an unsaturated furan ring, or —$(CH_2)_4$—. In another embodiment, each A is independently a saturated furan ring, an unsaturated furan ring, or —$(CH_2)_4$—. In yet another embodiment, each A is independently a saturated furan ring, a partially saturated furan ring, or an unsaturated furan ring. In some embodiment, each A is independently a saturated furan ring, or an unsaturated furan ring.

In the compound of formula (I), $R_1$, $R_{1'}$, $R_2$, $R_3$, $R_4$ and $R_5$ can be independently chosen from among H (hydrogen) and alkyl groups having 1 to 18 carbon atoms, such that at least one of $R_2$, $R_3$, $R_4$, and $R_5$ is not H (hydrogen), and the total carbon content of the compound of formula (I) is in the range of 20 to 62 (meaning that the compound contains a total of from 20 to 62 carbon atoms). In an embodiment, both $R_4$ and $R_5$ of compounds of formula (I) may be H.

As used herein the alkyl groups can be substituted or unsubstituted, cyclic or acyclic, or branched or unbranched or a combination thereof. Suitable examples of alkyl groups include, but are not limited to, butyl, pentyl, hexyl, heptyl, octyl, dodecyl, octadecanyl, cyclopentyl, and cyclohexyl.

In an embodiment, $R_1$ and $R_{1'}$ may be the same. In another embodiment, R and $R_{1'}$ may be different. In yet another embodiment, $R_1$, $R_{1'}$ are independently chosen from branched alkyl groups having 3-18 carbon atoms, preferably from acyclic branched alkyl groups having 3-11 carbon atoms, and most preferably from acyclic branched alkyl groups having 4-8 carbon atoms, provided that in total the compound contains from 20 to 62 carbon atoms.

In yet another embodiment, $R_1$ and $R_{1'}$ may have the formula: —$(CHR_6)$—$CH_2R_7$). In such embodiments, $R_6$ and $R_7$ can be independently H or a linear or branched alkyl group having 2 to 18 carbon atoms, preferably a branched alkyl group having 2-11 carbon atoms, and most preferably an acyclic branched alkyl group having 3-11 carbon atoms, provided that in total the compound contains from 20 to 62 carbon atoms. Suitable examples of $R_6$, $R_7$ include, but are not limited to, methyl, butyl, hexyl, dodecyl, cyclopentyl, and cyclohexyl.

Suitable examples of $R_1$, $R_{1'}$ include, but are not limited to, butyl, pentyl, hexyl, heptyl, octyl, dodecyl, octadecanyl, cyclopentyl, and cyclohexyl.

In an embodiment, one of $R_2$ and $R_3$ is hydrogen. In another embodiment, both $R_2$ and $R_3$ are hydrogen. In yet another embodiment, $R_2$ and $R_3$ may be independently chosen from among branched alkyl groups having 1-9 carbon atoms, preferably 1-8 carbon atoms, and most preferably 1-6 carbon atoms, provided that in total the compound contains from 20 to 62 carbon atoms. Suitable examples of $R_2$ and $R_3$ include, but are not limited to, methyl, butyl, hexyl, dodecyl, cyclopentyl, and cyclohexyl.

In one embodiment, one of $R_4$ and $R_5$ is hydrogen. In another embodiment, both $R_4$ and $R_5$ are hydrogen. In yet another embodiment, at least one of $R_4$ and $R_5$ is an alkyl chain having 2-8 carbon atoms, preferably 2-6 carbon atoms, and most preferably 4-6 carbon atoms, provided that in total the compound contains 20 to 62 carbon atoms.

In an embodiment, at least one of $R_1$, $R_{1'}$, $R_2$, $R_3$, $R_4$ and $R_5$ is a branched alkyl group, having one or more branches. The one or more branches can have any suitable number of carbon atoms, with at least one of the branches having 1-18 carbon atoms, and preferably 1-10 carbon atoms. The branched alkyl group may, for example, contain a total of 3-18 carbon atoms or 3-11 carbon atoms.

Suitable examples of branched alkyl groups, having one or more branches include, but are not limited to, methylpropyl, methylbutyl, methyldodecyl, ethylpropyl, ethyloctyl, and cyclopentyheptyl.

In an aspect, the compound of formula (I) has one of the following structures:

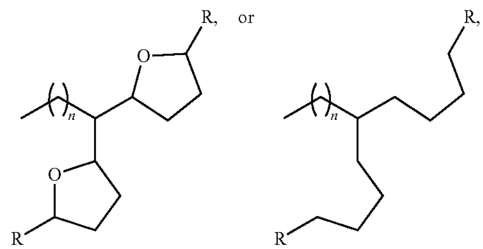

where n is 0 to 17 and R is $R_1$ or $R_{1'}$, as defined hereinabove, provided that in total the compound contains 20 to 62 carbon atoms.

In another aspect, the compound of formula (I) has one of the following structures:

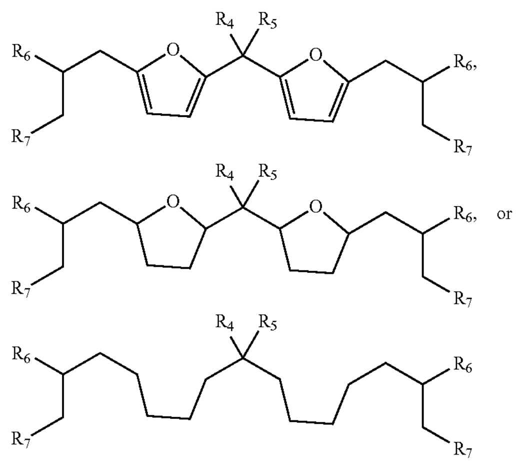

where $R_6$ and $R_7$ may be independently chosen from among hydrogen or a substituted or an unsubstituted, a cyclic or an acyclic, a branched or an unbranched alkyl group having 1 to 18 carbon atoms, preferably 2-12 carbon atoms, and most preferably 4-10 carbon atoms, provided that in total the compound contains from 20 to 62 carbon atoms.

In one embodiment, the compound of formula (I) is a condensed furan compound (CF). In another embodiment, the compound of formula (I) is a condensed furan alkane compound (CFA). In yet another embodiment, the compound of formula (I) is a condensed saturated furan compound (CSF). In another embodiment, the compound of formula (I) is a condensed partially saturated furan compound (CPSF) or a mixture of one or more of CFA, CSF, and CPSF.

Exemplary CF compounds include, but are not limited to, 5,5-(ethane-11-dlyl)bis(2-pentylfuran), 5,5'-(dodecane-1,1-diyl)bis(2-methylfuran), 5,5'-(dodecane-1,1-diyl)bis(2-ethylfuran), 5,5'-(hexane-1,1-diyl)bis(2-pentylfuran), 5,5'-(dodecane-1,1-diyl)bis(2-propylfuran), 5,5'-(octane-1,1-diyl)bis(2-pentylfuran), 5,5'-(2-ethylhexane-1,1-diyl)bis(2-pentylfuran), 5,5'-(dodecane-1,1-diyl)bis(2-butylfuran), 5,5'-(decane-1,1-diyl)bis(2-pentylfuran), 5,5'-(2-ethylhexane-1,1-diyl)bis(2-hexylfuran), 5,5'-(dodecane-1,1-diyl)bis(2-pentylfuran), 5,5'-(2-ethylhexane-1,1-diyl)bis(2-heptylfuran), 5,5'-(dodecane-1,1-diyl)bis(2-hexylfuran), 5,5'-(dodecane-1,1-diyl)bis(2-heptylfuran), 5,5',5"-(butane-1,1,3-triyl)tris(2-pentylfuran), 5,5'-(undecane-2,2-diyl)bis(2-pentylfuran), and 1,1,6,6-tetrakis(5-methylfuran-2-yl)hexane Exemplary CFA compounds include, but are not limited to, 10-methylnonadecane, 6-pentylheptadecane, 7-hexyloctadecane, 10-pentylnonadecane, 8-heptylnonadecane, 10-heptylnonadecane, 10-(heptan-3-yl)nonadecane, 9-octylicosane, 10-nonylnonadecane, 11-(heptan-3-yl)henicosane, 10-nonylhenicosane, 12-(heptan-3-yl)tricosane, 11-decyldocosane, 12-undecyltricosane, 10-methyl-12-nonylhenicosane, 10-methyl-10-nonylnonadecane, and 6,11-dipentylhexadecane.

Exemplary CSF compounds include, but are not limited to, 5,5'-(dodecane-1,1-diyl)bis(2-pentyltetrahydrofuran), 5,5'-(dodecane-1,1-diyl)bis(2-butylltetrahydrofuran), 5,5'-(dodecane-1,1-diyl)bis(2-propyltetrahydrofuran), 5,5'-(dodecane-1,1-diyl)bis(2-ethyltetrahydrofuran), 5,5'-(dodecane-1,1-diyl)bis(2-methyltetrahydrofuran), 5,5'-(dodecane-1,1-diyl)bis(2-heptyltetrahydrofuran), 5,5'-(2-ethylhexane-1,1-diyl)bis(2-pentyltetrahydrofuran), 5,5'-(ethane-1,1-diyl)bis(2-pentyltetrahydrofuran), 5,5'-(2-ethylhexane-1,1-diyl)bis(2-heptyltetrahydrofuran), 5,5'-(2-ethylhexane-1,1-diyl)bis(2-hexyltetrahydrofuran), 5,5'-(octane-1,1-diyl)bis(2-pentyltetrahydrofuran), 5,5'-(decane-1,1-diyl)bis(2-pentyltetrahydrofuran), 5,5'-(hexane-1,1-diyl)bis(2-pentyltetrahydrofuran), and 1-((2S)-5-methyltetrahydrofuran-2-yl)-1,6,6-tris(5-methyltetrahydrofuran-2-yl)hexane.

Referring back to the process of making a compound as represented by formula (I), the process includes providing one or more of an aldehyde, a dialdehyde, an enal or a ketone and one or more 2-alkylfurans, where at least one of the 2-alkylfuran, the aldehyde, the dialdehyde, the enal or the ketone is bio-derived from a renewable source.

Any suitable aldehyde ($R_4R_5CO$), dialdehyde ($(CR_4R_5)_n(CHO)_2$), enal ($CHR_2{=}CR_3{-}CHO$), or ketone ($R_4R_5CO$) may be used. In the aldehyde ($R_4R_5CO$), at least one of $R_4$ or $R_5$ is hydrogen and at most one of $R_4$ or $R_5$ is an alkyl group having 1 to 18 carbon atoms or 2 to 8 carbon atoms. In the dialdehyde $(CR_4R_5)_n(CHO)_2$, each $R_4$ and $R_5$ may be independently selected from the group consisting of H and alkyl groups having 1 to 18 carbon atoms or 2 to 8 carbon atoms, with n being an integer of 2-8. In the enal ($CHR_2{=}CR_3{-}CHO$), $R_2$ and $R_3$ independently may be H or an alkyl group having 1 to 18 or 2 to 8 carbon atoms. In the ketone ($R_4R_5CO$), $R_4$ and $R_5$ may be independently selected from the group consisting of alkyl groups having 1 to 8 carbon atoms. Any suitable one or more 2-alkylfurans ($R_1$-A) &/or ($R_{1'}$-A) may be used, wherein $R_1$, $R_{1'}$, are as defined hereinabove and A is the furan ring.

In an embodiment, the step of providing an aldehyde includes at least one of dehydrogenating biomass derived alcohols and selective hydrogenation of fatty acids from natural oils or waste cooking oils. Suitable examples of biomass derived alcohols include, but are not limited to, ethanol, butanol, hexanol, and dodecanol. Such biomass derived alcohols may be derived from any suitable biomass including, but not limited to, corn grain, soya bean grain, any kind of hard wood, any kind of soft wood, and algae. Suitable examples of fatty acids include, but are not limited to lauric acid and steric acid. Such fatty acid may be derived from any suitable natural cooking oils including, but not limited, to coconut oil, palm oil, rapeseed oil, vegetable oil, corn oil, peanut oil, olive oil, canola oil, and sunflower oil. The fatty acids may also be derived from any waste cooking oils of one or more natural cooking oils and/or animal fats. The synthesis of aldehydes of different carbon length via dehydrogenation of biomass derived alcohols (Reference 8) or selective hydrogenation of fatty acids from natural oils or WCO (Reference 9) is known in the art.

In another embodiment, the step of providing an enal includes the step of dimerization of an aldehyde.

In an embodiment, the 2-alkylfuran (or a mixture of 2-alkylfurans) may be prepared by a process comprising dehydration and hydrodeoxygenation of C5 sugars of biomass such as corn grain, soya bean grain, any kind of hard wood, any kind of soft wood, algae and the like. In another embodiment, the 2-alkylfuran (or a mixture of 2-alkylfurans) may be prepared by a process comprising furan acylation with carboxylic acids or carboxylic acid anhydrides followed by hydrodeoxygenation of the acylated products. The synthesis of 2-alkylfurans of different carbon numbers via direct HDO of $C_5$ sugars of biomass (Reference 10), i.e., 2-methylfuran (2MF), or furan acylation with carboxylic acids (or their anhydrides) followed by HDO of the acylated products (Reference 11) (Scheme 1) is known in the art.

Scheme 1

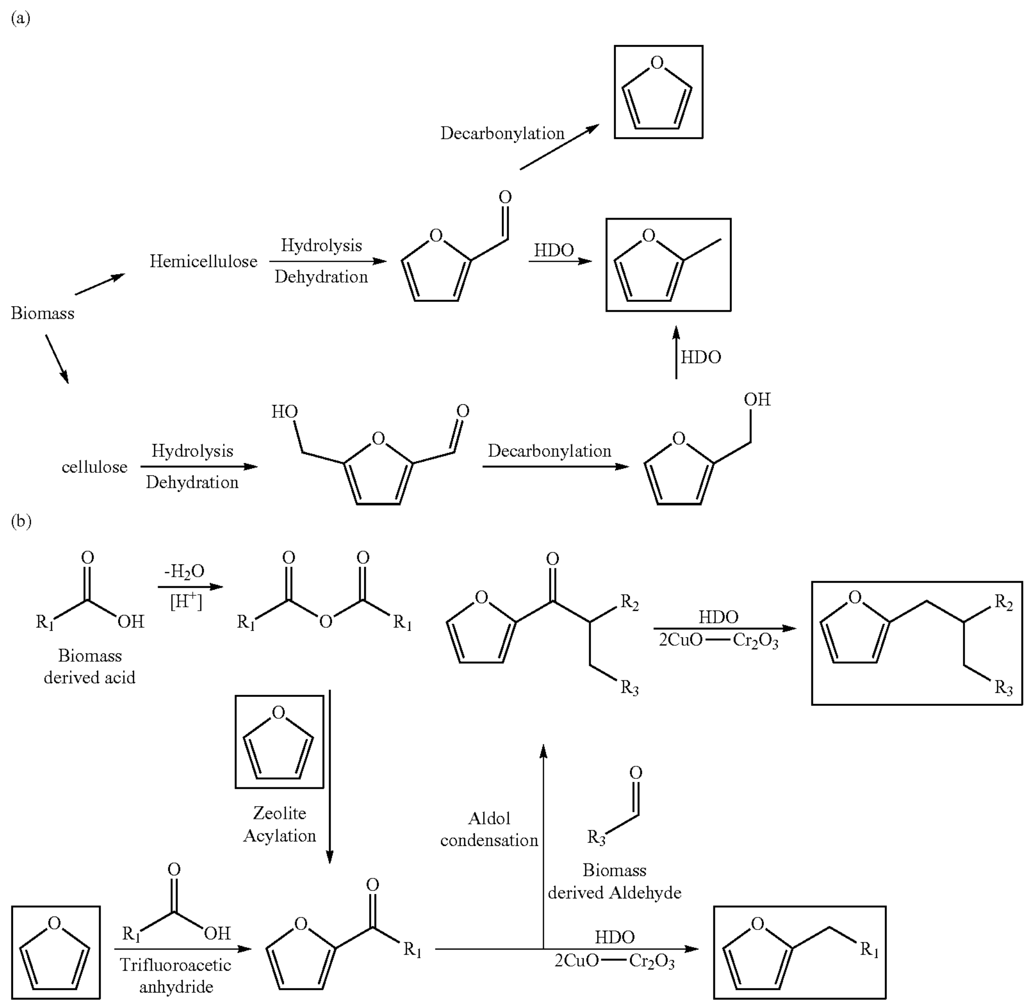

The process of making a compound of formula (I) further includes condensing a 2-alkylfuran with an aldehyde, a dialdehyde, an enal or a ketone optionally in the presence of an acidic catalyst to form a condensed furan compound (CF). In an embodiment, condensation is carried out in the presence of a thiol. Any suitable thiol compound can be used, including, but not limited to, ethanethiol, propanethiol, butanethiol or combinations thereof, and preferably the thiol compound is propanethiol.

The acidic catalyst can be, for example, any suitable liquid acid including inorganic liquid acids and organic liquid acids, or any suitable solid acid. Exemplary liquid acids include, but are not limited to, $H_2SO_4$, $CH_3SO_3H$, triflic acid, and p-toluenesulfonic acid. Exemplary solid acids include, but are not limited to, Amberlyst® resins (e.g. Amberlyst®-15, Amberlyst®-36), Nafion® resins (e.g., Nafion NR50), Aquivion® Resins (e.g., Aquivion® PW98, Aquivion® PW79S), Zeolites (e.g. ZSM-5, HBEA, HY), and silica supported $H_3PO_4$.

In an embodiment, the process of making a compound of formula (I) may also include hydrogenating the condensed furan compound in the presence of a hydrogenation catalyst to obtain a condensed saturated furan compound (CSF). Partial hydrogenation of the condensed furan compound may also be carried out, thereby forming a condensed partially saturated furan compound (containing one or more dihydrofuran rings).

Any suitable hydrogenation catalyst may be used such as a metal base catalyst chosen from palladium catalysts supported on carbon or acidic materials or a nickel based catalyst. Palladium catalysts are preferably Pd/C, $Pd/SiO_2$ and $Pd/Al_2O_3$, and Ni-based catalysts preferably are Raney Ni catalysts.

In another embodiment, the process of making a compound of formula (I) may further include hydrodeoxygenating the condensed furan compound or the condensed saturated furan compound in the presence of a hydrodeoxygenation catalyst to obtain a condensed furan alkane compound (CFA). Any suitable hydrodeoxygenation catalyst may be used, such as a solid acid supported metal based catalyst or a physical mixture of a metal based catalyst, preferably Pd/C, $Pd/SiO_2$ and Pt/C, with a solid acid. Suitable solid acid supported metal based catalysts includes, but are not limited to, Ni/ZSM-5, Pd/ZSM-5, Pd/BEA; a physical mixture of a metal based catalyst with a solid acid, which includes but is not limited to, Pd/C+ZSM-5, Pd/C+BEA, Pt/C+BEA, and preferably supported metal-metal oxide catalysts such as $Ir—ReO_x/SiO_2$, $Ir—MoO_x/SiO_2$ or $^1M^2MO/SiO_2$, where $^1M$ can be chosen from among Ir, Ru, Ni, Co, Pd, Pt, Rh and $^2M$ can be chosen from among Re, Mo, W, Nb, Mn, V, Ce, Cr, Zn, Co, Y, Al).

In an aspect of the invention, the compound of formula (I) is a condensed furan compound (CF), having a bio-based content in the range of 10 to 100%, e.g., at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%; preferably 30 to 100%; and most preferably 50 to 100%, as determined according to ASTM-D6866.

In another aspect of the invention, the compound of formula (I) is a condensed saturated furan compound (CSF), having a bio-based content in the range of 10 to 100%, e.g., at least 10%, at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%; preferably 30 to 100%; and most preferably 50 to 100%, as determined according to ASTM-D6866.

In yet another aspect, a lubricant composition includes 75-99% by weight of a base oil comprising one or more compounds of formula (I), in accordance with various embodiments of the present invention, as disclosed hereinabove, and an effective amount of one or more lubricant additives. According to various embodiments, one or more compounds of formula (I) may comprise at least 10%, at least 20%, at least 30%, at least 40%, at least 50%, at least 60%, at least $7^{o}\%$, at least 80%, at least 90%, at least 95%, at least 99% or even 100% by weight of the base oil.

In an embodiment of the lubricant composition, the base oil comprising at least one of the one or more compounds of formula (I) has a bio-based content in the range of 20 to 100%, e.g., at least 20%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100%; preferably 40 to 100%; and most preferably 50 to 100%, as determined according to ASTM-D6866.

In another embodiment of the lubricant composition, at least one of the one or more compounds of formula (I) has at least one unsaturated furan ring or at least one saturated furan ring, preferably a plurality of unsaturated furan rings or a plurality of saturated furan rings. It is also possible for at least one of the one or more compounds of formula (I) to contain at least one or a plurality of dihydrofuran rings (partially saturated furan rings). Thus, the base oil of the lubricant composition of the present disclosure includes a condensed furan compound (CF) and/or a condensed saturated furan compound (CSF). The one or more compounds present in the lubricant composition may further include a condensed saturated furan compound (CSF), in addition to a condensed furan compound (CF) and/or a condensed furan alkane compound (CFA).

In an embodiment of the lubricant composition, the one or more lubricant additives may be selected from among antioxidants, stabilizers, detergents, dispersants, demulsifiers, antioxidants, anti-wear additives, pour point depressants, viscosity index modifiers, friction modifiers, anti-foam additives, defoaming agents, corrosion inhibitors, wetting agents, rust inhibitors, copper passivators, metal deactivators, extreme pressure additives, and combinations thereof. Any of such lubricant additives may be used in an amount effective to impart one or more desired properties or characteristics to the lubricant composition. Typically, effective concentrations of such lubricant additives will be similar to those utilized in conventional lubricant compositions, although in certain cases lower or higher concentrations may be needed or desired due to the different characteristics of the base oils comprised of one or more compounds of formula (I) which are present in the lubricant compositions of the present invention. In certain cases, individual lubricant additives are included in the lubricant composition at only a few ppm, but in other cases an individual lubricant additive is employed in an amount of at least 10 ppm, at least 50 ppm, at least 100 ppm, at least 250 ppm, at least 500 ppm, at least 750 ppm, at least 1000 ppm, at least 2000 ppm, at least 3000 ppm, at least 4000 ppm, at least 5000 ppm, or even higher (e.g., at least 1% by weight), depending upon the type of lubricant additive and the effect desired to be achieved by the inclusion of the lubricant additive. Generally speaking, however, the total amount of lubricant additive does not exceed 25% by weight based on the total weight of the lubricant composition.

According to other embodiments, the lubricant composition comprises not more than 20%, not more than 15%, not more than 10% or not more than 5% by weight in total of lubricant additive(s), based on the total weight of the lubricant composition.

In another embodiment, the lubricant composition may further include one or more co-base oils (i.e., base oils other than the base oil comprised of one or more compounds of formula (I)). For example, the co-base oil may be selected from the group consisting of American Petroleum Institute (API) Group I base oil, Group II base oil, Group III base oil, Group IV base oil, Group V base oil, gas-to-liquid (GTL) base oil, and combinations thereof.

According to certain embodiments, the lubricant composition is comprised of a) from 75-99% by weight of a base oil comprised of one or more compounds of formula (I) and b) from 1-25% by weight in total of one or more additional components selected from the group consisting of lubricant additives and co-base oils, the total of a) and b) equaling 100%.

In yet another embodiment of the lubricant composition, at least one of the one or more compounds of formula (I) has a kinematic viscosity in the range of 2 to 100 Centistokes (CSt) at 100° C., preferably 2-50 CSt, most preferably 2-30 CSt and in the range of 6 to 100 CSt at 40° C., preferably 6-50 CSt, most preferably 6-30 CSt, as measured by ASTM D445, such that a viscosity index calculated from kinetic viscosity at 100° C. and 40° C., is in the range of 100 to 200, as measured by ASTM D2270, and the base oil has a kinematic viscosity of at least 3 CSt, as measured by ASTM D445.

In one embodiment of the lubricant composition, the at least one of the one or more compounds of formula (I) has a pour point in the range of −12° C. to −80° C., preferably −12° C. to −70° C., and most preferably −12° C. to −66° C., as measured by ASTM D97.

In certain embodiments of the lubricant composition, the at least one of the one or more compounds of formula (I) has an oxidation stability in the range of 170° C. to 300° C., preferably 170° C. to 280° C., and most preferably 170° C. to 250° C., as measured by ASTM D6375.

In an aspect of the invention, the lubricant composition may be used in one or more of industrial machinery, automobiles, aviation machinery, refrigeration compressors, agricultural equipment, marine vessels, agriculture equipment, medical equipment, hydropower production machinery, and/or food processing equipment.

In another aspect of the invention, the base oil comprising one or more compounds of formula (I), in accordance with various embodiments of the present invention, as disclosed hereinabove, may be used in one or more of industrial machinery, automobiles, aviation machinery, refrigeration compressors, agricultural equipment, marine vessels, agriculture equipment, medical equipment, hydropower production machinery, and/or food processing equipment. In another embodiment, the base oil comprising one or more compounds of formula (I), in accordance with various embodiments of the present invention, as disclosed hereinabove, may be used in pharmaceutical formulations and personal care product formulations, e,g, sunscreen, lotion, creams, cosmetics, and the like.

According to still further embodiments, a method is provided of reducing at least one of friction or wear between a first surface and a second surface, wherein the method comprises lubricating at least one of the first surface and the second surface with a base oil or a lubricant composition comprising at least one compound of formula (I) in accordance with the present invention. The first surface and the second surface may be the same as or different from each other and may be constructed of any suitable material, including for example metal, coated metal, plastic, and/or ceramic.

Also provided by the present invention is a method of lowering the coefficient of friction of a substrate surface, wherein the method comprises applying a coating of a base oil or lubricant composition comprised of at least one compound in accordance with formula (I) to the substrate surface. The substrate may be comprised of any suitable material such as metal, coated metal, plastic and/or ceramic.

In yet another aspect, a personal care composition is provided, the personal care composition including a base oil comprising one or more compounds of formula (I), in accordance with various embodiments of the present invention, as disclosed hereinabove, and an effective amount of one or more additives. Any suitable additive could be used, including, but not limited to, pigment, fragrance, emulsifier, wetting agent, thickener, emollient, rheology modifier, viscosity modifier, gelling agent, antiperspirant agent, deodorant active, fatty acid salt, film former, anti-oxidant, humectant, opacifier, monohydric alcohol, polyhydric alcohol, fatty alcohol, preservative, pH modifier, a moisturizer, skin conditioner, stabilizing agent, proteins, skin lightening agents, topical exfoliants, antioxidants, retinoids, refractive index enhancer, photo-stability enhancer, SPF improver, UV blocker, and water. In another embodiment, the personal care composition may further comprise an active ingredient selected from the group consisting of antibiotic, antiseptic, antifungal, corticosteroid, and anti-acne agent. The personal care composition of the present disclosure may be used in any suitable application including, but not limited to, cosmetics, sunscreens, lotions, creams, antiperspirants, deodorants, and medicated ointments, creams, and oils.

In still another aspect, a pharmaceutical composition is provided, the pharmaceutical composition including a base oil comprising one or more compounds of formula (I), in accordance with various embodiments of the present invention, as disclosed hereinabove, an effective amount of one or more pharmaceutically active ingredients, and, optionally, one or more excipients (other than base oils comprising one or more compounds of formula (I)). Any suitable pharmaceutically active ingredient(s) could be used, including in particular oil-soluble drugs, such as anti-inflammatory agents, antibiotics, antifungals, acne treatment agents, scabies/lice treatment agents, corticosteroids and analgesics. The pharmaceutical composition could, for example, take the form of a cream, lotion, foam, gel, ointment, emulsion (including both water-in-oil and oil-in-water emulsions) or paste and may be a topical preparation, oral formulation or injectable formulation. The base oil comprising one or more compounds of formula (I) may function, for example, as a carrier, vehicle, solubilizing excipient or filler (such as in soft gelatin capsules and the like).

Thus, the present invention provides a novel strategy to synthesize new and existing lubricant base oils with structural diversity and tunable properties using energy efficient C—C coupling and commonly used refinery methods without complex separations that are necessary for current petroleum-based base-oils. Non-food biomass and natural or waste cooking oils can be harnessed to obtain synthons (alkylfurans, aldehydes, dialdehydes, enals and ketones) of varying carbon length and branching, possessing versatile chemistry to provide opportunities to build base oils molecules of varying structural features and properties for a wide range of targeted applications. The use of efficient and easily separable heterogeneous catalysts, as opposed to corrosive homogeneous acid catalysts currently used for synthetic base oils synthesis, enables high products selectivity and yield (up to 95%). In addition, low temperature processing compared to the current refinery processing (cracking and distillation for synthetic and mineral base oils), and the use of sustainable feedstock with abundant supply and possible biodegradability could make this process and products competitive and adaptive to the existing market place. Unique properties for furan and tetrahydrofuran ring containing products (e.g., $C_{30}$-CF1, $C_{30}$-CSF1) are appealing for exploring their market potential and application segments. The branched alkane products, e.g. $C_{30}$-CFA1, with comparable or better properties, compared to current commercial mineral or synthetic base oils, have the potential to revolutionize out-of-box thinking for the synthesis of commercial relevant base-oils and replacement of current synthetic base-oils that have challenges associated with selectivity, separations, tuning molecular structures for desired properties etc. The properties can be predicted by molecular simulation to inform the design of molecules, an approach previously unavailable for petroleum-derived base oils that cannot be synthesized with molecular specificity.

Aspects of the Invention

Certain illustrative, non-limiting aspects of the invention may be summarized as follows:

Aspect 1: A compound having the following formula:

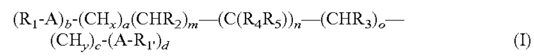

$$(R_1\text{-}A)_b\text{-}(CH_x)_a(CHR_2)_m—(C(R_4R_5))_n—(CHR_3)_o—(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6, wherein each A is independently an unsaturated furan ring, a partially saturated furan ring or a saturated furan ring, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62.

Aspect 2: The compound according to Aspect 1, wherein the compound has a bio-based content in the range of 20 to 100%, according to ASTM-D6866.

Aspect 3: The compound according to any of Aspects 1 or 2, wherein $R_1$, $R_{1'}$ are independently selected from branched alkyl groups having 3-18 carbon atoms or preferably from acyclic branched alkyl groups having 3-11 carbon atoms.

Aspect 4: The compound according to any of Aspects 1 or 2, wherein $R_1$ and $R_{1'}$ have the formula: $—(CHR_6)—CH2R_7$, wherein $R_6$ and $R_7$ are independently H or a linear or branched alkyl group having 2 to 18 carbon atoms, preferably branched alkyl group having 2-11 carbon atoms, and most preferably acyclic branched alkyl group having 3-11 carbon atoms.

Aspect 5: The compound according to any one of Aspects 1-4, wherein $R_2$ and $R_3$ are independently selected from the group consisting of branched alkyl groups having 4-9 carbon atoms.

Aspect 6: The compound according to any of Aspects 1-5, wherein both $R_4$ and $R_5$ are hydrogen.

Aspect 7: The compound according to any of Aspects 1-5, wherein at least one of $R_1$, $R_{1'}$, $R_2$, $R_3$, $R_4$ and $R_5$ is a branched alkyl group, having one or more branches with 1-4 carbon atoms each.

Aspect 8: The compound according to any of Aspects 1-5 having one of the following structures:

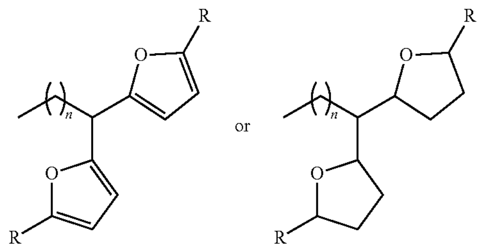

wherein n is 0 to 17, and wherein R is $R_1$ or $R_{1'}$, as defined in Aspect 1.

Aspect 9: The compound according to any of Aspects 1-3 having one of the following structures:

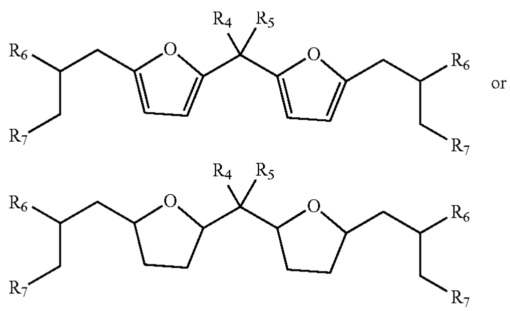

wherein $R_6$ and $R_7$ are independently selected from hydrogen or a substituted or an unsubstituted, a cyclic or an acyclic, a branched or an unbranched alkyl group having 1 to 18 carbon atoms.

Aspect 10: The compound according to any of Aspects 1, 2 or 3, selected from the group consisting of:

(i) condensed furan compounds (CFs): 5,5-(ethane-11-dlyl)bis(2-pentylfuran), 5,5'-(dodecane-1,1-diyl)bis(2-methylfuran), 5,5'-(dodecane-1,1-diyl)bis(2-ethylfuran), 5,5'-(hexane-1,1-diyl)bis(2-pentylfuran), 5,5'-(dodecane-1,1-diyl)bis(2-propylfuran), 5,5'-(octane-1,1-diyl)bis(2-pentylfuran), 5,5'-(2-ethylhexane-1,1-diyl)bis(2-pentylfuran), 5,5'-(dodecane-1,1-diyl)bis(2-butylfuran), 5,5'-(decane-1,1-diyl)bis(2-pentylfuran), 5,5' -(2-ethylhexane-1,1-diyl)bis(2-hexylfuran), 5,5'-(dodecane-1,1-diyl)bis(2-pentylfuran), 5,5'-(2-ethylhexane-1,1-diyl)bis(2-heptylfuran), 5,5'-(dodecane-1,1-diyl)bis(2-hexylfuran), 5,5'-(dodecane-1,1-diyl)bis(2-heptylfuran), 5,5',5"-(butane-1,1,3-triyl)tris(2-pentylfuran), 5,5'-(undecane-2,2-diyl)bis(2-pentylfuran), and 1,1,6,6-tetrakis(5-methylfuran-2-yl)hexane, and (ii) condensed saturated furan compounds (CSFs): 5,5'-(dodecane-1,1-diyl)bis(2-pentyltetrahydrofuran), 5,5'-(dodecane-1,1-diyl)bis(2-butylltetrahydrofuran), 5,5'-(dodecane-1,1-diyl)bis(2-propyltetrahydrofuran), 5,5'-(dodecane-1,1-diyl)bis(2-ethyltetrahydrofuran), 5,5'-(dodecane-1,1-diyl)bis(2-methyltetrahydrofuran), 5,5'-(dodecane-1,1-diyl)bis(2-heptyltetrahydrofuran), 5,5'-(2-ethylhexane-1,1-diyl)bis(2-pentyltetrahydrofuran), 5,5'-(ethane-1,1-diyl)bis(2-pentyltetrahydrofuran), 5,5'-(2-ethylhexane-1,1-diyl)bis(2-heptyltetrahydrofuran), 5,5'-(2-ethylhexane-1,1-diyl)bis(2-hexyltetrahydrofuran), 5,5'-(octane-1,1-diyl)bis(2-pentyltetrahydrofuran), 5,5'-(decane-1,1-diyl)bis(2-pentyltetrahydrofuran), 5,5'-(hexane-1,1-diyl)bis(2-pentyltetrahydrofuran) and 1-((2S)-5-methyltetrahydrofuran-2-yl)-1,6,6-tris(5-methyltetrahydrofuran-2-yl) hexane.

Aspect 11: A lubricant composition comprising:

a. 75-99% by weight of a base oil comprising one or more compounds having the following formula:

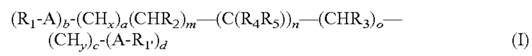

$$(R_1\text{-}A)_b\text{-}(CH_x)_a(CHR_2)_m—(C(R_4R_5))_n—(CHR_3)_o—(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, wherein the total carbon content of the compound of formula (I) is in the range of 20 to 62; and b. an effective amount of one or more lubricant additives (e.g., a total of 1-25% by weight of one or more lubricant additives, based on the total weight of the lubricant composition).

Aspect 12: The lubricant composition according to Aspect 11, wherein at least one of the one or more compounds have a bio-based content in the range of 20 to 100%, according to ASTM-D6866.

Aspect 13: The lubricant composition according to Aspects 11 or 12, wherein at least one of the one or more compounds has a furan ring, a tetrahydrofuran ring or a dihydrofuran ring.

Aspect 14: The lubricant composition according to any of Aspects 11, 12 or 13, wherein $R_1$, $R_{1'}$ of the one or more compounds are independently selected from branched alkyl groups having 3-18 carbon atoms or preferably from acyclic branched alkyl groups having 3-11 carbon atoms.

Aspect 15: The lubricant composition according to any of Aspects 11, 12 or 13, wherein $R_1$ and $R_{1'}$ of the one or more compounds have the formula: $—(CHR_6)—CH_2R_7)$, wherein $R_6$ and $R_7$ are independently H or a linear or branched alkyl group having 2 to 18 carbon atoms, preferably a branched alkyl group having 3-11 carbon atoms, and most preferably an acyclic branched alkyl group having 3-11 carbon atoms.

Aspect 16: The lubricant composition according to any one of Aspects 11-15, wherein $R_2$ and $R_3$ of the one or more compounds are independently selected from the group consisting of branched alkyl groups having 4-9 carbon atoms.

Aspect 17: The lubricant composition according to any of Aspects 11, 12 or 13, wherein both $R_4$ and $R_5$ of the one or more compounds are hydrogen.

Aspect 18: The lubricant composition according to any of Aspects 11, 12 or 13, wherein at least one of $R_1$, $R_{1'}$, $R_2$, $R_3$, $R_4$ and $R_5$ of the one or more compounds is a branched alkyl group with 3-18 carbon atoms.

Aspect 19: The lubricant composition according to any of Aspects 11-15, wherein at least one of the one or more compounds has one of the following structures:

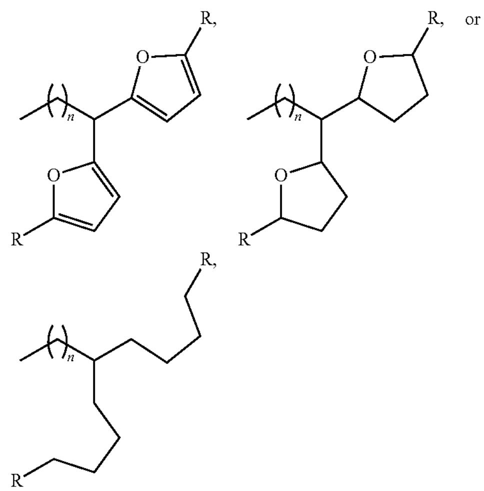

wherein n is 0 to 17, and wherein R is $R_1$ or $R_{1'}$, as defined in Aspect 1.

Aspect 20: The lubricant composition according to any of Aspects 11, 12 or 13, wherein at least one of the one or more compounds has one of the following structures:

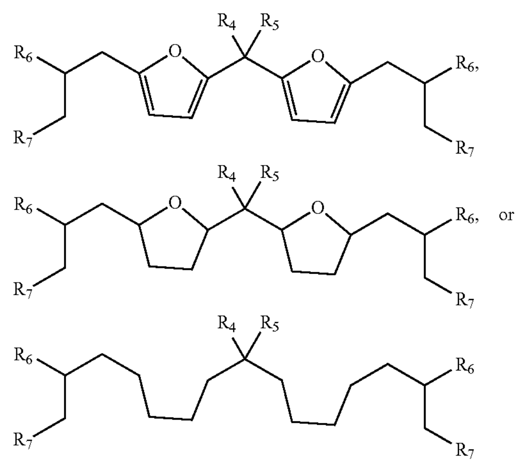

wherein $R_6$ and $R_7$ are independently selected from hydrogen or a substituted or an unsubstituted, a cyclic or an acyclic, a branched or an unbranched alkyl group having 1 to 18 carbon atoms.

Aspect 21: The lubricant composition according to any of Aspects 11, 12 or 13, wherein at least one of the one or more compounds is:

(i) a condensed furan compound (CF) selected from the group consisting of 5,5-(ethane-11-dlyl)bis(2-pentylfuran), 5,5'-(dodecane-1,1-diyl)bis(2-methylfuran), 5,5'-(dodecane-1,1-diyl)bis(2-ethylfuran), 5,5'-(hexane-1,1-diyl)bis(2-pentylfuran), 5,5'-(dodecane-1,1-diyl)bis(2-propylfuran), 5,5'-(octane-1,1-diyl)bis(2-pentylfuran), 5,5'-(2-ethylhexane-1,1-diyl)bis(2-pentylfuran), 5,5'-(dodecane-1,1-diyl)bis(2-butylfuran), 5,5'-(decane-1,1-diyl)bis(2-pentylfuran), 5,5'-(2-ethylhexane-1,1-diyl)bis(2-hexylfuran), 5,5'-(dodecane-1,1-diyl)bis(2-pentylfuran), 5,5'-(2-ethylhexane-1,1-diyl)bis(2-heptylfuran), 5,5'-(dodecane-1,1-diyl)bis(2-hexylfuran), 5,5'-(dodecane-1,1-diyl)bis(2-heptylfuran), 5,5',5"-(butane-1,1,3-triyl)tris(2-pentylfuran), 5,5'-(undecane-2,2-diyl)bis(2-pentylfuran), and 1,1,6,6-tetrakis(5-methylfuran-2-yl)hexane.

(ii) a condensed furan alkane compound (CFA) selected from the group consisting of 10-methylnonadecane, 6-pentylheptadecane, 7-hexyloctadecane, 10-pentylnonadecane, 8-heptylnonadecane, 10-heptylnonadecane, 10-(heptan-3-yl)nonadecane, 9-octylicosane, 10-nonylnonadecane, 11-(heptan-3-yl)henicosane, 10-nonylhenicosane, 12-(heptan-3-yl)tricosane, 11-decyldocosane, 12-undecyltricosane, 10-methyl-12-nonylhenicosane, 10-methyl-10-nonylnonadecane, and 6,11-dipentylhexadecane, and (iii) a condensed saturated furan compound (CSF) selected from the group consisting of: 5,5'-(dodecane-1,1-diyl)bis(2-pentyltetrahydrofuran), 5,5'-(dodecane-1,1-diyl)bis(2-butylltetrahydrofuran), 5,5'-(dodecane-1,1-diyl)bis(2-propyltetrahydrofuran), 5,5'-(dodecane-1,1-diyl)bis(2-ethyltetrahydrofuran), 5,5'-(dodecane-1,1-diyl)bis(2-methyltetrahydrofuran), 5,5'-(dodecane-1,1-diyl)bis(2-heptyltetrahydrofuran), 5,5'-(2-ethylhexane-1,1-diyl)bis(2-pentyltetrahydrofuran), 5,5'-(ethane-1,1-diyl)bis(2-pentyltetrahydrofuran), 5,5'-(2-ethylhexane-1,1-diyl)bis(2-heptyltetrahydrofuran), 5,5'-(2- ethylhexane-1,1-diyl)bis(2-hexyltetrahydrofuran), 5,5'-(octane-1,1-diyl)bis(2-pentyltetrahydrofuran), 5,5'-(decane-1,1-diyl)bis(2-pentyltetrahydrofuran), 5,5'-(hexane-1,1-diyl)bis(2-pentyltetrahydrofuran) and 1-((2S)-5-methyltetrahydrofuran-2-yl)-1,6,6-tris (5-methyltetrahydrofuran-2-yl) hexane.

Aspect 22: The lubricant composition according to any of Aspects 11-21, wherein the one or more lubricant additives are selected from the group consisting of antioxidants, stabilizers, detergents, dispersants, demulsifiers, antioxidants, anti-wear additives, pour point depressants, viscosity index modifiers, friction modifiers, anti-foam additives, defoaming agents, corrosion inhibitors, wetting agents, rust inhibitors, copper passivators, metal deactivators, extreme pressure additives, and combinations thereof.

Aspect 23: The lubricant composition according to any of Aspects 11-22, further comprising one or more co-base oils selected from the group consisting of API Group I base oil, Group II base oil, Group III base oil, Group IV base oil, Group V base oil, gas-to-liquid (GTL) base oil, and combinations thereof (the one or more co-base oils may comprise, for example, from 1-25% by weight of the lubricant composition).

Aspect 24: The lubricant composition according to any one of the preceding Aspects 11-23, wherein at least one of the one or more compounds of formula (I) has a kinematic viscosity at 100° C. in the range of 2 to 100 CSt, as measured by ASTM D445.

Aspect 25: The lubricant composition according to any one of the preceding Aspects 11-24, wherein at least one of the one or more compounds of formula (I) has a kinematic viscosity at 40° C. in the range of 6 to 100 CSt, as measured by ASTM D445.

Aspect 26: The lubricant composition according to any one of the preceding Aspects 11-25, wherein at least one of the one or more compounds of formula (I) has a viscosity index calculated from kinetic viscosity at 100° C. and 40° C., in the range of 100 to 200, as measured by ASTM D2270.

Aspect 27: The lubricant composition according to any one of the preceding Aspects 11-26, wherein the at least one of the one or more compounds of formula (I) has a pour point in the range of −12° C. to −80° C., as measured by ASTM D97.

Aspect 28: The lubricant composition according to any one of the preceding Aspects 11-27, wherein the at least one of the one or more compounds formula (I) has an oxidation stability in the range of 170° C. to 300° C., as measured by ASTM D6375.

Aspect 29: The lubricant composition according to any one of the preceding Aspects 11-28, wherein the base oil has a kinematic viscosity of at least 3 cSt, as measured by ASTM D445.

Aspect 30: The lubricant composition according to any one of the preceding Aspects 11-29, wherein the base oil has a bio-based content in the range of 20 to 100%, according to ASTM-D6866.

Aspect 31: Use of the lubricant composition according to any one of the preceding Aspects 11-30, in one or more of industrial machinery, automobiles, aviation machinery, refrigeration compressors, agricultural equipment, marine vessels, agriculture equipment, medical equipment, hydropower production machinery, and food processing equipment.

Aspect 32: Use of a lubricant base oil comprising one or more compounds of formula (I) in one or more of industrial machinery, automobiles, aviation machinery, refrigeration compressors, agricultural equipment, marine vessels, agriculture equipment, medical equipment, hydropower production machinery, and food processing equipment, wherein the one or more compounds have the following formula:

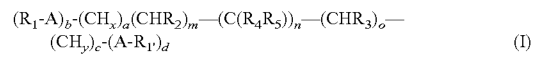

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62.

Aspect 33: A method of making a compound having the following formula:

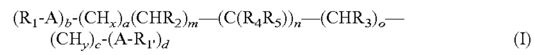

$$(R_1\text{-}A)_b\text{-}(CH_x)_a(CHR_2)_m\text{—}(C(R_4R_5))_n\text{—}(CHR_3)_o\text{—}(CH_y)_c\text{-}(A\text{-}R_{1'})_d \quad (I)$$

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62, wherein the method comprises the steps of:

a) providing a first component comprising one or more of a 2-alkylfuran having the formula R1-A and/or R1'-A wherein R1, R1', are independently selected from the group consisting of H and alkyl groups having 1 to 18 carbon atoms and A is a furan ring and a second component comprising one or more of:

(i) an aldehyde having the formula $R_4R_5CO$, wherein at least one of $R_4$ or $R_5$ is hydrogen and at most one of $R_4$ or $R_5$ is an alkyl group having 1 to 18 carbon atoms, (ii) a dialdehyde having the formula $(CR_4R_5)_n(CHO)_2$, wherein each $R_4$ and $R_5$ is independently selected from the group consisting of H and alkyl groups having 1 to 18 carbon atoms and n is an integer of 1-8, (iii) an enal having the formula $CHR_2{=}CR_3{—}CHO$, wherein $R_2$ and $R_3$ are independently selected from the group consisting of H and alkyl groups having 1 to 18 or 2 to 8 carbon atoms, and (iv) a ketone having the formula $R_4R_5CO$, wherein each $R_4$ and $R_5$ is independently selected from the group consisting of alkyl groups having 1 to 18 carbon atoms, wherein at least one of the first component and the second component is bio-derived from a renewable source;

b) condensing the first component with the second component in the presence of an acidic catalyst to form a condensed furan compound (CF);

c) optionally hydrogenating the condensed furan compound in the presence of a hydrogenation catalyst to obtain a condensed saturated furan compound (CSF); and d) optionally hydrodeoxygenating the condensed furan compound or the condensed saturated furan compound in the presence of a hydrodeoxygenation catalyst to obtain a condensed furan alkane compound (CFA).

Aspect 34: The method according to Aspect 33, wherein the step of providing an aldehyde comprises at least one of dehydrogenating biomass derived alcohols and selective hydrogenation of fatty acids from natural oils or waste cooking oils.

Aspect 35: The method according to Aspect 33, wherein the 2-alkylfuran has been prepared by a process comprising (a) dehydration and hydrodeoxygenation of C5 sugars of biomass, or (b) furan acylation with one or more carboxylic acids or carboxylic acid anhydrides wherein furan acylation followed by hydrodeoxygenation of the acylated products.

Aspect 36: The method according to any one of Aspects 33-35, wherein the step of condensing 2-alkylfuran with the aldehyde, the dialdehyde, the enal or the ketone comprises carrying out the condensing in the presence of at least one thiol selected from the group consisting of ethanethiol, propanethiol, butanethiol and combinations thereof, preferably propanethiol.

Aspect 37: The method according to any one of Aspects 33-36, wherein the acidic catalyst comprises liquid acids including inorganic liquid acids and organic liquid acids, and solid acids.

Aspect 38: The method according to any one of Aspects 33-37, wherein the step c) of Aspect 33 is performed in the presence of a hydrogenation catalyst and the hydrogenation catalyst is a metal base catalyst chosen from palladium catalysts supported on carbon or acidic materials or a nickel based catalyst, and wherein palladium catalyst are preferably Pd/C, $Pd/SiO_2$ and $Pd/Al_2O_3$, and Ni-based catalysts are Raney Ni.

Aspect 39: The method according to any one of Aspects 33-38, wherein the step d) of Aspect 33 is performed in the presence of a hydrodeoxygenation catalyst and the hydrodeoxygenation catalyst is a solid acid supported metal based catalyst or a physical mixture of a metal based catalyst, preferably Pd/C, $Pd/SiO_2$ and Pt/C, with a solid acid.

Aspect 40: The method according to Aspect 39, wherein the solid acid supported metal based catalyst comprises Ni/ZSM-5, Pd/ZSM-5, Pd/BEA, or a physical mixture of a metal based catalyst with a solid acid, including Pd/C+ZSM-5, Pd/C+BEA, Pt/C+BEA, and preferably supported metal-metal oxide catalysts such as Ir—$ReO_x/SiO_2$, Ir—$MoO_x/SiO_2$ or $^1M^2MO/SiO_2$, wherein $^1M$=Ir, Ru, Ni, Co, Pd, Pt, or Rh and $^2M$=Re, Mo, W, Nb, Mn, V, Ce, Cr, Zn, Co, Y, or Al.

Aspect 41: Use of the compound having the formula (I), prepared according to any of Aspects 33-40, as a base oil in pharmaceutical and personal care products.

Aspect 42: A personal care composition comprising:

a. a base oil comprising one or more compounds having the following formula and derivatives thereof:

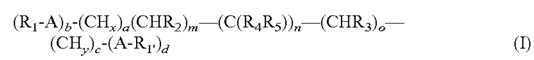
$(R_1\text{-}A)_b\text{-}(CH_x)_a(CHR_2)_m—(C(R_4R_5))_n—(CHR_3)_o—(CH_y)_c\text{-}(A\text{-}R_{1'})_d$ (I)

wherein:

(i) each of a and c is independently 0 or 1, (ii) each of b and d is independently 1 or 2, (iii) each of x and y is independently 1 or 2, dependent upon the values of a-d, (iv) each of m and o is independently 0 or 1, and (v) n is an integer of 0-6 wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, wherein the total carbon content of the compound of formula (I) is in the range of 20 to 62; and b. an effective amount of one or more additives selected from the group consisting of pigment, fragrance, emulsifier, wetting agent, thickener, emollient, rheology modifier, viscosity modifier, gelling agent, antiperspirant agent, deodorant active, fatty acid salt, film former, anti-oxidant, humectant, opacifier, monohydric alcohol, polyhydric alcohol, fatty alcohol, preservative, pH modifier, a moisturizer, skin conditioner, stabilizing agent, proteins, skin lightening agents, topical exfoliants, antioxidants, retinoids, refractive index enhancer, photo-stability enhancer, SPF improver, UV blocker, and water.

Aspect 43: The personal care composition of Aspect 42, further comprising an active ingredient selected from the group consisting of antibiotic, antiseptic, antifungal, corticosteroid, and anti-acne agent.

Aspect 44: A pharmaceutical composition comprising:

a. a base oil comprising one or more compounds having the following formula and derivatives thereof:

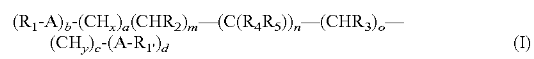
$(R_1\text{-}A)_b\text{-}(CH_x)_a(CHR_2)_m—(C(R_4R_5))_n—(CHR_3)_o—(CH_y)_c\text{-}(A\text{-}R_{1'})_d$ (I)

wherein:

i. each of a and c is independently 0 or 1, ii. each of b and d is independently 1 or 2, iii. each of x and y is independently 1 or 2, dependent upon the values of a-d, iv. each of m and o is independently 0 or 1, and v. n is an integer of 0-6;

wherein each A is independently an unsaturated furan ring, a partially saturated furan ring, a saturated furan ring, or $—(CH_2)_4—$, wherein $R_1$, $R_{1'}$, $R_2$, $R_3$, $R_4$ and $R_5$ are independently selected from the group consisting of H and alkyl groups having 1 to 18 carbon atoms, with a proviso that at least one of $R_2$, $R_3$, $R_4$, and $R_5$ is not H, wherein the alkyl groups are substituted or unsubstituted, cyclic or acyclic, or branched or unbranched, wherein $R_1$ and $R_{1'}$ may be the same or different, and wherein the total carbon content of the compound of formula (I) is in the range of 20 to 62;

b. an effective amount of one or more pharmaceutically active ingredients; and c. optionally, one or more pharmaceutically acceptable excipients.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The term "about" refers to the variation in the numerical value of a measurement, e.g., temperature, weight, percentage, length, concentration, and the like, due to typical error rates of the device used to obtain that measure. In one embodiment, the term "about" means within 5% of the reported numerical value.

As used herein, the singular form of a word includes the plural, and vice versa, unless the context clearly dictates otherwise. Thus, the references "an", and "the" are generally inclusive of the plurals of the respective terms. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The term "comprising" is intended to include embodiments encompassed by the terms "consisting essentially of" and "consisting of". Similarly, the term "consisting essentially of" is intended to include embodiments encompassed by the term "consisting of".

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the compounds for use as a lubricant base oil, lubricant base oil compositions based on such compounds and process for making such compounds.

Additionally, in some embodiments, the invention can be construed as excluding any element or process step not specified herein.

Although the invention is illustrated and described herein with reference to specific embodiments, the invention is not intended to be limited to the details shown.

Rather, various modifications may be made in the details within the scope and range of EQUIVALENTS OF THE CLAIMS AND WITHOUT DEPARTING FROM THE INVENTION.

EXAMPLES

Examples of the present invention will now be described. The technical scope of the present invention is not limited to the examples described below.

Abbreviations

The meaning of abbreviations is as follows: "cm" means centimeter(s), "g" means gram(s), "h" or "hr" means hour(s), "HPLC" means high pressure liquid chromatography, "m" means meter(s), "min" means minute(s), "mL" means milliliter(s), "mm" means millimeter(s), "MPa" means megapascal(s), "psi" means pound(s) per square inch, "rpm" means revolutions per minute, "wt %" means weight percent(age).

Example 1. General Materials and Methods

Materials

Aquivion® PW98 (coarse powder), Nafion® NR50 (pellets), Amberlyst®-15 (dry hydrogen form, BET surface area 42 $m^2/g$), amorphous silica-alumina (ASA, catalyst support grade 135, 12 wt % $Al_2O_3$, >90% AS-100 mesh, 54 Å, BET surface area 569 $m^2/g$), methanesulfonic acid (≥99.0%), acetic acid, silica gel (high-purity grade, 60 Å, 70-230 mesh), 2-pentylfuran (≥98.0%), 2-methylfuran (99%), 2-ethylfuran (99.0%), lauraldehyde (≥95%), hexanal (98%), octanal (99%), decanal (≥98.0%). 2 -ethylhexanal (96%), eicosane (99%), Pd/C (10 wt % Pd loading) and $H_2IrCl_6$ (99.98%, trace metal basis) were purchased from Sigma-Aldrich. 2-Propylfuran (>98%) and 2-butylfruan (>98%) were purchased from Tokyo Chemical Industry Co., Ltd. 2-Hexylfuran (97%) and 2-heptylfuran (97%) were purchased from Alfa-Aesar. Amberlyst® 36 dry resin (BET surface area 33 $m^2/g$) was purchased from Rohm and Haas Company. 5 M $H_2SO_4$ was purchased from Fluka. o-Phosphoric acid (85%) and cyclohexane (99.9%) was purchased from Fisher Chemical. Ammonium perrhenate(VII), (99.999%, metals basis) was purchased from Alfa-Aesar. Silica gel G6 (BET surface area 535 $m^2/g$) was kindly provided by Fuji Silysia Chemical Ltd. The commercial ZSM-5 (CBV2314, Si/Al=11.5) and HY (CBV720, Si/Al=15) are purchased from Zeolyst.

Materials Pretreatment

2-Alkylfurans (2-methylfuran, 2-ethylfuran, 2-propylfuran, 2-butylfruan, 2-pentylfuran, 2-hexylfuran and 2-heptylfuran) were purified by vacuum distillation for use in the examples below.

The zeolites ZSM-5 and HY were calcined at 550° C. for 4 h at a heating rate of 2° C./min. The ASA was calcined prior to use for 10 h at 500° C. at a heating rate of 2° C./min under static air. The silica gels were calcined in air at 700° C. for 1 h at a heating rate of 10° C./min before catalyst impregnation.

Catalyst Preparation

Certain of the processes described in the examples required the use of catalysts; namely, a P—$SiO_2$ catalyst or an Ir—$ReO_x$/$SiO_2$ catalyst. The P—$SiO_2$ catalyst ($H_3PO_4$, 10 wt % loading) was prepared by the impregnation method. First, $SiO_2$ (Sigma-Aldrich) was impregnated by aqueous $H_3PO_4$ solution. After evaporating the solvent at 75° C. on a hotplate and subsequently drying at 110° C. for 12 h in an oven, the catalyst was calcined in a crucible in air at 500° C. for 3 h with a 2° C./min temperature ramp.

The Ir—$ReO_x$/$SiO_2$ (Ir 4 wt % loading, Re/Ir=2, molar) catalyst was prepared by the sequential impregnation method. First, Ir/$SiO_2$ was prepared by impregnating Ir on $SiO_2$ (Fuji Silysia G-6) using an aqueous solution of $H_2IrCl_6$. After evaporating the solvent at 75° C. on a hotplate and drying at 110° C. for 12 h in an oven, the resulting Ir/$SiO_2$ was impregnated with $ReO_x$ using an aqueous solution of $NH_4ReO_4$. The catalysts were calcined in a crucible in air at 500° C. for 3 h at a 10° C./min temperature ramp. The reported metal loadings in the catalysts are based on the theoretical amount of metals used for impregnation.

Reaction Procedures for Catalysis

Process of Making a Condensed Furan Compound (CF) by Hydroxyalkylation/Alkylation (HAA) Reaction 10 mmol 2-alkylfuran and 5 mmol aldehyde without any solvent were mixed in a 20 ml glass vial. The vial was placed in a preheated oil bath and stirred at 500 rpm using a magnetic bar on a stirring cum hot plate. Finally, the catalyst was added into the vial and the reaction was continued at desired temperature (65° C. unless otherwise mentioned) for 6 hr. After carrying out the reaction for the desired time, the solution was diluted using 10 ml cylcohexane solvent. A small amount of eicosane was added as an internal standard. The CF compounds were isolated by vacuum distillation.

Process of Making a Condensed Saturated Furan Compound (CSF) by Hydrogenation Reaction Hydrogenation of the HAA condensation products, obtained according to the above procedure, were carried out in a 50 ml Parr reactor with an inserted Teflon liner and a magnetic stirrer. First, Pd/C catalyst was pretreated at 200° C. with a ramp of 10° C./min for 1 h with $H_2$ (50 ml/min). Then Pd/C catalyst (0.03 g), CF (0.5 g) and 10 ml cyclohexane were added to the reactor and the mixture was heated at 60° C. After the reaction for the set time, the reactor was immediately transferred to an ice-water bath for quenching the reaction. After cooling down the solution to the room temperature, the reactor was opened and the solution was diluted using 10 ml cyclohexane containing a small amount of eicosane as an internal standard and the catalyst was separated from the solution by filtration. Experiments were also conducted using as-received Pd/C without pretreatment. The CSF compounds were isolated by vacuum distillation.

Process of Making a Condensed Furan Alkane Compound (CFA) by Hydrodeoxygenation (HDO) Reaction HDO of CFs over Ir—$ReO_x$/$SiO_2$ was performed in a 50 mL Parr reactor with an inserted Teflon liner and a magnetic stirrer. First, catalyst (0.15 g) and solvent (cyclohexane, 10 mL) were added to the reactor for the catalyst pre-reduction and the reactor was sealed with the reactor head equipped with a thermocouple, a rupture disk, a pressure gauge, and a gas release valve. The mixture was heated at 200° C. and 5 MPa $H_2$ for 1 h at 240 rpm. Upon pre-reduction, the reactor was cooled to room temperature and $H_2$ was released. Then, CFs (0.3 g) was added, closed the reactor head immediately, purged the reactor with $H_2$ (1 MPa) for three times, pressurized to 5 MPa $H_2$, and heated the reaction mixture to the desired temperature with continuous stirring at 500 rpm. The heating time to reach the set temperature was about 25 min. After reaction for the set time, the reactor was immediately transferred to a water bath. After reaction, the solution was diluted using 15 ml cyclohexane with a small amount of eicosane as an internal standard and the catalyst was separated from the solution by centrifugation or filtration. The CFA compounds were isolated by vacuum distillation.

Analysis of Products

The products, CF, CSF and CFA compounds were analysed by a gas chromatograph (GC, Agilent 7890A) equipped with an HP-1 column and a flame ionization detector (FID) using eicosane ($C_{20}$) as an internal standard. The products were identified by a GC (Agilent 7890B) mass spectrometer (Agilent 5977A with a triple-axis detector) equipped with a DB-5 column, high resolution MS with liquid injection field desorption ionization (LIFDI), $^1H$ NMR and $^{13}C$ NMR.

The conversion and the yield of all products from HAA, hydrogenation and HDO reactions were calculated on carbon basis using the following equations:

$$\text{Conversion [\%]} = \frac{\text{mol of initial reactant} - \text{mol of unreacted reactant}}{\text{mole of initial reactant}} \times 100$$

$$\text{Yield of detected products } [\% - C] = \frac{\text{mol}_{product} \times C \text{ atoms in product}}{\text{mol of total } C \text{ atoms of initial reactant}} \times 100$$

Homogeneous Catalyst Screening

Figures 1B, 1C, 1D:
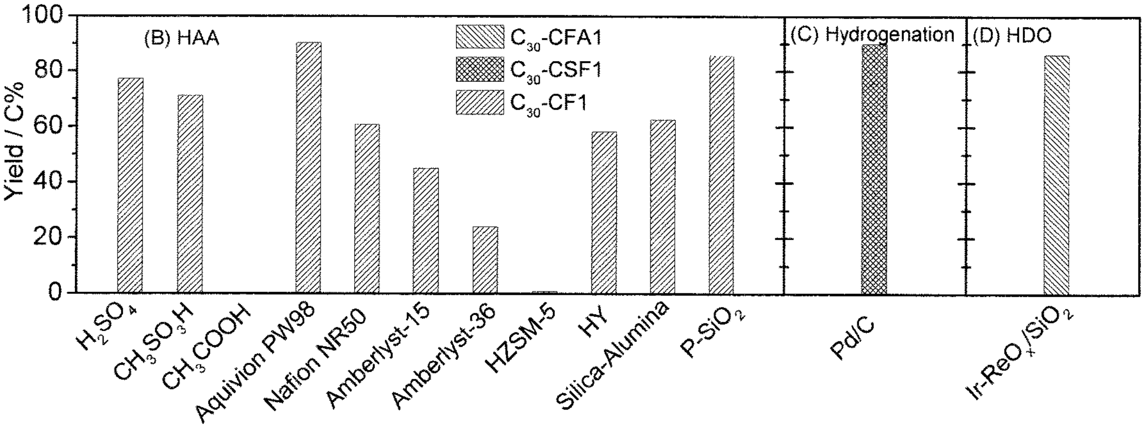
FIG. 1B shows $C_{30}$-CF1 yields from the HAA reaction of 2-pentylfuran with lauraldehyde over various acid catalysts. (Reaction conditions: 10 mmol 2-pentylfuran, 5 mmol lauraldehyde, 0.05 mmol $H^+$, e.g., 0.05 g Aquivion© PW98, 65° C., 6 hr).
FIG. 1C shows hydrogenation results of $C_{30}$-CF1 to $C_{30}$-CSF1 over as-received and pre-reduced Pd/C catalysts. (Reaction conditions: 0.5 g $C_{30}$-CF1, 0.03 g catalyst at 200° C. with a ramp of 10° C./min for 1 h with $H_2$ (50 ml/min)).
FIG. 1D shows hydrodeoxygenation results of $C_{30}$-CF1 to $C_{30}$-CBA1 over Ir—$ReO_x/SiO_2$ catalysts. (Reaction conditions: 0.3 g $C_{30}$-CF1, 0.15 g of catalyst, at 170° C. and 5 MPa $H_2$ for 12 h).
Figure 2:
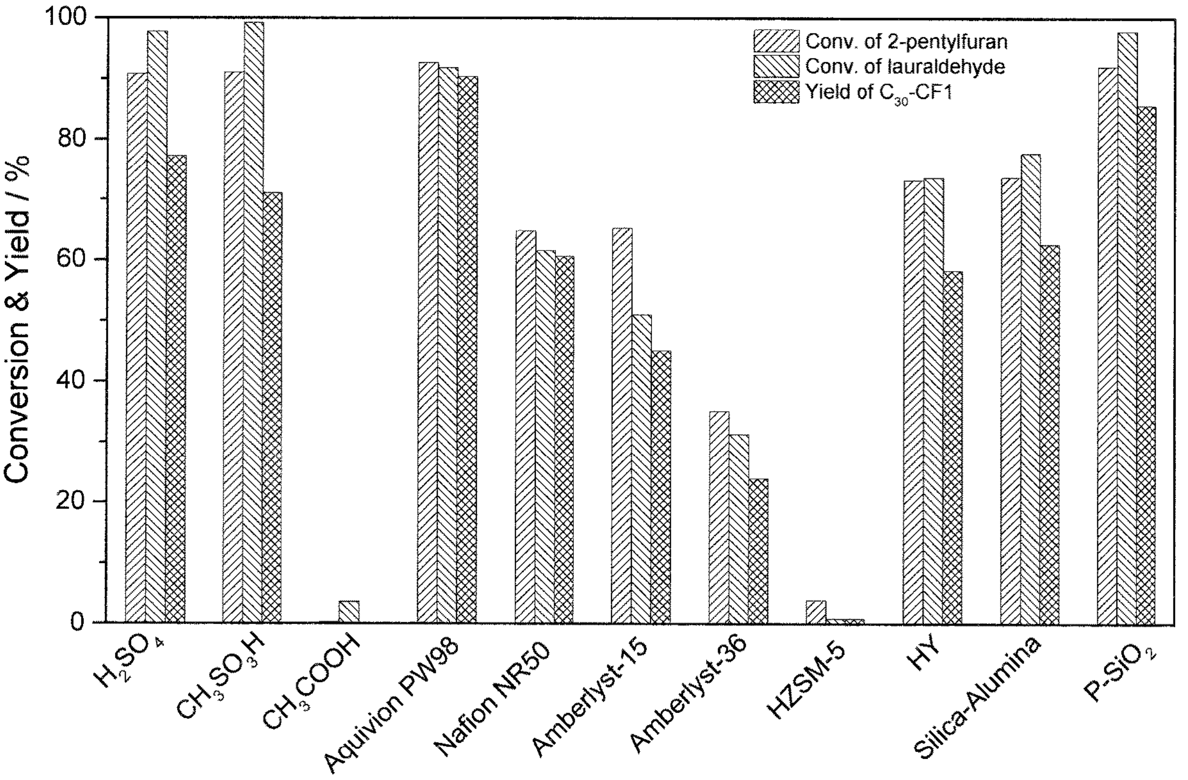
FIG. 2 shows catalysts screening for the synthesis of $C_{30}$-CF1. (Reaction conditions: 10 mmol 2-pentylfuran, 5 mmol lauraldehyde, $H^+$ 0.05 mmol (e.g. Aquivion PW98 0.05 g), 65° C., 6 h).

Initial screening of homogeneous catalysts (sulfuric acid, methanesulfonic acid and acetic acid) for $C_{30}$-CF1 synthesis was conducted using 2-pentylfuran and lauraldehyde as the starting substrates, as shown in FIG. 1B. Any suitable synthetic route can be used to prepare 2-pentylfuran, for example it can be produced from the acylation of furan with valeric acid or valeric anhydride followed by HDO (Reference 11). Lauraldehyde can be synthesized from lauric acid of coconut oil by selective hydrogenation (Reference 9). FIGS. 1C and 2 show that sulfuric and methanesulfonic acid catalyzed HAA reactions achieved up to 77% yield of $C_{30}$-CF1 under neat conditions and at 2:1 molar ratio of 2-pentylfuran and lauraldehyde, using the procedure and product analysis data, as disclosed hereinabove.

In contrast, weakly acidic acetic acid is ineffective. While this pathway is feasible, homogeneous acid separations and disposal can be challenging, and bio-lubricant base-oils will be corrosive.

Solid Acid Catalyst Screening

To overcome the aforementioned challenges, several solid sulfonic acid resins, e.g. perfluorinated sulfonic acid resins (Aquivion© PW98, Nafion® NR50) and sulfonic-acid-functionalized cross-lined polystyrene resins (Amberlyst®-15 and Amberlyst®-36) were evaluated.

The catalytic performance of the four resin catalysts follows the order of Aquivion® PW98>Nafion® NR50>Amberlyst® 15>Amberlyst® 36.

High yield and selectivity of $C_{30}$-$C_{F1}$ (90% yield with >98% selectivity for 6 hr at 65° C. using 0.05 g catalyst) is achieved by Aquivion® PW98 because of its strong acid strength and high contact surface area, as shown below in Table 1.

TABLE 1

The properties of commercial solid acid catalysts

| Entry | Catalyst | Acid density ($H^+$ mmol/g) | Surface area ($m^2$/g) | Pore diameter (nm) | Form | Reference |
|---|---|---|---|---|---|---|
| 1 | Aquivion PW98 | 1.0 | <1 | — | Coarse powder | 12 |
| 2 | Nation NR50 | 0.89 | <1 | — | Pellets | 13 |
| 3 | Amberlyst-15 | 4.8 | 42 | 34.3 | Beads | 14 |
| 4 | Amberlyst-36 | 5.4 | 33 | 32.9 | Beads | 14 |
| 5 | HZSM-5 | 0.65 | 425 | ~0.5 | Powder | 15 |
| 6 | HY | 0.31 | 780 | ~0.7 | Powder | 16 |
| 7 | Silica-Alumina | 0.34 | 569 | 5.4 | Powder | 16 |

Figure 3:
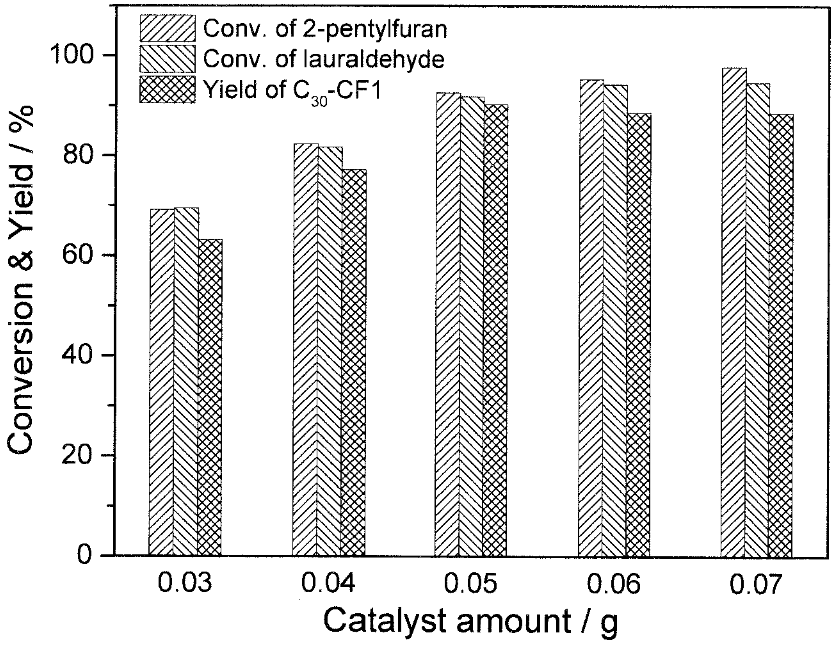
FIG. 3 shows the effect of the catalyst (Aquivion PW98) amount on the yield of $C_{30}$-CF1 at low and high conversions of reactants. (Reaction conditions: (a) 10 mmol 2-pentylfuran, 5 mmol lauraldehyde, 65° C. (a) 6 hr, (b) 1 hr).
Figure 4:
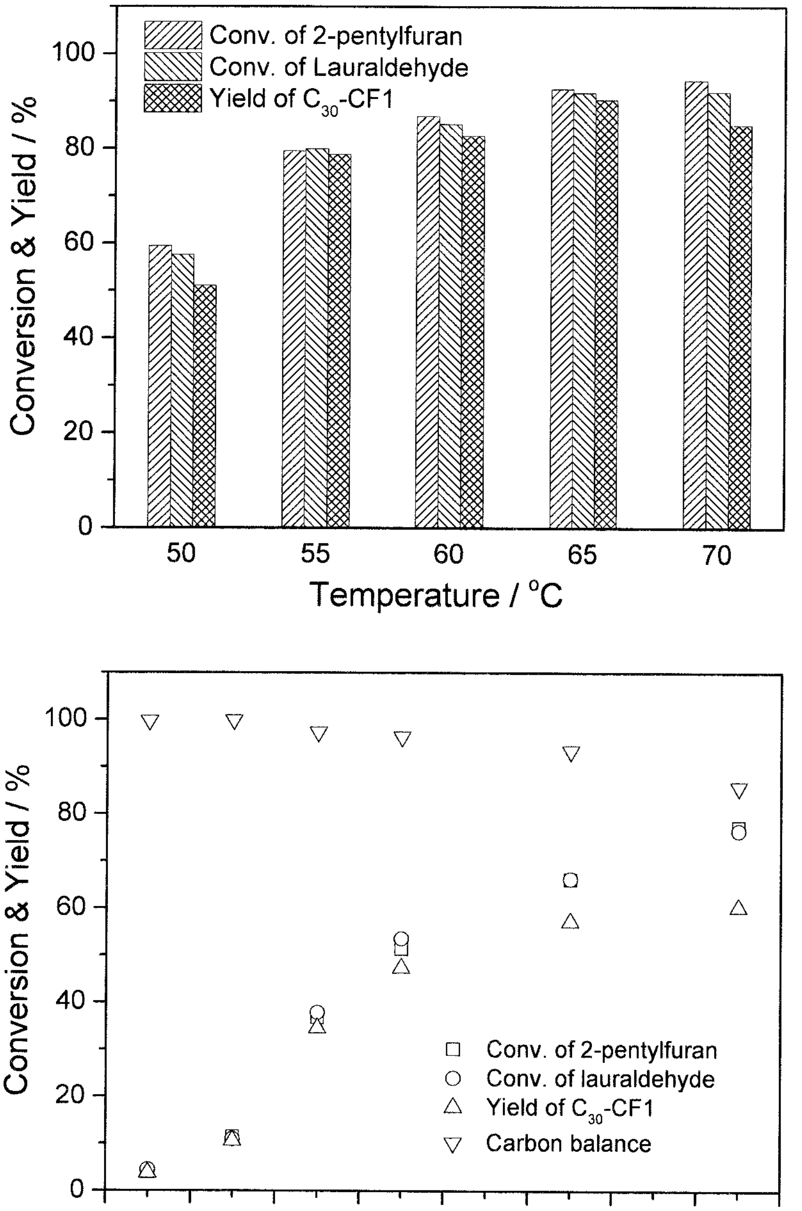
FIG. 4 shows the effect of reaction temperatures on the production of $C_{30}$-CF1. (Reaction condition: 10 mmol 2-pentylfuran, 5 mmol lauraldehyde, (a) Catalyst: 0.05 g, 6 h (a) Catalyst: 0.02 g, 0.5 h).
Figure 5:
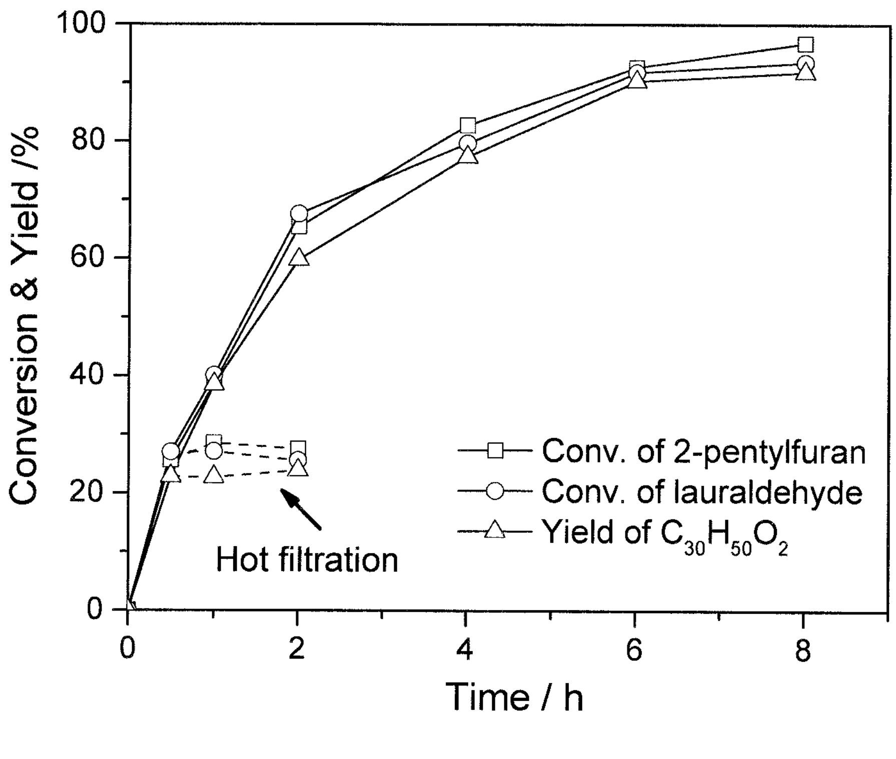
FIG. 5 shows the conversion of reactants and yield of the HAA reaction for $C_{30}$-CF1 synthesis over Aquivion® PW98 catalyst over time. (Reaction condition: 10 mmol 2-pentylfuran, 5 mmol lauraldehyde, Aquivion PW98 0.05 g, 65° C.).
Figure 6:
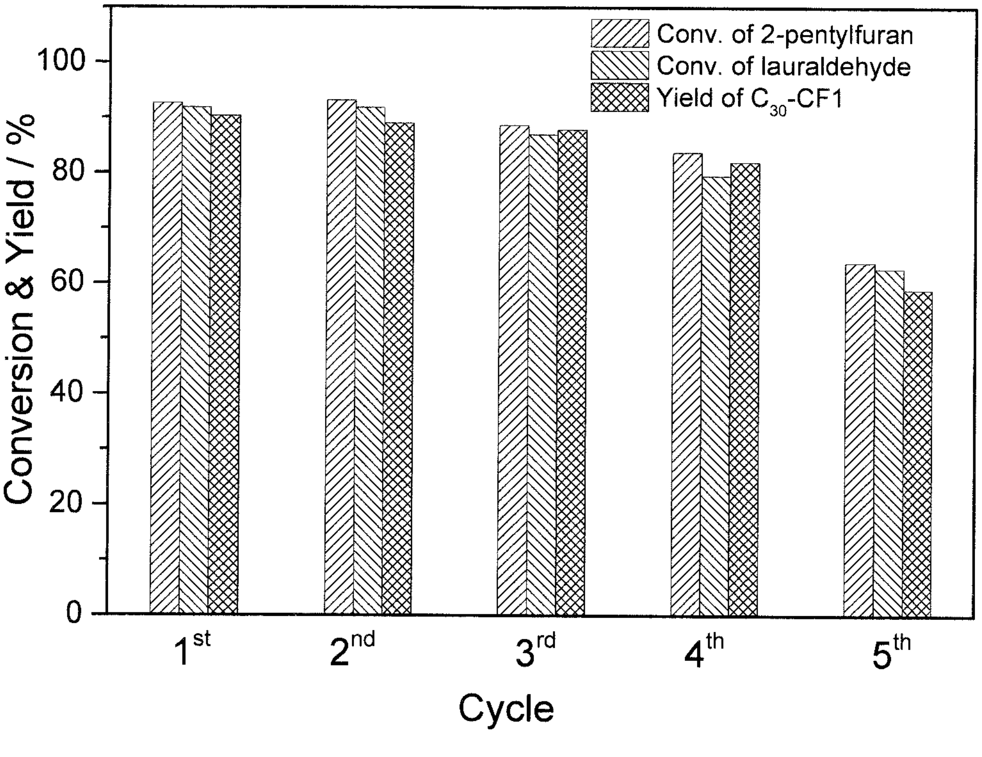
FIG. 6 shows the recyclability of catalyst Aquivion PW98 for the synthesis of $C_{30}$-CF1 by HAA reaction. (Reaction condition: 10 mmol 2-pentylfuran, 5 mmol lauraldehyde, catalyst: 0.05 g, 6 hr)

FIGS. 3 and 4 demonstrate the reaction at low and high conversions. The reaction for 8 hr yields 92% $C_{30}$-CF1 (FIG. 5). Controlled experiments show no leaching of acidic sites in the solution and Aquivion® PW98 retained almost comparable catalytic performance up to four consecutive cycles, as shown in FIG. 6. About 30% activity loss is observed in the fifth cycle with concurrent mass gain and brown coloration of the recovered Aquivion® PW98, indicating polymer coating could be formed on the catalyst that could block the surface acid sites. Regeneration by calcination was not attempted because of thermal stability challenge of Aquivion® PW98 at temperature>160° C.

The effectiveness of solid acids with high thermal resistance for $C_{30}$-CF1 synthesis was also evaluated. Among microporous acidic zeolites (HZSM-5 and HY), HY gaves a moderate yield (58%) of $C_{30}$-CF1 under comparable reaction conditions as the resin catalysts while HZSM-5 was found to be ineffective (<1% $C_{30}$-CF1), as shown in FIG. 1C.

Figure 7:
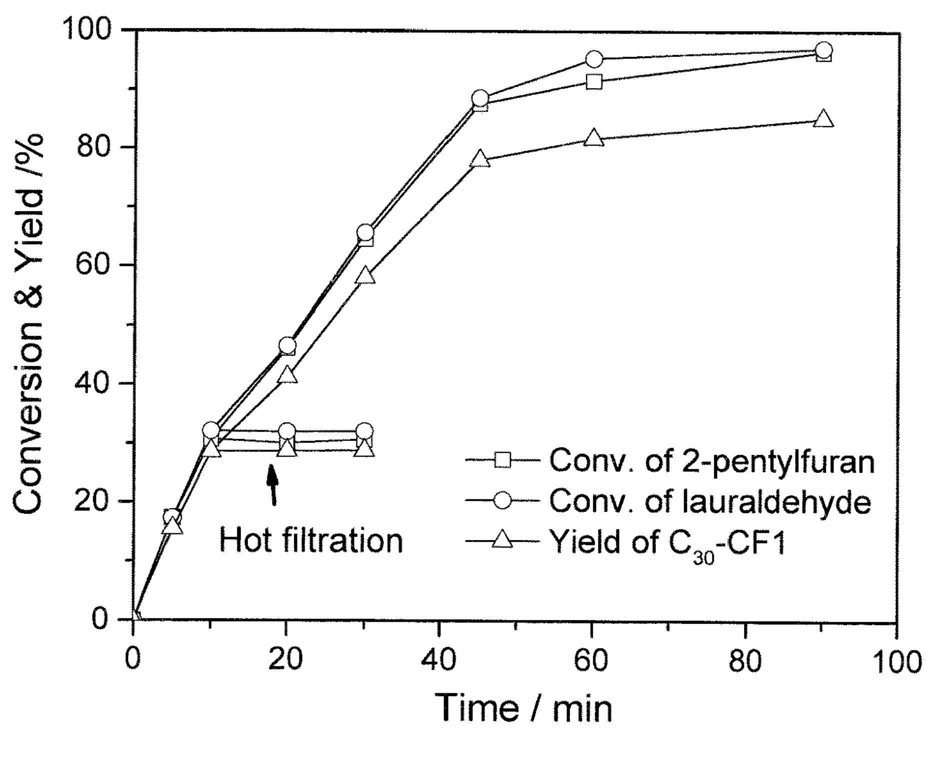
FIG. 7 shows conversion of reactants and yield of the HAA reaction for $C_{30}$-CF1 synthesis over the P—$SiO_2$ catalyst. (Reaction condition: 10 mmol 2-pentylfuran, 5 mmol lauraldehyde, 0.05 g P—$SiO_2$, 65° C.)
Figure 8:
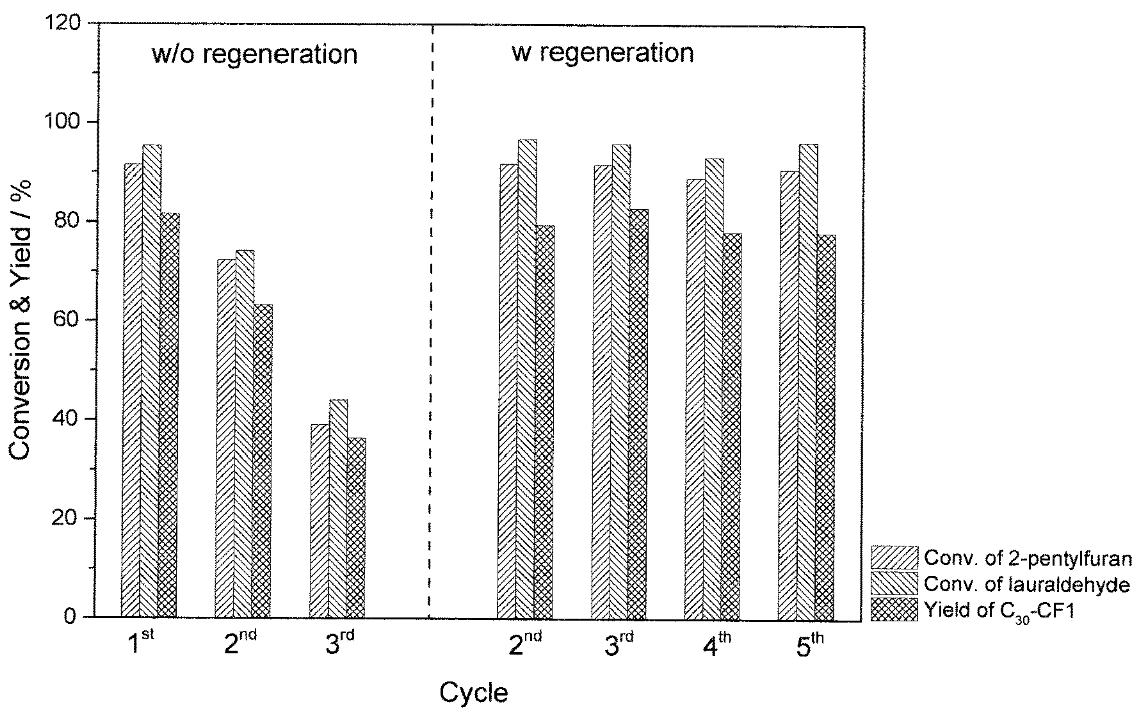
FIG. 8 shows recyclability of catalyst P—$SiO_2$ for the synthesis of $C_{30}$-CF1 by HAA reaction. (Reaction condition: 10 mmol 2-alkylfuran, 5 mmol aldehyde, 0.05 g P—$SiO_2$, 65° C., 1 hr).
Figure 9:
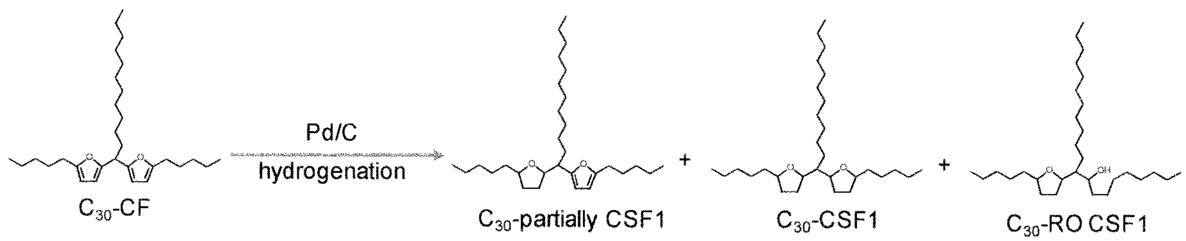
FIG. 9 shows hydrogenation of $C_{30}$-CF1 over pretreated Pd/C. (Reaction condition: 0.5 g $C_{30}$-CF, 0.03 g Pd/C, 60° C., Pd/C was reduced under $H_2$ (50 ml/min) at 200° C. for 1 hr).
Figure 9:
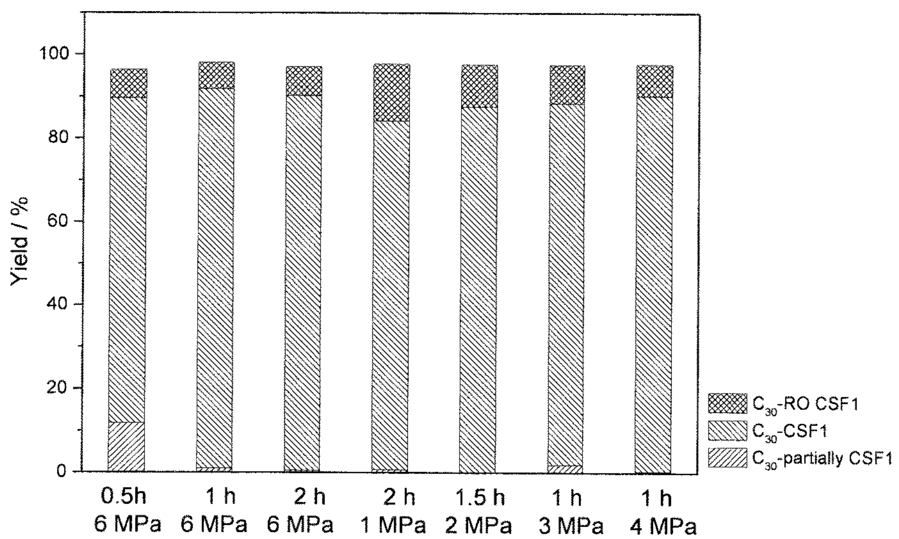

Since diffusion control could be a challenge in the synthesis of large molecules over the microporous zeolites, mesoporous aluminosilicate with a pore diameter of ~5.4 nm was chosen. The aluminosilicate catalyst exhibited comparable performance as HY, likely the benefit of the larger pore diameters is counterbalanced by its lower acid strength in a non-crystalline environment. P-containing zeolites showed high activity due to their unique acidic properties. A P-containing mesoporous siliceous (P—$SiO_2$) catalyst, prepared by a simple impregnation method, exhibited superior performance to mesoporous aluminosilicate, and yielded $C_{30}$-CF1 with nearly comparable yield as Aquivion PW98 in much shorter reaction time (1.5 hr) as compared to Aquivion PW98 (6 hr), as shown in FIGS. 2 and 7. Homogeneous phosphoric acid showed no activity, even with double the amount of P-concentration. Hot filtration indicated no leaching of P-sites from P—$SiO_2$ in the solution, as shown FIG. 7. Coke formation on P—$SiO_2$ caused a loss of catalytic activity in the second cycle, as shown in FIG. 8. Furthermore, FIG. 8 shows that regenerated P—$SiO_2$, upon calcination at 500° C. in air for 3 hr, regained comparable performance as the fresh catalyst.

Lubricant Base Oil Properties Measurements

The lubricant properties of selected $C_{30}$ compounds (C30-CF1, C30-CSF1, C30-CFA1) were evaluated according to ASTM methods.

The kinematic viscosities at 100° C. and 40° C. (KV100 and KV40) were determined using ASTM D445 method.

The viscosity index (VI) were calculated from KV100 and KV40 by ASTM D2270 method. The pour point tests were carried out according to ASTM D97.

The kinematic viscosities and pour point measurements were performed at Southwest Research Institute, in San Antonio, Texas, USA.

DSC oxidation onset temperature and Noack volatility were measured according to ASTM E2009 (method B, 500 pis $O_2$) and ASTM D6375, respectively at Petro-lubricant Testing Laboratories, Inc, in Lafayette, N.J., USA.

Example 2. Synthesis of 5,5'-(dodecane-1,1-diyl)bis (2-pentylfuran) ($C_{30}$-CF1) by HAA of 2-pentylfuran and lauraldehyde

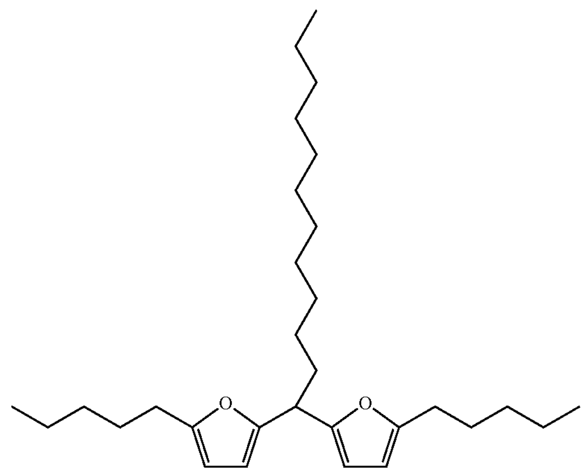 [SMILES: CCCCCCCCCCCC(c1ccc(CCCCC)o1)c1ccc(CCCCC)o1]

$C_{30}$-CF1 was synthesized using the HAA procedure disclosed hereinabove and was used for screening of various catalysts, as the commercial PAOs synthetic base oils contain $C_{30}$ alkane as the major compound. Secondly, synthesis of $C_{30}$-CF1 will provide a new alkylated furan aromatic lubricant base oil, which is not in the portfolio of current products. And lastly, catalytic HDO of $C_{30}$-CF1 will produce $C_{30}$-CFA1, which is structurally and atomically identical to $C_{30}$ alkanes in commercial PAOs.

Example 3. Synthesis of 5,5'-(dodecane-1,1-diyl)bis(2-pentyltetrahydrofuran) (C30-CSF1) by Hydrogenation of $C_{30}$-CF1

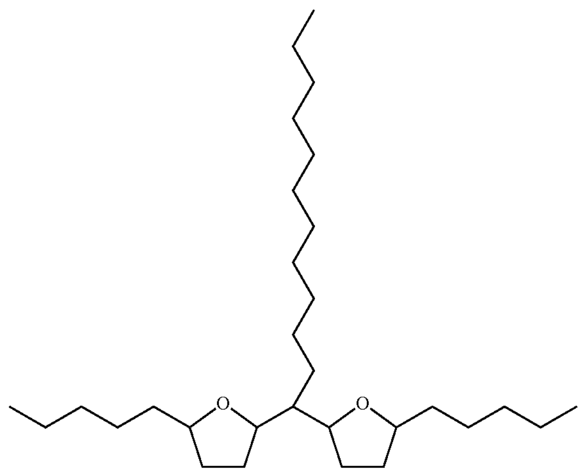 [SMILES: CCCCCCCCCCCC(C1CCC(CCCCC)O1)C1CCC(CCCCC)O1]

Mild hydrogenation of $C_{30}$-CF1 with a pre-reduction of commercial Pd/C catalyst produced $C_{30}$-CSF1 with high yield (90%).

Example 4. Synthesis of 10-nonylhenicosane ($C_{30}$-CFA1) by Hydrodeoxygenation of $C_{30}$-CF1

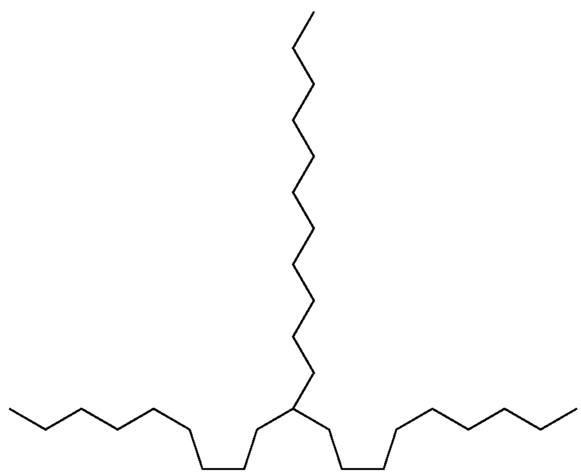 [SMILES: CCCCCCCCCCCC(CCCCCCCCC)CCCCCCCCC]

Figure 10:
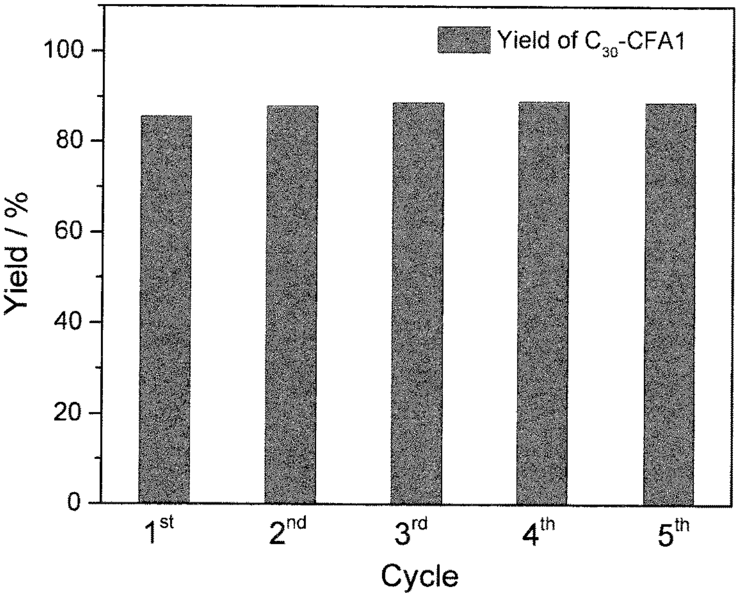
FIG. 10 shows recyclability of Ir—$ReO_x/SiO_2$ for the HDO of $C_{30}$-CF1. (Reaction condition: Ir—$ReO_x/SiO_2$ (0.15 g), $C_{30}$-CF 0.3 g, 170° C., $H_2$ 5 MPa, 12 hr).
Figure 11:
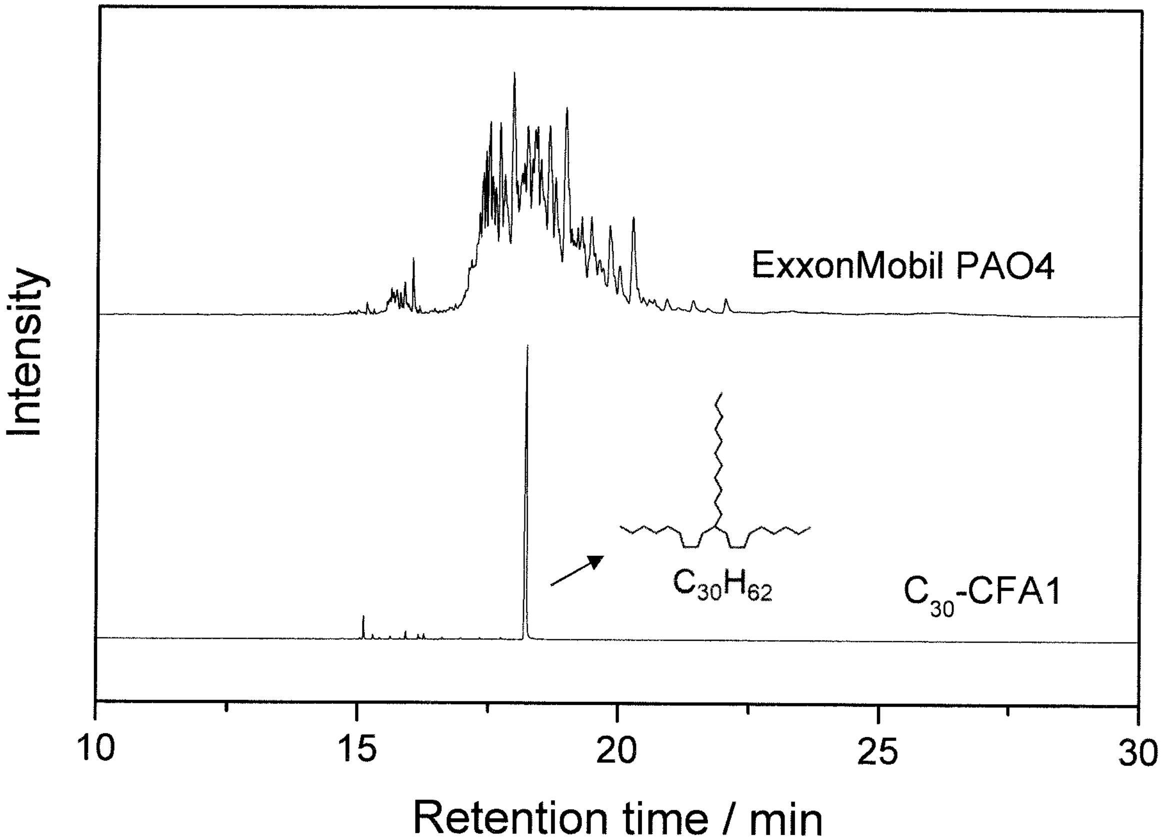
FIG. 11 shows gas chromatograms trace of $C_{30}$-CFA1 synthesized according to the present invention and a commercially available PAO-based lubricant oil (ExxonMobil PAO4).

Hydrodeoxygenation of $C_{30}$-CF1 was carried out over an Ir—$ReO_x/SiO_2$ catalyst, which has been demonstrated to have excellent catalytic performance for furans decyclization and dexoygenation (Reference 17) via a synergy of hydrogenation sites of Ir and acidic sites of partially reduced $ReO_x$, and yielded 86% $C_{30}$-CFA1 at 170° C. and 5 MPa $H_2$ for 12 h. A small amount of $C_{21}$- and $C_9$-alkanes were formed via C—C cracking. The recovered catalyst, upon regeneration by calcination before each cycle, demonstrated comparable performance in the yield of $C_{30}$-CFA1 in five consecutive runs, as shown in FIG. 10, indicating high stability of the Ir—$ReO_x/SiO_2$ catalyst.

As detailed hereinabove, $C_{30}$-CF1, $C_{30}$-CSF1 and $C_{30}$-CFA1 compounds have been formed, for use as a base oil for lubricant or personal care products, with very high selectivity; thus, mitigating expensive and complex separation challenges associated with commercial mineral and synthetic base oils.

Example 5. Synthesis of ($C_{22}$-$C_{34}$)-CF Compounds and ($C_{22}$-$C_{34}$)-CFA Compounds The synthetic platform demonstrated for making, $C_{30}$-CF1, $C_{30}$-CSF1 and $C_{30}$-CFA1 compounds, for use as base oils for lubricants or personal care products, was used to produce CFs and CFAs base oils of carbon numbers ranging between 22-34 and different branching, as summarized in Table 2, to tune specifications of base-oils. This was achieved by using 2-alkylfurans and aldehydes of different carbon length and substituents, and Aquivion® PW98 and Ir—$ReO_x/SiO_2$ as the HAA and HDO catalysts, respectively, as summarized in Table 2.

TABLE 2

Synthesis of CFs and CFAs lubricant base oils using 2-alkylfurans and aldehydes of varying molecular sizes.

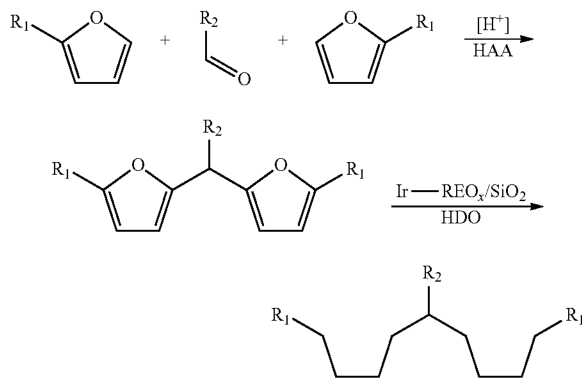

| | Reagents | | HAA reaction | | HDO reaction | |
|---|---|---|---|---|---|---|
| Entry | $R_1$ | $R_2$ | Products | Yield (%) | Products | Yield % |
| 1 | Methyl | nUndecyl | $C_{22}$-CF1 | 80 | $C_{22}$-CFA1 | 91 |
| 2 | Ethyl | nUndecyl | $C_{24}$-CF1 | 82 | $C_{24}$-CFA1 | 85 |
| 3 | nPropyl | nUndecyl | $C_{26}$-CF1 | 94 | $C_{26}$-CFA1 | 87 |
| 4 | nPentyl | nUndecyl | $C_{28}$-CF1 | 89 | $C_{28}$-CFA1 | 84 |
| 5 | nPentyl | nUndecyl | $C_{30}$-CF1 | 90 | $C_{30}$-CFA1 | 87 |
| 6 | nHexyl | nUndecyl | $C_{32}$-CF1 | 89 | $C_{32}$-CFA1 | 82 |
| 7[a] | nHeptyl | nUndecyl | $C_{34}$-CF1 | 85 | $C_{34}$-CFA1 | 83 |
| 8 | nPentyl | Methyl | $C_{20}$-CF1 | 89 | $C_{20}$-CFA1 | 87 |
| 9 | nPentyl | nPentyl | $C_{24}$-CF2 | 93 | $C_{24}$-CFA2 | 89 |
| 10 | nPentyl | nHeptyl | $C_{26}$-CF2 | 91 | $C_{26}$-CFA2 | 91 |
| 11 | nPentyl | nNonyl | $C_{28}$-CF2 | 87 | $C_{28}$-CFA2 | 87 |
| 12[b] | nPentyl | 2-Ethylpentyl | $C_{26}$-CF3 | 85 | $C_{26}$-CFA3 | 87 |
| 13[b] | nHexyl | 2-Ethylpentyl | $C_{28}$-CF3 | 86 | $C_{28}$-CFA3 | 82 |
| 14[b] | nHeptyl | 2-Ethylpentyl | $C_{30}$-CF2 | 88 | $C_{30}$-CFA2 | 81 |

Reaction condition: HAA reactions of 2-alkylfurans with aldehyde to CF were conducted using 0.05 g Aquivion ® PW98, 10 mmol 2-alkylfuran, 5 mmol aldehyde, at 65° C. for 6 hr.

[a]8 hr,

[b]12 hr. HDO of CF to the corresponding CFA over the Ir—$ReO_x/SiO_2$ catalyst was performed using 0.3 g CF in 10 ml cyclohexane solvent and 0.15 g catalyst at 5 MPa $H_2$ and 170° C. for 12 hr.

P—$SiO_2$ catalyst was also tested for the HAA reaction, as summarized below in Table 3.

TABLE 3

HAA reaction of different 2-alkylfurans with aldehydes over P—$SiO_2$.

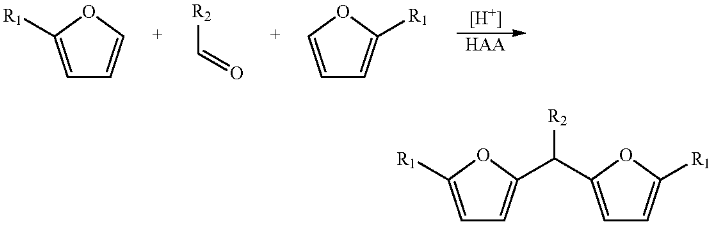

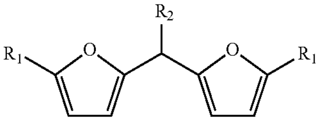

| Entry | Reagents $R_1$ | $R_2$ | HAA | Yield |
|---|---|---|---|---|
| 1 | Methyl | nUndecyl | $C_{22}$-CF1 | 80 |
| 2 | Eethyl | nUndecyl | $C_{24}$-CF1 | 82 |
| 3 | nPropyl | nUndecyl | $C_{26}$-CF1 | 94 |
| 4 | nPentyl | nUndecyl | $C_{28}$-CF1 | 89 |
| 5 | nPentyl | nUndecyl | $C_{30}$-CF1 | 90 |
| 6 | nHexyl | nUndecyl | $C_{32}$-CF1 | 89 |
| 7 | nHeptyl | nUndecyl | $C_{34}$-CF1 | 85 |
| 8 | nPentyl | Methyl | $C_{20}$-CF1 | 89 |
| 9 | nPentyl | nPentyl | $C_{24}$-CF2 | 93 |
| 10 | nPentyl | nHeptyl | $C_{26}$-CF2 | 91 |
| 11 | nPentyl | nNonyl | $C_{28}$-CF2 | 87 |
| 12[a] | nPentyl | 2-Ethylpentyl | $C_{26}$-CF3 | 87 |
| 13[a] | nHexyl | 2-Ethylpentyl | $C_{28}$-CF3 | 86 |
| 14[a] | nHeptyl | 2-Ethylpentyl | $C_{30}$-CF2 | 86 |

Reaction condition: HAA reaction of 2-alkylfuran with aldehyde to condensed furan over Aquivion ® PW98: 10 mmol 2-alkylfuran, 5 mmol aldehyde, 0.05 g catalyst, 65° C., 1.5 h.
[a]3 h.

Thus, Tables 2 and 3 clearly demonstrate that both Aquivion® PW98 and P—$SiO_2$ catalysts exhibit similar performance with the yields of CFs varying between 80-94% depending on their molecular sizes.

Similarly, HDO of CFs yields 81-91% CFAs depending on the molecular sizes of CFs and the chain lengths of alkyl groups of 2-alkylfurans and aldehydes.

Importantly, it should be noted that $C_{20}$- and $C_{30}$-CFAs of the present invention have structural similarity with current commercial PAO2 and PAO4 lubricant base oils. In addition, the CFs and CSFs products of the present invention, with tunable specifications will bring new market and sustainable opportunities in regards to applications and biodegradability. Feedstock flexibility to tailor molecular architecture with products selectivity is an additional advantage of our unique technology.

Base-oils containing more than one branching can enable products with lower pour points for very low temperature applications, e.g., refrigeration and aircrafts. HAA reaction of 2-alkylfuran with branched aldehydes, e.g. 2-ethylhexanal, which can be obtained by dehydrogenation of Guerbet alcohols, formed $C_{26}$~$C_{30}$ CFs (Table 2, entries 12-14). High yields of $C_{26}$~$C_{30}$ CFs were achieved over both Aquivion® PW98 and P—$SiO_2$ catalysts (Table 2, entries 12-14 and Table 3, entries 12-14). Their HDO with Ir—$ReO_x$/$SiO_2$ also produced high yields of corresponded $C_{26}$~$C_{30}$ CFAs (Table 2, entries 12-14).

Example 6. Properties of $C_{30}$-CF1, CSF1 and CFA1 Base Oils of the Present Invention and Commercial Formulated Lubricants Important properties of base oils such as, viscosity index (VI), pour point (PP), oxidation stability (DSC oxidation), and volatility (TGA Noack), of $C_{30}$-CF1, $C_{30}$-CSF1 and $C_{30}$-CFA1 base oils, of the present disclosure, were measured and are tabulated and compared with commercial mineral group III and PAO4 group IV base oils in Table 4.

TABLE 4

Properties of $C_{30}$-CF1, CSF1 and CFA1 base oils and their comparison with commercial formulated lubricants.

| Lubricant base-oils | $KV_{100}$[a] (cSt) | $KV_{40}$[a] (cSt) | VI[b] | PP[c] (° C.) | DSC oxidation onset T[d]/ ° C. | Noack Volatility[e]/ wt % |
|---|---|---|---|---|---|---|
| $C_{30}$-CF1 | 3.14 | 12.91 | 105 | <−63 | 170 | 10 |
| $C_{30}$-CSF1 | 3.91 | 17.92 | 113 | <−60 | 154 | 11.5 |
| $C_{30}$-CFA1 | 3.19 | 11.84 | 140 | −21 | 201 | 13.8 |
| ExxonMobil PAO4 | 4.1 | 19.0 | 126 | −66 | 221 | 14.0 |
| Phillips 66 Ultra-S4[f] | 4.25 | 19.64 | 123 | −20 | N/A | 14.9 |

[a]KV100 and KV40 are kinematic viscosities at 100° C. and 40° C., respectively (ASTM D445).
[b]VI: Viscosity index calculated from KV100 and KV40 (ASTM D2270).
[c]PP: Pour point (ASTM D97).
[d]Oxidation stability (ASTM E2009, method B, 500 pis $O_2$).
[e]Volatility (ASTM D6375).
[f]mineral group III base oil It should be noted that the as-synthesized $C_{30}$-base oils of the present invention have lower kinematic viscosities (KV40 and KV100) and better volatility than those of listed commercial base-oils while the VI of $C_{30}$-CF1 and $C_{30}$-CSF1 are slightly lower than those of the commercial alkane-based products because of furan and tetrahydrofuran rings in the structures of $C_{30}$-CF1 and $C_{30}$-CSF1. $C_{30}$-CSF1 has higher KV and VI than those of $C_{30}$-CF1, indicating molecular structures and content can control these properties.

The PP of $C_{30}$-CSF1 and $C_{30}$-CF1 are comparable to commercial PAO4, making them suitable for low temperature applications. The presence of oxygen containing rings as well as aromaticity in $C_{30}$-CSF1 and $C_{30}$-CF1 structures caused their lower DSC oxidation stability than commercial alkane products; thus $C_{30}$-CSF1 and $C_{30}$-CF1 base oils can be suitable for low temperature applications, although oxidation stability can be improved by appropriate formulation with antioxidant.

The PP and DSC oxidation stability of $C_{30}$-CFA1 are comparable to mineral group III base oil and PAO4 synthetic base oils while $C_{30}$-CFA1 has superior VI properties than the commercial products. This will enable automotive and other lubricating applications of $C_{30}$-CFA1 with improved fuel economy, energy efficiency and reduced $CO_2$ emissions. High VI ensures low viscosity changes with temperatures.

Example 8. Identification of all the Synthesized Compounds

A. Condensed Furan Compounds (CFs)

$C_{20}$-CF1: HAA of 2-Pentylfuran and Acetaldehyde

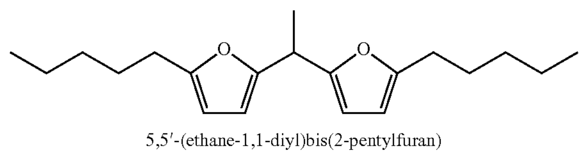 [SMILES: CCCCCc1ccc(C(C)c2ccc(CCCCC)o2)o1]

5,5′-(ethane-1,1-diyl)bis(2-pentylfuran)

$^1$H NMR (400 MHz, CDCl3): δ=5.80-5.75 (m, 4H), 4.01 (q, J=7.0 Hz, 1H), 2.46 (t, J=7.6, 4H), 1.56-1.47 (m, 4H), 1.45 (d, J=7.0, 3H), 1.29-1.13 (m, 8H), 0.79 (t, J=6.8, 6H).

$^{13}$C NMR (101 MHz, CDCl3): δ=155.39, 155.02, 105.24, 105.02, 33.30, 31.54, 28.16, 27.90, 22.57, 18.33, 14.19

HR-MS-LIFDI: $C_{20}H_{30}O_2$ Calc. mass 302.22)6, found Mass 302.2245.

$C_{22}$-CF1: HAA of 2-Methylfuran and Lauraldehyde

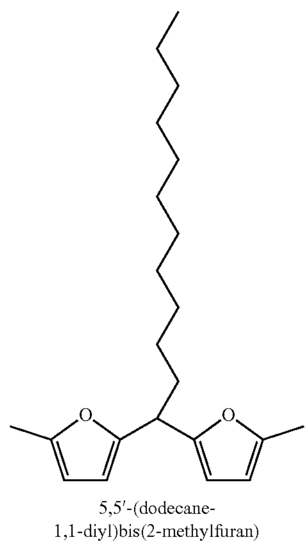

5,5′-(dodecane-1,1-diyl)bis(2-methylfuran)

$^1$H NMR (400 MHz, CDCl3): δ=5.91 (d, J=3.0 Hz, 2H), 5.88-5.82 (m, 2H), 3.90 (t, J=7.6 Hz, 1H), 2.25 (d, J=0.9, 6H), 1.97-1.87 (m, 2H), 1.36-1.18 (m, 18H), 0.88 (t, J=7.0, 3H).

$^{13}$C NMR (101 MHz, CDCl3): δ=154.31, 150.71, 106.10, 105.98, 39.10, 33.09, 32.07, 29.80, 29.79, 29.75, 29.62, 29.54, 29.51, 27.55, 22.85, 14.29, 13.77

HR-MS-LIFDI: $C_{22}H_{34}O_2$ theoretical. mass 330.2557, observed mass 330.2559

$C_{24}$-CF1: HAA of 2-Ethylfuran and Lauraldehyde

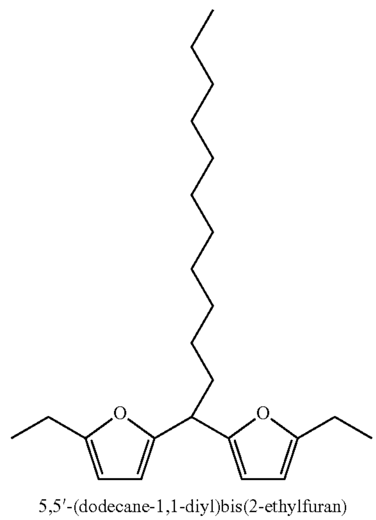 [SMILES: CCCCCCCCCCCC(c1ccc(CC)o1)c1ccc(CC)o1]

5,5′-(dodecane-1,1-diyl)bis(2-ethylfuran)

$^1$H NMR (400 MHz, CDCl3): δ=5.91 (d, J=3.0 Hz, 2H), 5.88-5.84 (m, 2H), 3.93 (t, J=7.6 Hz, 1H), 2.59 (q, J=7.5 Hz, 4H), 1.98-1.87 (m, 2H), 1.34-1.15 (m, 24H), 0.88 (t, J=7.0, 3H).

$^{13}$C NMR (101 MHz, CDCl3): δ=156.46, 154.22, 105.85, 104.26, 39.14, 33.27, 32.07, 29.80, 29.79, 29.75, 29.63, 29.54, 29.51, 27.55, 22.85, 21.51, 14.29, 12.29

HR-MS-EI: $C_{24}H_{38}O_2$ Calc. mass 358.2872, observed mass 358.2877

$C_{24}$-CF2: HAA of 2-Pentylfuran+Hexanal

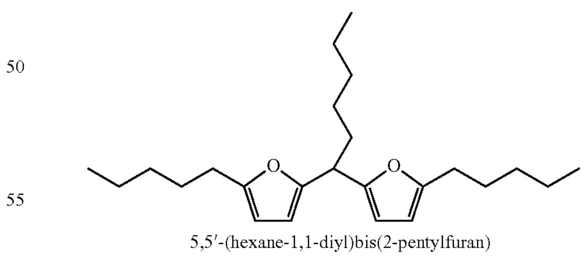

5,5′-(hexane-1,1-diyl)bis(2-pentylfuran)

$^1$H NMR (400 MHz, CDCl3): δ=5.94-5.80 (m, 4H), 3.92 (t, J=7.6 Hz, 1H), 2.56 (t, J=7.6 Hz, 4H), 1.97-1.84 (m, 2H), 1.68-1.55 (m, 4H), 1.42-1.21 (m, 14H), 0.96-0.81 (m, 9H).

$^{13}$C NMR (101 MHz, CDCl3): δ=155.23, 154.16, 105.84, 105.03, 39.15, 33.25, 31.76, 31.51, 28.16, 27.92, 27.21, 22.66, 22.58, 14.21, 14.18

HR-MS-LIFDI: $C_{24}H_{38}O_2$ Calc. Mass 358.2872, found Mass 358.2876.

$C_{26}$-CF1: HAA of 2-Propylfuran+Lauraldehyde

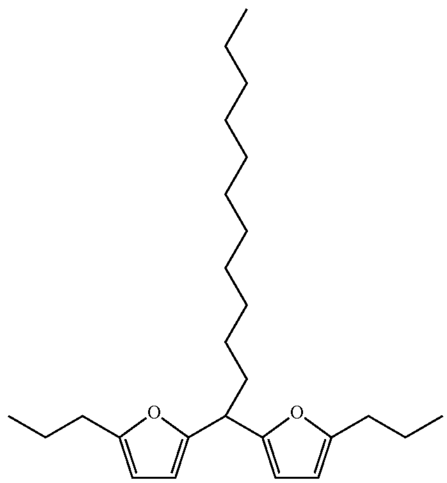

5,5′-(dodecane-1,1-diyl)bis(2-propylfuran)

$^1$H NMR (400 MHz, CDCl3): δ=5.94-5.83 (m, 4H), 3.92 (t, J=7.6 Hz, 1H), 2.56 (t, J=7.6 Hz, 4H), 1.98-1.87 (m, 2H), 1.69-1.55 (m, 4H), 1.35-1.16 (m, 18H), 0.99-0.83 (m, 9H).

$^{13}$C NMR (101 MHz, CDCl3): δ=155.01, 154.20, 105.83, 105.19, 39.15, 33.28, 32.07, 30.21, 29.81, 29.79, 29.74, 29.63, 29.54, 29.52, 27.53, 22.85, 21.60, 14.29, 13.88

HR-MS-LIFDI: $C_{26}H_{42}O_2$ Calc. Mass 386.3185, found Mass 386.3199.

$C_{26}$-CF2: HAA of 2-Pentylfuran+Octanal

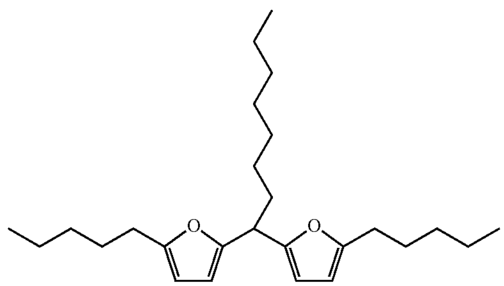

5,5′-(octane-1,1-diyl)bis(2-pentylfuran)

$^1$H NMR (400 MHz, CDCl3): δ=5.83-5.71 (m, 4H), 3.82 (t, J=7.6 Hz, 1H), 2.46 (t, J=7.6 Hz, 4H), 1.87-1.76 (m, 2H), 1.56-1.45 (m, 4H), 1.29-1.03 (m, 18H), 0.85-0.71 (m, 9H).

$^{13}$C NMR (101 MHz, CDCl3): δ=155.23, 154.16, 105.84, 105.03, 39.15, 33.30, 31.97, 31.51, 29.53, 29.32, 28.16, 27.92, 27.55, 22.80, 22.58, 14.26, 14.19

HR-MS-LIFDI: $C_{26}H_{42}O_2$ Calc. Mass 386.3185, found Mass 386.3182.

$C_{26}$-CF3: HAA of 2-Pentylfuran+2-Ethylhexanal

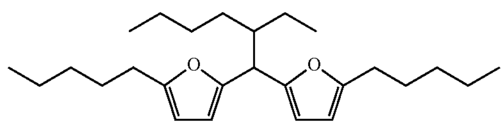

5,5′-(ethylhexane-1,1-diyl)bis(2-pentylfuran)

$^1$H NMR (400 MHz, CDCl3): δ=5.99-5.81 (m, 4H), 3.98 (d, J=7.2 Hz, 1H), 2.57 (t, J=7.6 Hz, 4H), 2.01-1.91 (m, 1H), 1.68-1.54 (m, 4H), 1.41-1.10 (m, 16H), 0.96-0.76 (m, 12H).

$^{13}$C NMR (101 MHz, CDCl3): δ=154.92, 154.91, 153.30, 153.27, 106.90, 106.68, 105.11, 105.09, 43.06, 42.26, 31.46, 30.38, 29.16, 28.16, 28.01, 28.00, 23.82, 23.11, 22.59, 14.24, 14.18, 11.25

HR-MS-LIFDI: $C_{26}H_{42}O_2$ Calc. Mass 386.3185, found Mass 386.3189.

$C_{28}$-CF1: HAA of 2-Butylfuran+Lauraldehyde

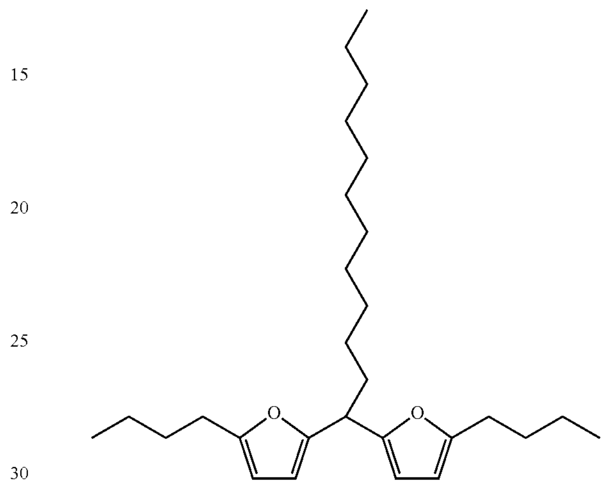

5,5′-(dodecane-1,1-diyl)bis(2-butylfuran)

$^1$H NMR (400 MHz, CDCl3): δ=5.94-5.83 (m, 4H), 3.92 (t, J=7.6 Hz, 1H), 2.57 (t, J=7.6 Hz, 4H), 1.98-1.87 (m, 2H), 1.64-1.53 (m, 4H), 1.42-1.18 (m, 22H), 0.95-0.84 (m, 9H).

$^{13}$C NMR (101 MHz, CDCl3): δ=155.19, 154.17, 105.83, 105.03, 39.14, 33.28, 32.07, 30.36, 29.81, 29.79, 29.75, 29.65, 29.56, 29.52, 27.89, 27.54, 22.85, 22.40, 14.29, 14.00

HR-MS-LIFDI: $C_{28}H_{46}O_2$ Calc. Mass 414.3476, found Mass 414.3498.

$C_{28}$-CF2: HAA of 2-Pentylfuran+Decanal

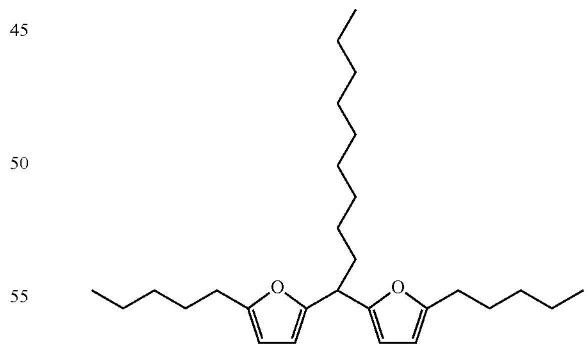

5,5′-(decane-1,1-diyl)bis(2-pentylfuran)

$^1$H NMR (400 MHz, CDCl3): δ=5.92-5.82 (m, 4H), 3.92 (t, J=7.6 Hz, 1H), 2.56 (t, J=7.6 Hz, 4H), 1.98-1.84 (m, 2H), 1.68-1.55 (m, 4H), 1.39-1.16 (m, 22H), 0.93-0.81 (m, 9H).

$^{13}$C NMR (101 MHz, CDCl3): δ=155.23, 154.16, 105.84, 105.03, 39.14, 33.30, 32.05, 31.51, 29.72, 29.65, 29.57, 29.47, 28.16, 27.92, 27.55, 22.84, 22.58, 14.29, 14.19

HR-MS-LIFDI: $C_{28}H_{46}O_2$ Calc. Mass 414.3476, found Mass 414.3498.

$C_{28}$-CF3: HAA of 2-Hexylfuran+2-Ethylhexanal

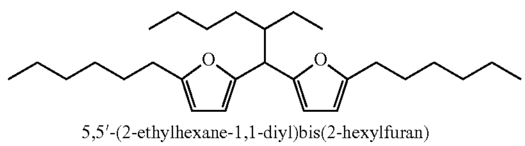 [SMILES: CCCCCCc1ccc(C(c2ccc(CCCCCC)o2)C(CC)CCCC)o1]
5,5′-(2-ethylhexane-1,1-diyl)bis(2-hexylfuran)

$^1$H NMR (400 MHz, CDCl3): δ=5.97-5.81 (m, 4H), 3.99 (d, J=7.2 Hz, 1H), 2.56 (t, J=7.6 Hz, 4H), 2.01-1.89 (m, 1H), 1.67-1.51 (m, 4H), 1.40-1.11 (m, 20H), 0.97-0.76 (m, 12H).

$^{13}$C NMR (101 MHz, CDCl3): δ=154.93, 154.91, 153.29, 153.26, 106.90, 106.87, 105.11, 105.09, 43.05, 42.25, 31.77, 30.37, 29.16, 28.95, 28.29, 28.20, 23.82, 23.11, 22.75, 14.26, 14.24, 11.25

HR-MS-LIFDI: $C_{28}H_{46}O_2$ Calc. Mass 414.3498, found Mass 414.349.

$C_{30}$-CF1: HAA of 2-Pentylfuran+Lauraldehyde

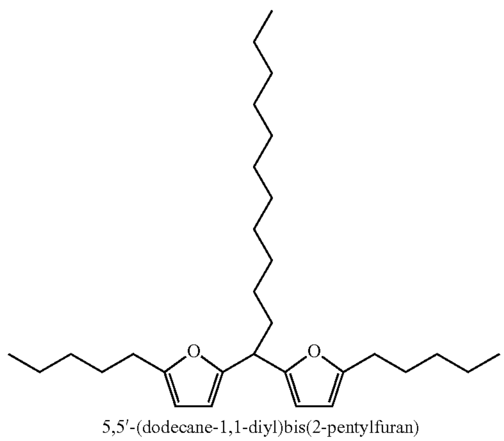 [SMILES: CCCCCCCCCCCC(c1ccc(CCCCC)o1)c1ccc(CCCCC)o1]
5,5′-(dodecane-1,1-diyl)bis(2-pentylfuran)

$^1$H NMR (400 MHz, CDCl3): δ=5.92-5.82 (m, 4H), 3.92 (t, J=7.6 Hz, 1H), 2.56 (t, J=7.6 Hz, 4H), 1.97-1.85 (m, 2H), 1.68-1.54 (m, 4H), 1.39-1.16 (m, 26H), 0.93-0.81 (m, 9H).

$^{13}$C NMR (101 MHz, CDCl3): δ=155.23, 154.17, 105.84, 105.03, 39.14, 33.29, 32.07, 31.51, 29.80, 29.78, 29.75, 29.65, 29.56, 29.51, 28.15, 27.91, 27.54, 22.84, 22.57, 14.29, 14.18

HR-MS-LIFDI: $C_{30}H_{50}O_2$ Calc. Mass 442.3811, found Mass 442.3814.

$C_{30}$-CF2: HAA of 2-Heptylfuran+2-Ethylhexanal

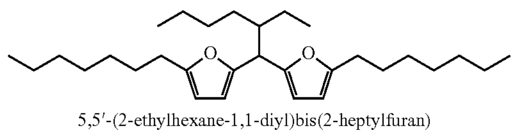 [SMILES: CCCCCCCc1ccc(C(c2ccc(CCCCCCC)o2)C(CC)CCCC)o1]
5,5′-(2-ethylhexane-1,1-diyl)bis(2-heptylfuran)

$^1$H NMR (400 MHz, CDCl3): δ=5.98-5.81 (m, 4H), 3.99 (d, J=7.2 Hz, 1H), 2.57 (t, J=7.6 Hz, 4H), 2.01-1.90 (m, 1H), 1.68-1.51 (m, 4H), 1.40-1.11 (m, 24H), 0.97-0.76 (m, 12H).

$^{13}$C NMR (101 MHz, CDCl3): δ=154.93, 154.92, 153.29, 153.26, 106.90, 106.88, 105.11, 105.09, 43.06, 42.25, 31.95, 30.38, 29.24, 29.16, 28.34, 28.33, 28.19, 23.82, 23.11, 22.81, 14.27, 14.25, 11.26

HR-MS-LIFDI: $C_{30}H_{50}O_2$ Calc. Mass 442.3811, found Mass 442.3811.

$C_{32}$-CF1: HAA of 2-Hexylfuran+Lauraldehyde

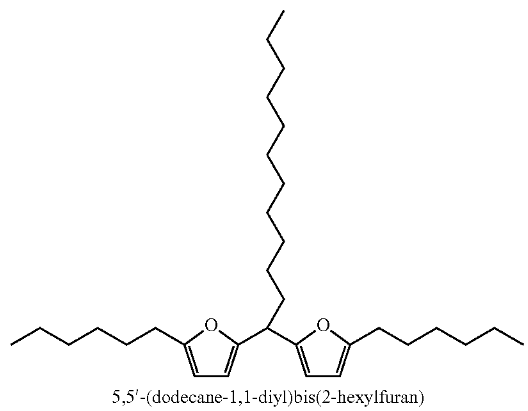 [SMILES: CCCCCCCCCCCC(c1ccc(CCCCCC)o1)c1ccc(CCCCCC)o1]
5,5′-(dodecane-1,1-diyl)bis(2-hexylfuran)

$^1$H NMR (400 MHz, CDCl3): δ=5.92-5.81 (m, 4H), 3.92 (t, J=7.6 Hz, 1H), 2.56 (t, J=7.6 Hz, 4H), 1.97-1.85 (m, 2H), 1.68-1.54 (m, 4H), 1.39-1.16 (m, 30H), 0.95-0.80 (m, 9H).

$^{13}$C NMR (101 MHz, CDCl3): δ=155.23, 154.16, 105.84, 105.03, 39.14, 33.30, 32.07, 31.76, 29.82, 29.80, 29.77, 29.66, 29.57, 29.52, 29.00, 28.20, 27.55, 22.85, 22.74, 14.29, 14.25

HR-MS-LIFDI: $C_{32}H_{54}O_2$ Calc. Mass 470.4124, found Mass 470.4112.

$C_{34}$-CF1: HAA of 2-Heptylfuran+Lauraldehyde

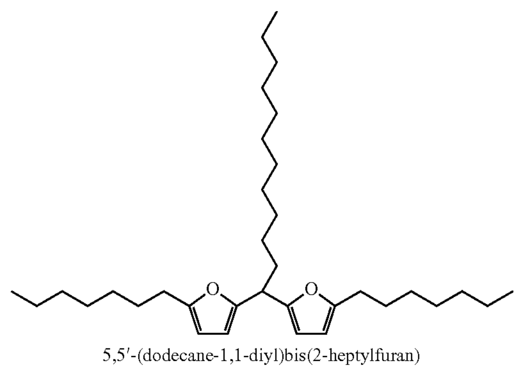 [SMILES: CCCCCCCCCCCC(c1ccc(CCCCCCC)o1)c1ccc(CCCCCCC)o1]
5,5′-(dodecane-1,1-diyl)bis(2-heptylfuran)

$^1$H NMR (400 MHz, CDCl3): δ=5.92-5.81 (m, 4H), 3.92 (t, J=7.6 Hz, 1H), 2.56 (t, J=7.6 Hz, 4H), 1.97-1.85 (m, 2H), 1.68-1.54 (m, 4H), 1.38-1.16 (m, 34H), 0.95- 0.82 (m, 9H).

$^{13}$C NMR (101 MHz, CDCl3): δ=155.23, 154.16, 105.84, 105.02, 39.15, 33.30, 32.07, 31.95, 29.82, 29.80, 29.77, 29.66, 29.57, 29.52, 29.28, 29.22, 28.25, 28.19, 27.55, 22.85, 22.81, 14.29, 14.26

HR-MS-LIFDI: $C_{34}H_{58}O_2$ Calc. Mass 498.4437, found Mass 498.4435.

Similarly, in accordance with various embodiment of the present invention, other CFs could be synthesized and identified, including, but not limited to:

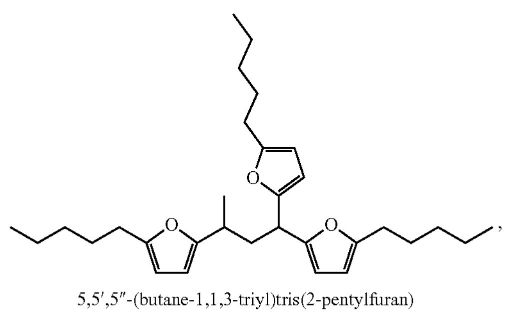
, 5,5′,5″-(butane-1,1,3-triyl)tris(2-pentylfuran)

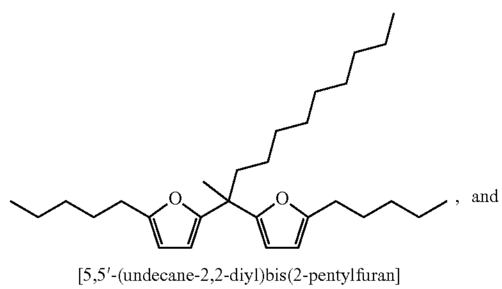
, and

[5,5′-(undecane-2,2-diyl)bis(2-pentylfuran]

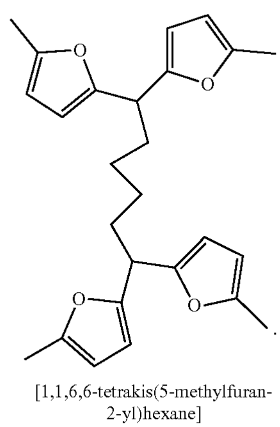
.

[1,1,6,6-tetrakis(5-methylfuran-2-yl)hexane]

B. Condensed Furan Alkane Compounds (CFAs)

C20-CFA1 from HDO of C20 Condensed Furan: HAA of 2-Pentylfuran+Acetaldehyde

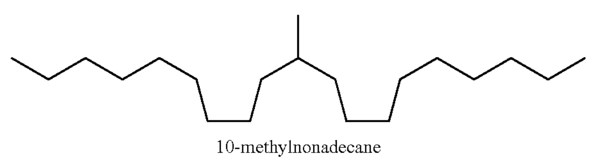 [SMILES: CCCCCCCCCC(C)CCCCCCCCC]

10-methylnonadecane $^1$H NMR (400 MHz, CDCl3), $^{13}$C NMR (101 MHz, CDCl3) and HR-MS-EI were performed to confirm the composition.

$C_{22}$-CFA1 from HDO of C22 Condensed Furan: HAA of 2-Methylfuran+Lauraldehyde

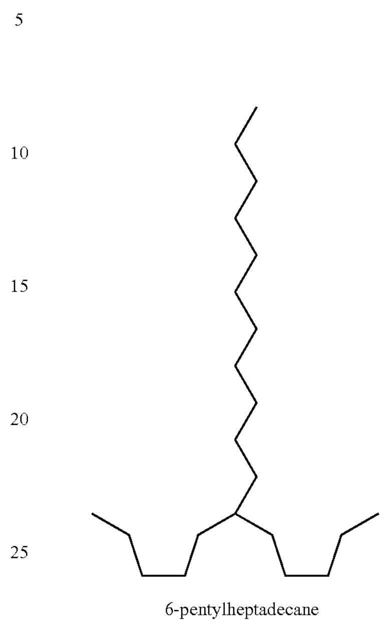

6-pentylheptadecane $^1$H NMR (400 MHz, CDCl3), $^{13}$C NMR (101 MHz, CDCl3) and HR-MS-EI were performed to confirm the composition.

$C_{24}$-CFA1 from HDO of C24 Condensed Furan: HAA of 2-Ethylfuran+Lauraldehyde

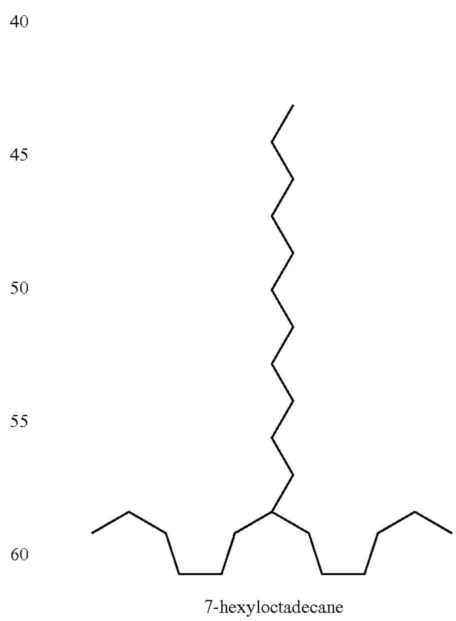

7-hexyloctadecane $^1$H NMR (400 MHz, CDCl3), $^{13}$C NMR (101 MHz, CDCl3) and HR-MS-EI were performed to confirm the composition.

$C_{24}$-CFA2 from HDO of C24 Condensed Furan: HAA of 2-Pentylfuran+Hexanal

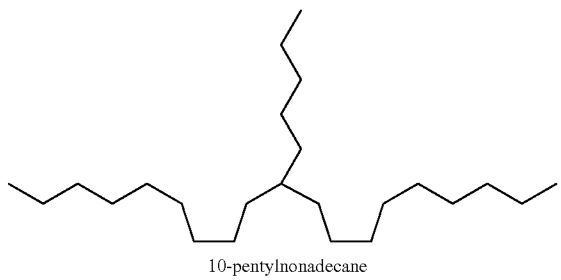 [SMILES: CCCCCCCCCC(CCCCC)CCCCCCCCC]

10-pentylnonadecane

$^1$H NMR (400 MHz, CDCl3), $^{13}$C NMR (101 MHz, CDCl3) and HR-MS-EI were performed to confirm the composition.

$C_{26}$-CFA1 from HDO of C26 Condensed Furan: HAA of 2-Propylfuran+Lauraldehyde

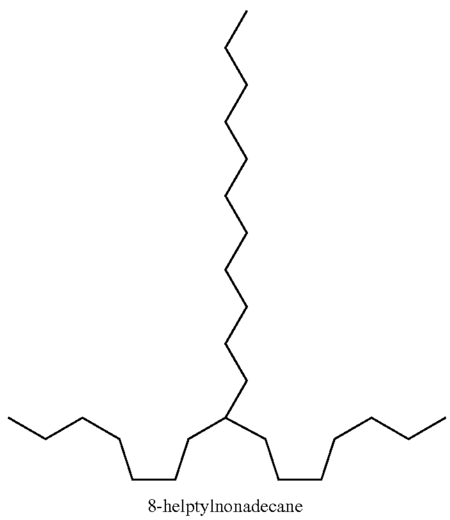 [SMILES: CCCCCCCCCCCC(CCCCCCC)CCCCCCC]

8-helptylnonadecane

$^1$H NMR (400 MHz, CDCl3), $^{13}$C NMR (101 MHz, CDCl3) and HR-MS-EI were performed to confirm the composition.

$C_{26}$-CFA2 from HDO of C26 Condensed Furan: HAA of 2-Pentylfuran+Octanal

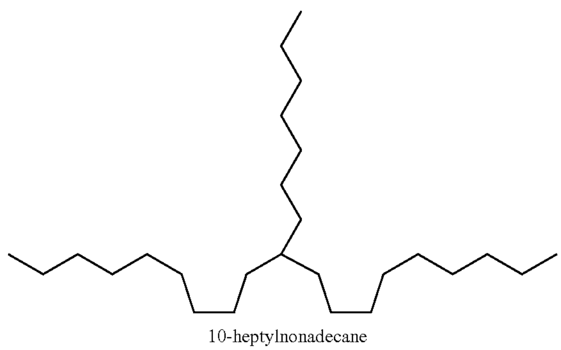 [SMILES: CCCCCCCCCC(CCCCCCC)CCCCCCCCC]

10-heptylnonadecane

$^1$H NMR (400 MHz, CDCl3), $^{13}$C NMR (101 MHz, CDCl3) and HR-MS-EI were performed to confirm the composition.

$C_{26}$-CFA3 from HDO of C26 Condensed Furan: HAA of 2-Pentylfuran+2-Ethylhexanal

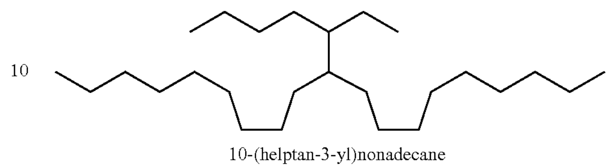

10-(helptan-3-yl)nonadecane

$^1$H NMR (400 MHz, CDCl3), $^{13}$C NMR (101 MHz, CDCl3) and HR-MS-EI were performed to confirm the composition.

$C_{28}$-CFA1 from HDO of C28 Condensed Furan: HAA of 2-Butylfuran+Lauraldehyde

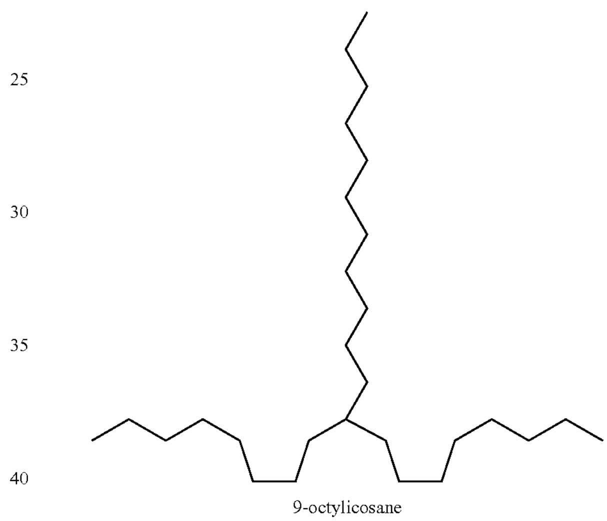

9-octylicosane

$^1$H NMR (400 MHz, CDCl3), $^{13}$C NMR (101 MHz, CDCl3) and HR-MS-EI were performed to confirm the composition.

$C_{28}$-CFA2 from HDO of C28 Condensed Furan: HAA of 2-Pentylfuran+Decanal

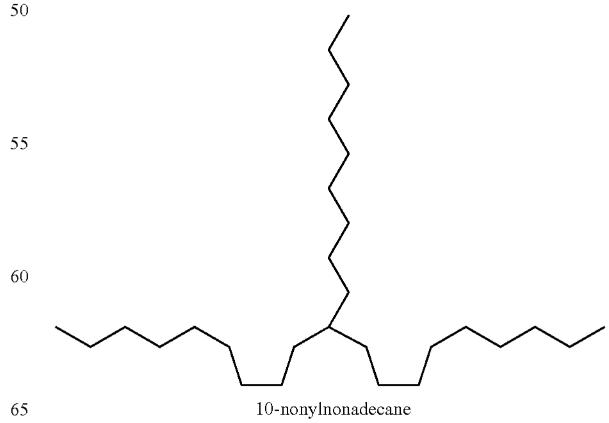

10-nonylnonadecane $^{1}$H NMR (400 MHz, CDCl3), $^{13}$C NMR (101 MHz, CDCl3) and HR-MS-EI were performed to confirm the composition.

$C_{28}$-CFA3 from HDO of C28 Condensed Furan: HAA of 2-Hexylfuran+2-Ethylhexanal

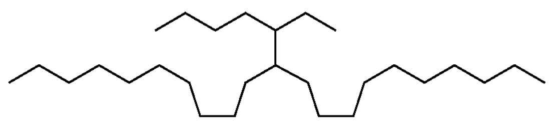

11-(heptan-3-yl)henicosane

1H NMR (400 MHz, CDCl3): δ=1.36-1.03 (m, 46H), 0.93-0.80 (m, 12H).

13C NMR (101 MHz, CDCl3): δ=41.59, 39.27, 32.09, 30.75, 30.73, 30.61, 30.32, 30.25, 30.05, 29.87, 29.82, 29.53, 28.22, 23.32, 23.28, 22.86, 14.37, 14.30, 12.87

HR-MS-LIFDI: $C_{28}H_{58}$ Calc. Mass 394.4539, found Mass 394.4511.

$C_{30}$-CFA1 from HDO of C30 Condensed Furan: HAA of 2-Pentylfuran+Lauraldehyde

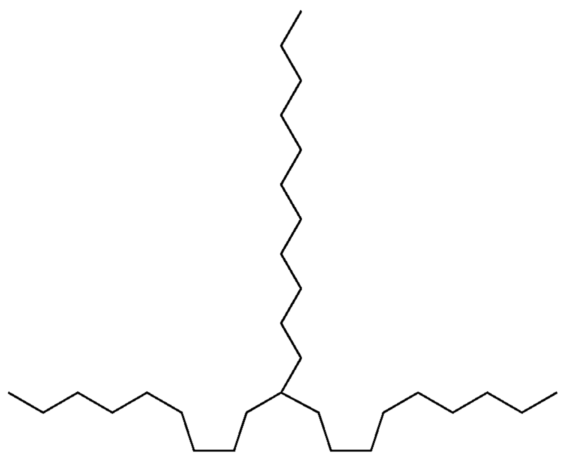

10-nonylhenicosane $^{1}$H NMR (400 MHz, CDCl3), $^{13}$C NMR (101 MHz, CDCl3) and HR-MS-EI were performed to confirm the composition.

$C_{30}$-CFA2 from HDO of C30 Condensed Furan: HAA of 2-Heptylfuran+2-Ethylhexanal

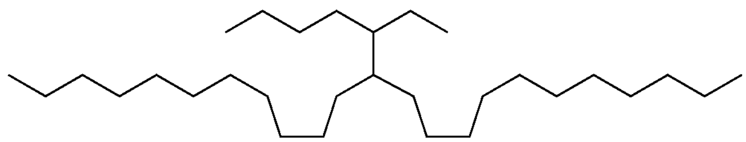

12-(heptan-3-yl)tricosane

1H NMR (400 MHz, CDCl3): δ=1.36-1.03 (m, 50H), 0.93-0.80 (m, 12H).

13C NMR (101 MHz, CDCl3): δ=41.59, 39.27, 32.09, 30.75, 30.73, 30.61, 30.29, 30.25, 30.04, 29.87, 29.82, 29.53, 28.28, 28.22, 23.32, 23.28, 22.86, 14.37, 14.30, 12.87

HR-MS-LIFDI: $C_{30}H_{62}$ Calc. Mass 422.4852, found Mass 422.4852.

$C_{32}$-CFA1 from HDO of C32 Condensed Furan: HAA of 2-Hexylfuran+Lauraldehyde

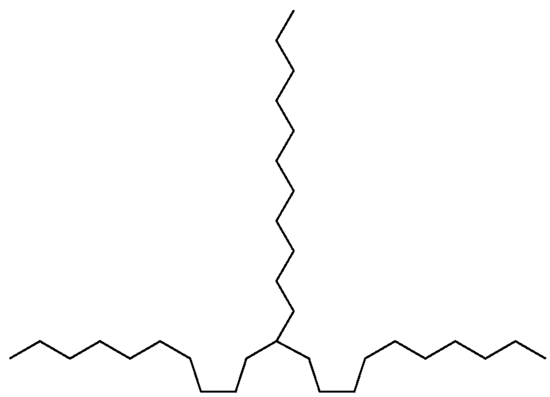

11-decyldocosane $^{1}$H NMR (400 MHz, CDCl3), $^{13}$C NMR (101 MHz, CDCl3) and HR-MS-EI were performed to confirm the composition.

$C_{34}$-CFA1 from HDO of C34 Condensed Furan: HAA of 2-Heptylfuran+Lauraldehyde

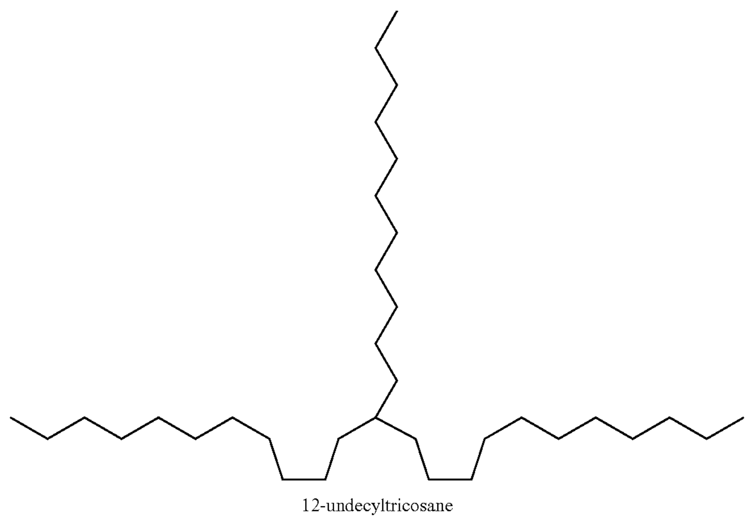 [SMILES: CCCCCCCCCCCC(CCCCCCCCCCC)CCCCCCCCCCC]

12-undecyltricosane $^1H$ NMR (400 MHz, CDCl3), $^{13}C$ NMR (101 MHz, CDCl3) and HR-MS-EI were performed to confirm the composition.

Similarly, in accordance with various embodiment of the present invention, other CFAs could be synthesized and identified, including, but not limited to:

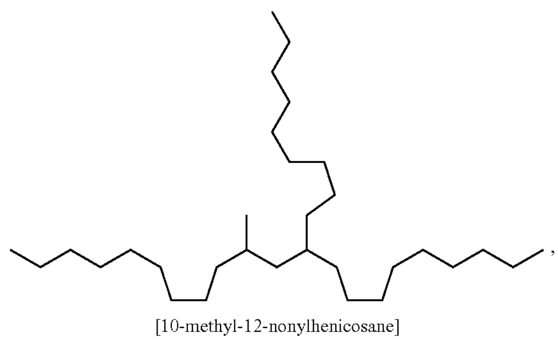

,

[10-methyl-12-nonylhenicosane]

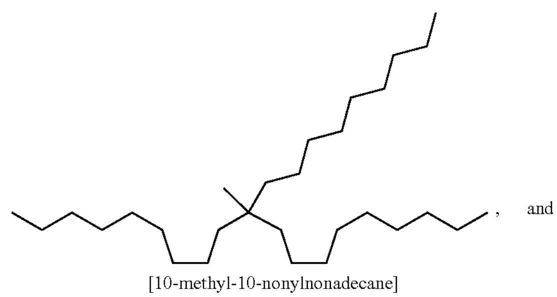

, and

[10-methyl-10-nonylnonadecane]

-continued

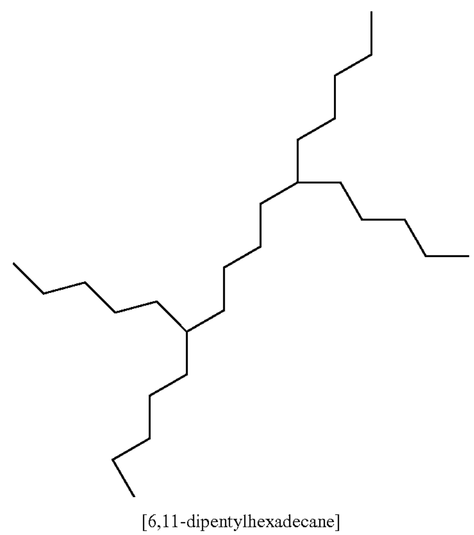

.

[6,11-dipentylhexadecane]

C. Condensed Saturated Furan Compounds (CSFs)

$C_{30}$-CSF1 from Hydrogenation of C30 Condensed Furan: HAA of 2-Pentylfuran+Lauraldehyde

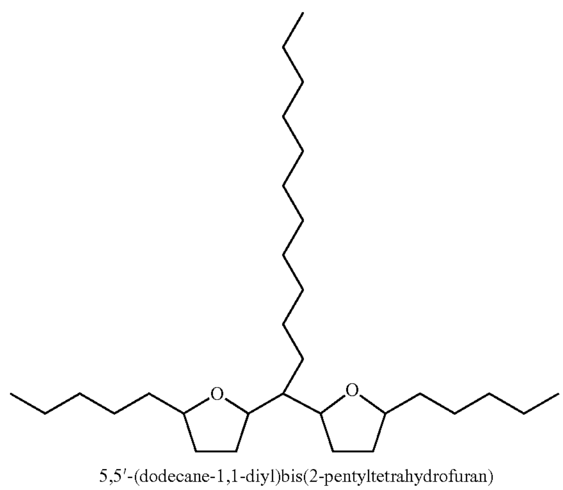 [SMILES: CCCCCCCCCCCC(C1CCC(CCCCC)O1)C1CCC(CCCCC)O1]

5,5′-(dodecane-1,1-diyl)bis(2-pentyltetrahydrofuran)

$^1$H NMR (400 MHz, CDCl3): δ=4.07-3.57 (m, 4H), 2.02-1.72 (m, 4H), 1.68-1.49 (m, 4H), 1.48-1.15 (m, 37H), 0.94-0.78 (m, 12H).

HR-MS-LIFDI: $C_{30}H_{58}O_2$ Calc. Mass 450.4437, found Mass 450.4442.

Similarly, in accordance with various embodiment of the present invention, other CSFs could be synthesized and identified, including, but not limited to:

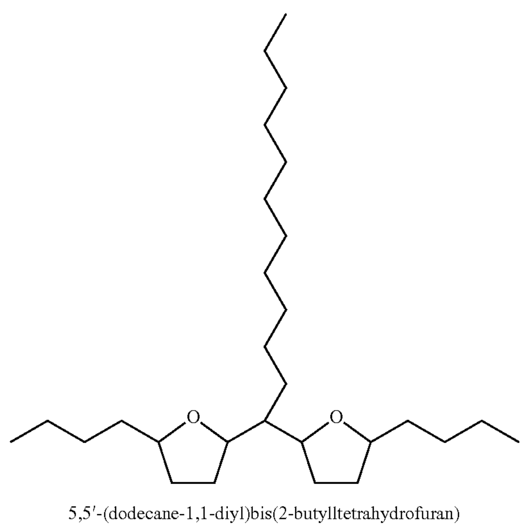

5,5′-(dodecane-1,1-diyl)bis(2-butylltetrahydrofuran)

-continued

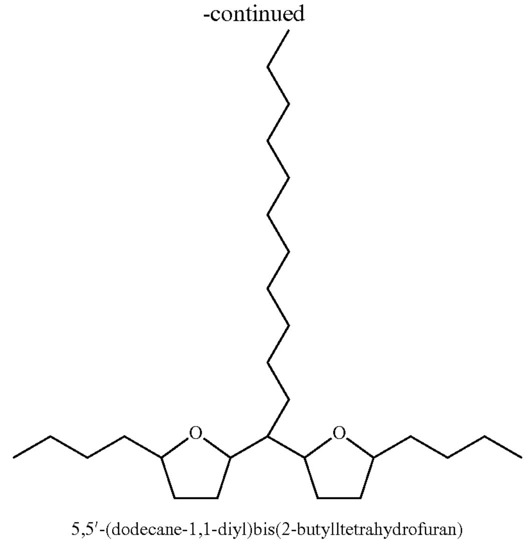

5,5′-(dodecane-1,1-diyl)bis(2-butylltetrahydrofuran)

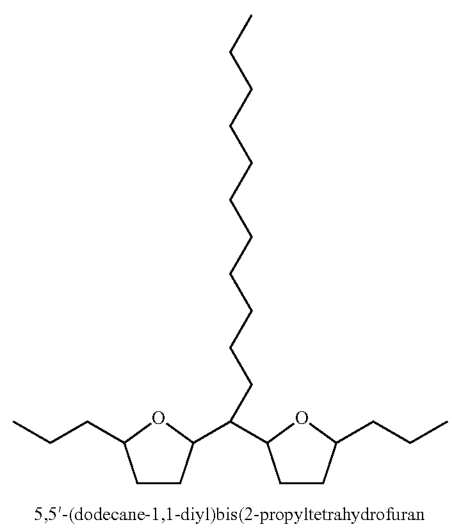

5,5′-(dodecane-1,1-diyl)bis(2-propyltetrahydrofuran

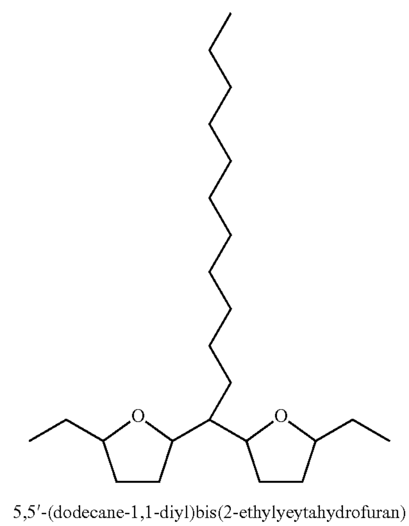

5,5′-(dodecane-1,1-diyl)bis(2-ethylyeytahydrofuran)

-continued

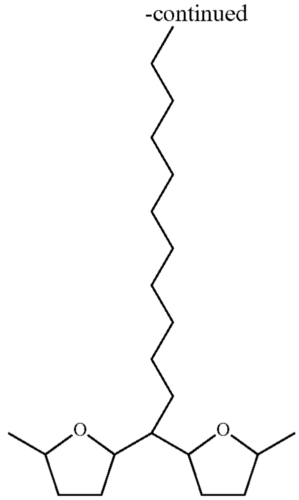

5,5′-(dodecane-1,1-diyl)bis(2-methyltetrahydrofuran)

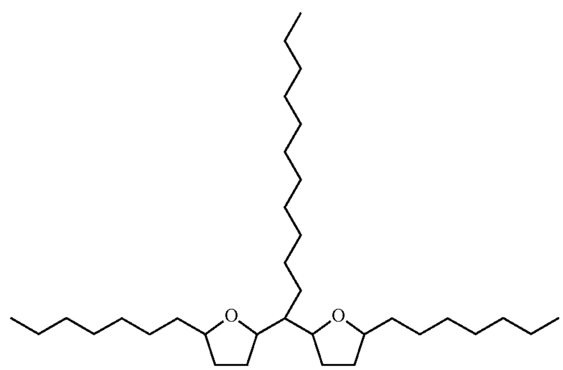

5,5′-(dodecane-1,1-diyl)bis(2-heptyltetrahydrofuran)

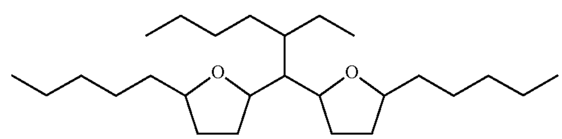

5,5′-(2-ethylhexane-1,1-diyl)bis(2-pentyltetrahydrofuran)

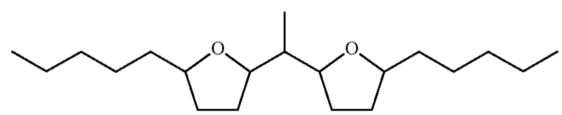

5,5′-(ethane-1,1-diyl)bis(2-pentyltetrahydrofuran)

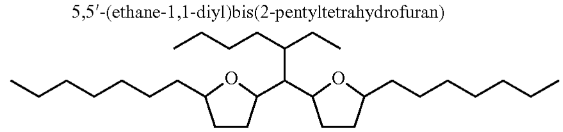

5,5′-(2-ethylhexane-1,1-diyl)bis(2-heptyltetrahydrofuran)

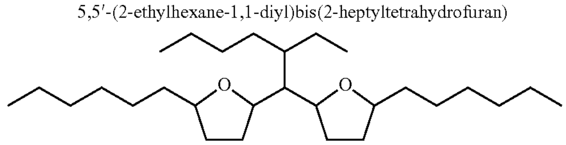

5,5′-(2-ethylhexane-1,1-diyl)bis(2-hexyltetrahydrofuran)

-continued

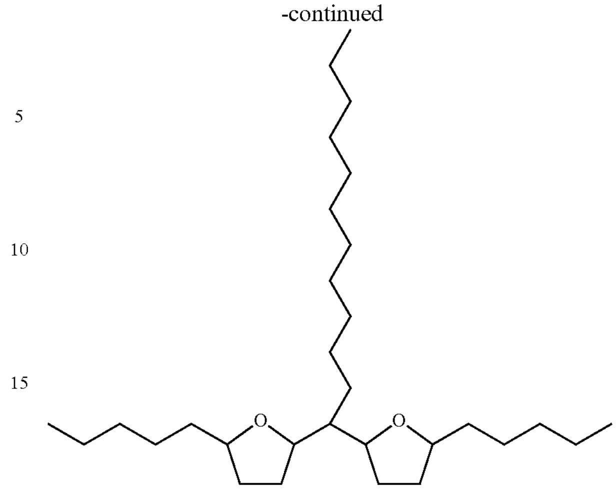

5,5′-(dodecane-1,1-diyl)bis(2-pentyltetrahydrofuran)

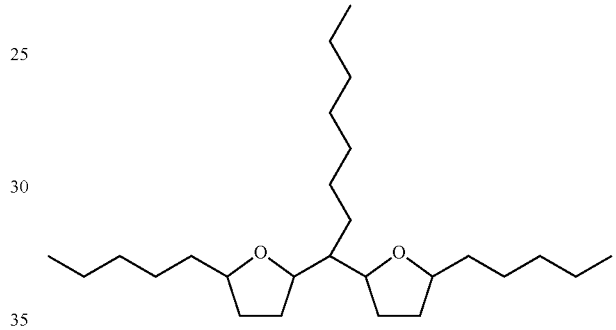

5,5′-(octane-1,1-diyl)bis(2-pentyltetrahydrofuran)

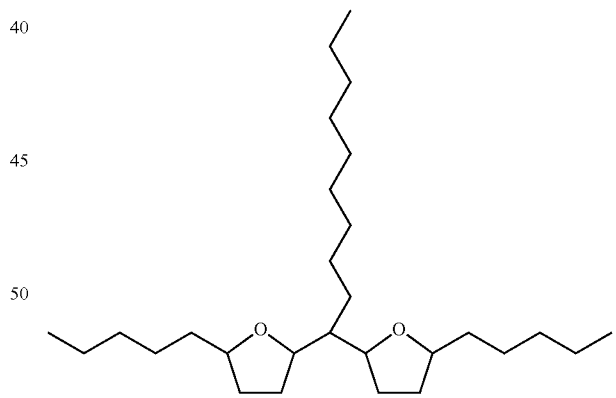

5,5′-(decane-1,1-diyl)bis(2-pentyltetrahydrofuran)

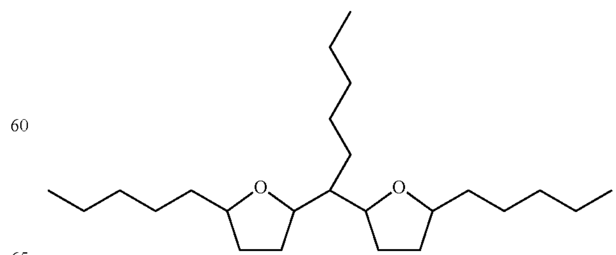

5,5′-(hexane-1,1-diyl)bis(2-pentyltetrahydrofuran)

-continued

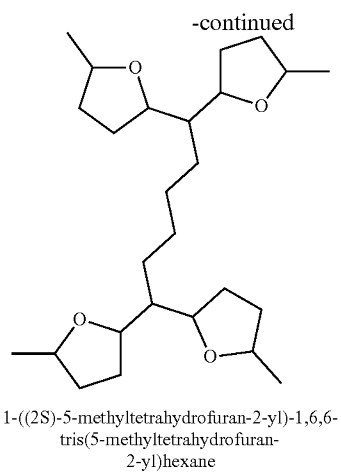

1-((2S)-5-methyltetrahydrofuran-2-yl)-1,6,6-tris(5-methyltetrahydrofuran-2-yl)hexane

REFERENCES AND NOTES

1. M. Balakrishnan, E. R. Sacia, S. Sreekumar, G. Gunbas, A. A. Gokhale, C. D. Scown, F. D. Toste, A. T. Bell, *Proc. Natl. Acad. Sci. USA* 112, 7645-7649 (2015).
2. M. Balakrishnan, G. E. Arab, O. B. Kunbargi, A. A. Gokhale, A. M. Grippo, F. D. Toste, A. T. Bell, *Green Chem.* 18, 3577-3581 (2016).
3. M. Gu, Q. Xia, X. Liu, Y. Guo, Y. Wang, *ChemSusChem* 10, 4102-4108 (2017)
4. D. Jadhav, A. M. Grippo, S. Shylesh, A. A. Gokhale, J. Redshaw, A. T. Bell, *ChemSusChem* 10, 2527-2533 (2017).
5. H. Ji, B. Wang, X. Zhang, T. Tan, *RSC Adv.* 5, 100443-100451 (2015).
6. H. Ji, X. Zhang, T. Tan, *Ind. Eng. Chem. Res.* 56, 7858-7864 (2017).
7. J. P. Lange, E. van der Heide, J. van Buijtenen, R. Price, *ChemSusChem* 5, 150-166 (2012).
8. C. Gunanathan, D. Milstein, *Science* 341, 1229712 (2013).
9. T. Yokoyama, N. Yamagata, *Appl. Catal. A: Gen.* 221, 227-239 (2001).
10. Y. Nakagawa, M. Tamura, K. Tomishige, *ACS Catal.* 3, 2655-2668 (2013).
11. D. S. Park, K. E. Joseph, M. Koehle, C. Krumm, L. Ren, J. N. Damen, M. H. Shete, H. S. Lee, X. Zuo, B. Lee, W. Fan, D. G. Vlachos, R. F. Lobo, M. Tsapatsis, P. J. Dauenhauer, *ACS Cent. Sci.* 2, 820-824 (2016).
12. Karam A., Vigier K. D. O., Marinkovic S., Estrine B., Oldani C. Jérôme F., *ACS Catal.*, 2017, 7, 2990-2997.
13. Pérez M. A., Bringué R., Iborra M., Tejero J., Cunill F., *Appl. Catal. A: Gen.* 2014, 482, 38-48.
14. Jones A. J., Zones S. I., Iglesia E., *J. Phys. Chem. C,* 2014, 118, 17787-17800.
15. Weingarten R., Tompsett G. A., Conner Jr. W. C., Huber G. W., J. *Catal.,* 2011, 279, 174-182.
16. I. Kioupis, E. J. Maginn, J. *Phys. Chem. B,* 104, 7774-7783 (2000).
17. S. Liu, S. Dutta, W. Zheng, N. S. Gould, Z. Cheng, B. Xu, B. Saha, D. G. Vlachos, *ChemSusChem* 10, 3225-3234 (2017).

What is claimed is:

1. A compound selected from one of the following:

(i) a condensed furan compound selected from the group consisting of 5,5-(ethane-11-dlyl)bis(2-pentylfuran), 5,5'-(dodecane-1,1-diyl)bis(2-methylfuran), 5,5'-(dodecane-1,1-diyl)bis(2-ethylfuran), 5,5'-(hexane-1,1-diyl)bis(2-pentylfuran), 5,5'-(dodecane-1,1-diyl)bis(2-propylfuran), 5,5'-(octane-1,1-diyl)bis(2-pentylfuran), 5,5'-(2-ethylhexane-1,1-diyl)bis(2-pentylfuran), 5,5'-(dodecane-1,1-diyl)bis(2-butylfuran), 5,5'-(decane-1,1-diyl)bis(2-pentylfuran), 5,5'-(2-ethylhexane-1,1-diyl) bis(2-hexylfuran), 5,5'-(dodecane-1,1-diyl)bis(2-pentylfuran), 5,5'-(2-ethylhexane-1,1-diyl)bis(2-heptylfuran), 5,5'-(dodecane-1,1-diyl)bis(2-hexylfuran), 5,5'-(dodecane-1,1-diyl)bis(2-heptylfuran), 5,5',5''-(butane-1,1,3-triyl)tris(2-pentylfuran), 5,5'-(undecane-2,2-diyl)bis(2-pentylfuran), and 1,1,6,6-tetrakis(5-methylfuran-2-yl) hexane, (ii) a condensed saturated furan compound selected from the group consisting of 5,5'-(dodecane-1,1-diyl)bis(2-pentyltetrahydrofuran), 5,5'-(dodecane-1,1-diyl)bis(2-butylltetrahydrofuran), 5,5'-(dodecane-1,1-diyl)bis(2-propyltetrahydrofuran), 5,5'-(dodecane-1,1-diyl)bis(2-ethyltetrahydrofuran), 5,5'-(dodecane-1,1-diyl)bis(2-methyltetrahydrofuran), 5,5'-(dodecane-1,1-diyl)bis(2-heptyltetrahydrofuran), 5,5'-(2-ethylhexane-1,1-diyl) bis(2-pentyltetrahydrofuran), 5,5'-(ethane-1,1-diyl)bis (2-pentyltetrahydrofuran), 5,5'-(2-ethylhexane-1,1-diyl)bis(2-heptyltetrahydrofuran), 5,5'-(2-ethylhexane-1,1-diyl)bis(2-hexyltetrahydrofuran), 5,5'-(octane-1,1-diyl)bis(2-pentyltetrahydrofuran), 5,5'-(decane-1,1-diyl)bis(2-pentyltetrahydrofuran), 5,5'-(hexane-1,1-diyl)bis(2-pentyltetrahydrofuran), and 1-((2S)-5-methyltetrahydrofuran-2-yl)-1,6,6-tris(5-methyltetrahydrofuran-2-yl) hexane, or (iii) a condensed furan alkane compound selected from the group consisting of 6-pentylheptadecane, 10-pentylnonadecane, 8-heptylnonadecane, 10-heptylnonadecane, 10-(heptan-3-yl) nonadecane, 10-nonylnonadecane, 11-(heptan-3-yl) henicosane, 10-nonylhenicosane, 12-(heptan-3-yl)tricosane, 12-undecyltricosane, 10-methyl-12-nonylhenicosane, and 10-methyl-10-nonylnonadecane, wherein the compound has a bio-based content in the range of 20 to 100%, according to ASTM-D6866.

2. A compound selected from one of the following:

(i) a condensed furan compound selected from the group consisting of 5,5-(ethane-11-dlyl)bis(2-pentylfuran), 5,5'-(dodecane-1,1-diyl)bis(2-methylfuran), 5,5'-(dodecane-1,1-diyl)bis(2-ethylfuran), 5,5'-(hexane-1,1-diyl)bis(2-pentylfuran), 5,5'-(dodecane-1,1-diyl)bis(2-propylfuran), 5,5'-(octane-1,1-diyl)bis(2-pentylfuran), 5,5'-(2-ethylhexane-1,1-diyl)bis(2-pentylfuran), 5,5'-(dodecane-1,1-diyl)bis(2-butylfuran), 5,5'-(decane-1,1-diyl)bis(2-pentylfuran), 5,5'-(2-ethylhexane-1,1-diyl) bis(2-hexylfuran), 5,5'-(dodecane-1,1-diyl)bis(2-pentylfuran), 5,5'-(2-ethylhexane-1,1-diyl)bis(2-heptylfuran), 5,5'-(dodecane-1,1-diyl)bis(2-hexylfuran), 5,5'-(dodecane-1,1-diyl)bis(2-heptylfuran), 5,5',5''-(butane-1,1,3-triyl)tris(2-pentylfuran), 5,5'-(undecane-2,2-diyl)bis(2-pentylfuran), and 1,1,6,6-tetrakis(5-methylfuran-2-yl) hexane, (ii) a condensed saturated furan compound selected from the group consisting of 5,5'-(dodecane-1,1-diyl)bis(2-pentyltetrahydrofuran), 5,5'-(dodecane-1,1-diyl)bis(2-butylltetrahydrofuran), 5,5'-(dodecane-1,1-diyl)bis(2-propyltetrahydrofuran), 5,5'-(dodecane-1,1-diyl)bis(2-ethyltetrahydrofuran), 5,5'-(dodecane-1,1-diyl)bis(2-methyltetrahydrofuran), 5,5'-(dodecane-1,1-diyl)bis(2- heptyltetrahydrofuran), 5,5'-(2-ethylhexane-1,1-diyl) bis(2-pentyltetrahydrofuran), 5,5'-(ethane-1,1-diyl)bis (2-pentyltetrahydrofuran), 5,5'-(2-ethylhexane-1,1-diyl)bis(2-heptyltetrahydrofuran), 5,5'-(2-ethylhexane-1,1-diyl)bis(2-hexyltetrahydrofuran), 5,5'-(octane-1,1-diyl)bis(2-pentyltetrahydrofuran), 5,5'-(decane-1,1-diyl)bis(2-pentyltetrahydrofuran), 5,5'-(hexane-1,1-diyl)bis(2-pentyltetrahydrofuran), and 1-((2S)-5-methyltetrahydrofuran-2-yl)-1,6,6-tris(5-methyltetrahydrofuran-2-yl) hexane, or (iii) a condensed furan alkane compound selected from the group consisting of 6-pentylheptadecane, 10-pentylnonadecane, 8-heptylnonadecane, 10-heptylnonadecane, 10-(heptan-3-yl) nonadecane, 10-nonylnonadecane, 11-(heptan-3-yl) henicosane, 10-nonylhenicosane, 12-(heptan-3-yl)tricosane, 12-undecyltricosane, 10-methyl-12-nonylhenicosane, and 10-methyl-10-nonylnonadecane, wherein the compound has a bio-based content in the range of 20 to 100%, according to ASTM-D6866.

3. A personal care composition comprising:

a. a base oil comprising one or more compounds according to claim 1;

b. an effective amount of one or more additives selected from the group consisting of pigment, fragrance, emulsifier, wetting agent, thickener, emollient, rheology modifier, viscosity modifier, gelling agent, antiperspirant agent, deodorant active, fatty acid salt, film former, anti-oxidant, humectant, opacifier, monohydric alcohol, polyhydric alcohol, fatty alcohol, preservative, pH modifier, a moisturizer, skin conditioner, stabilizing agent, proteins, skin lightening agents, topical exfoliants, antioxidants, retinoids, refractive index enhancer, photo-stability enhancer, SPF improver, UV blocker, and water.

4. The personal care composition of claim 3, further comprising an active ingredient selected from the group consisting of antibiotic, antiseptic, antifungal, corticosteroid, and anti-acne agent.

5. A pharmaceutical composition comprising:

a. a base oil comprising one or more compounds according to claim 1;

b. an effective amount of one or more pharmaceutically active ingredients; and

C. optionally, one or more pharmaceutically acceptable excipients.

6. A grease comprising a base oil comprising one or more compounds according to claim 1.

7. A lubricant composition comprising:

a. 30-99% by weight of a base oil comprising one or more compounds according to claim 1; and b. an effective amount of one or more lubricant additives.

8. The lubricant composition according to claim 7, wherein at least one of the one or more compounds has a furan ring or a tetrahydrofuran ring.

9. The lubricant composition according to claim 7, further comprising one or more co-base oils selected from the group consisting of API Group I base oil, Group II base oil, Group III base oil, Group IV base oil, Group V base oil, gas-to-liquid base oil, and combinations thereof.

10. A method of making the compound according to claim 1:

wherein the method comprises the steps of:

a) providing a first component comprising one or more of a 2-alkylfuran and a second component comprising one or more of:

i) an aldehyde, ii) a dialdehyde, iii) an enal, or iv) a ketone, wherein at least one of the first component and the second component is bio-derived from a renewable source, wherein the first component and the second component are selected from one of the following combinations:

| First Component | Second Component |
|---|---|
| 2-pentylfuran | acetaldehyde |
| 2-methylfuran, 2-ethylfuran, 2-propylfuran, 2-butylfuran, 2-pentylfuran, 2-hexylfuran, 2-heptylfuran, | lauraldehyde |
| 2-pentylfuran | hexanal, octanal, decanal |
| 2-pentylfuran, 2-hexylfuran, 2-heptylfuran | 2-ethylhexanal |
| 2-methylfuran | hexanedial |
| 2-pentylfuran | crotonaldehyde |
| 2-pentylfuran | 2-undecanone |

b) condensing the first component with the second component in the presence of an acidic catalyst to form the condensed furan compound;

c) optionally hydrogenating the condensed furan compound in the presence of a hydrogenation catalyst to obtain the condensed saturated furan compound; and d) optionally hydrodeoxygenating the condensed furan compound or the condensed saturated furan compound in the presence of a hydrodeoxygenation catalyst and hydrogen to obtain the condensed furan alkane compound.

11. The method according to claim 10, wherein the step of providing an aldehyde comprises at least one of dehydrogenating one or more biomass derived alcohols and selective hydrogenation of one or more fatty acids from one or more natural oils or waste cooking oils.

12. The method according to claim 10, wherein the step of condensing the first component with the second component comprises carrying out the condensing in the presence of at least one thiol selected from the group consisting of ethanethiol, propanethiol, butanethiol and combinations thereof.

13. The method according to claim 10, wherein the acidic catalyst comprises at least one acidic catalyst selected from the group consisting of liquid acids and solid acids.

14. The method according to claim 10, wherein step c) is performed in the presence of a hydrogenation catalyst and the hydrogenation catalyst is a metal base catalyst selected from palladium catalysts supported on carbon or acidic materials and nickel based catalysts.

15. The method according to claim 10, wherein the step d) is performed in the presence of a hydrodeoxygenation catalyst and the hydrodeoxygenation catalyst is a solid acid supported metal based catalyst or a physical mixture of a metal based catalyst.

16. The method according to claim 15, wherein the hydrodeoxygenation catalyst is a solid acid supported metal based catalyst selected from Ni/ZSM-5, Pd/ZSM-5, Pd/BEA, or a physical mixture of a metal based catalyst with a solid acid and a supported metal-metal oxide catalyst.

17. The method according to claim 14, wherein the palladium catalysts are selected from the group consisting of Pd/C, $Pd/SiO_2$ and $Pd/Al_2O_3$, and the nickel based catalysts comprise Raney Ni.

18. The method according to claim 15, wherein the metal based catalyst includes Pd/C, Pd/$SiO_2$ or Pt/C, with a solid acid.

19. The method according to claim 16, wherein the solid acid includes Pd/C+ZSM-5, Pd/C+BEA, Pt/C+BEA, and the supported metal-metal oxide catalyst includes Ir-$ReO_x$/$SiO_2$, Ir—$MoO_x$/$SiO_2$ or $^1M^2MO/SiO_2$, wherein $^1M$=Ir, Ru, Ni, Co, Pd, Pt, or Rh and $^2M$=Re, Mo, W, Nb, Mn, V, Ce, Cr, Zn, Co, Y, or Al.

* * * * *